(12) United States Patent
Sword

(10) Patent No.: US 9,277,751 B2
(45) Date of Patent: Mar. 8, 2016

(54) FUNGAL ENDOPHYTES FOR IMPROVED CROP YIELDS AND PROTECTION FROM PESTS

(71) Applicant: The Texas A&M University System, College Station, TX (US)

(72) Inventor: Gregory A. Sword, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 14/535,292

(22) Filed: Nov. 6, 2014

(65) Prior Publication Data

US 2015/0126365 A1 May 7, 2015

Related U.S. Application Data

(60) Provisional application No. 61/900,929, filed on Nov. 6, 2013, provisional application No. 61/900,935, filed on Nov. 6, 2013.

(51) Int. Cl.
*A01N 25/26* (2006.01)
*A01N 63/00* (2006.01)
*A01N 63/04* (2006.01)

(52) U.S. Cl.
CPC ..................................... *A01N 63/04* (2013.01)

(58) Field of Classification Search
None
See application file for complete search history.

(56) References Cited

U.S. PATENT DOCUMENTS

| | | | |
|---|---|---|---|
| 5,730,973 | A | 3/1998 | Morales et al. |
| 2010/0227357 | A1* | 9/2010 | Redman et al. .................. 435/29 |
| 2011/0182862 | A1 | 7/2011 | Green et al. |
| 2012/0144533 | A1* | 6/2012 | Craven ........................... 800/300 |
| 2013/0071425 | A1* | 3/2013 | Vidal et al. ................ 424/195.15 |

OTHER PUBLICATIONS

Sword (Fungal Endophytes to protect cotton from insects and nematedes, PowerPoint presentation dated Dec. 7, 2012).*
Zhou et al. (Effects of the Fungal Endophyte *Paecilomyces* sp. in Cotton On the Root-Knot Nematode *Meloidogyne incognita*, poster dated 17/13).*
International Search Report and Written Opinion regarding International Application No. PCT/US2014/064411, dated Mar. 27, 2015.
Waller et al., "The endophytic fungus *Piriformospora indica* reprograms barley to salt-stress tolerance, disease resistance, and higher yield," *PNAS* 102(38):13386-13391, 2005.
Xu et al., "Biosynthesis of the cyclooligomer despipeptide bassianolide, an insecticidal virulence factor of *Beauveria bassiana*," *Fungal Genetics and Biology* 46:353-364, 2009.
Zuccaro et al., "Endophytic Life Strategies Decoded by Genome and Transcriptome Analyses of the Mutualistic Root Symbiont *Piriformospora indica*," *PLOS Pathogens* 7(10):e1002290, 2011.
Ek-Ramos et al., "Spatial and temporal variation in fungal endophyte communities isolated from cultivated cotton (*Gossypium hirsutum*)," *PLoS One* 8(6):e66049, 2013.
Ek-Ramos, "Ecology, distribution and benefits of fungal endophytes isolated from cultivated cotton (*Gossypium hirsutum*) in Texas," PowerPoint Presentation dated Nov. 7, 2012.
Sword, "Manipulating fungal endophytes to protect plants from insects and nematodes," PowerPoint Presentation dated Aug. 7, 2013.
Sword et al., "Manipulating fungal endophytes for the protection of cotton in the field," PowerPoint Presentation dated Jan. 7, 2013.
Sword et al., "Field trials of potentially beneficial fungal endophytes in cotton," PowerPoint Presentation dated Jan. 7, 2013.
Sword, "Fungal endophytes to protect cotton from insects and nematodes," PowerPoint Presentation dated Dec. 7, 2012.
Sword, "Natural Enemies—The Forgotten Basis of IPM?," PowerPoint Presentation dated Sep. 6, 2013.
Castillo et al., "Fungal endophytes: plant protective agents against herbivores," PowerPoint Presentation dated Aug. 4, 2013.
Valencia et al., "Endophytic Establishment as an Unintended Consequence of Biocontrol with Fungal Entomopathogens," PowerPoint Presentation dated Jan. 7, 2013.
Kalns et al., "The effects of cotton fungal endophytes in the field on arthropod community structure," PowerPoint Presentation dated Jan. 7, 2013.
Castillo et al., "Fungal Entomopathogenic Endophytes: Negative Effects on Cotton Aphid Reproduction in Greenhouse and Field Conditions," PowerPoint Presentation dated Mar. 23, 2013.
Zhou et al., "Effects of the Fungal Endophyte *Paecilomyces* sp. in Cotton on the Roo-Knot Nematode *Meloidogyne incognita*," poster dated Jan. 7, 2013.
Ek-Ramos et al., "Spatial and temporal variation in fungal endophyte communities isolated from cultivated cotton (*Gossypium hirsutum*)," PowerPoint Presentation dated Jan. 7, 2013.

* cited by examiner

*Primary Examiner* — Alton Pryor
(74) *Attorney, Agent, or Firm* — Fenwick & West LLP

(57) ABSTRACT

The invention provides a synthetic combination of a crop and at least one fungal endophyte, wherein the crop is a host plant of the endophyte. Provided are also methods and compositions for producing such synthetic combinations. The endophyte reproduces and enhances the agronomic characteristics of the crop. Methods for inoculating the host plant with the endophyte, for propagating the host-endophyte combination, and for detecting the presence of the endophyte and of its metabolites within a host plant are also described.

35 Claims, 29 Drawing Sheets

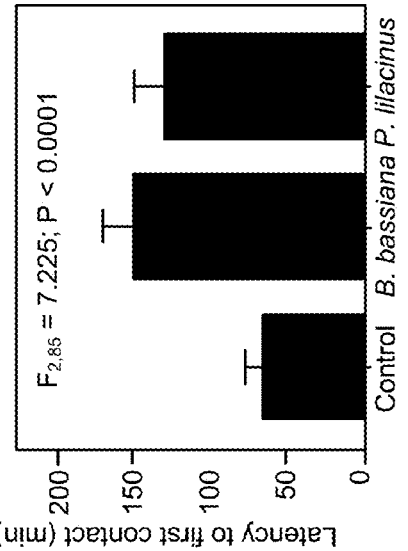
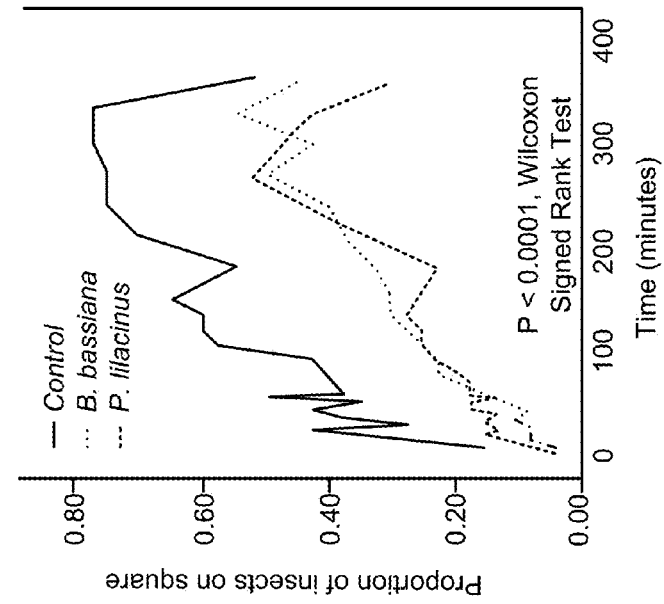
FIG. 6A

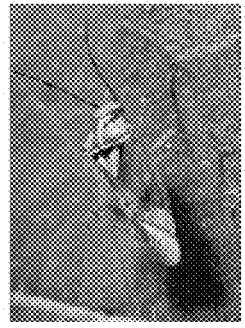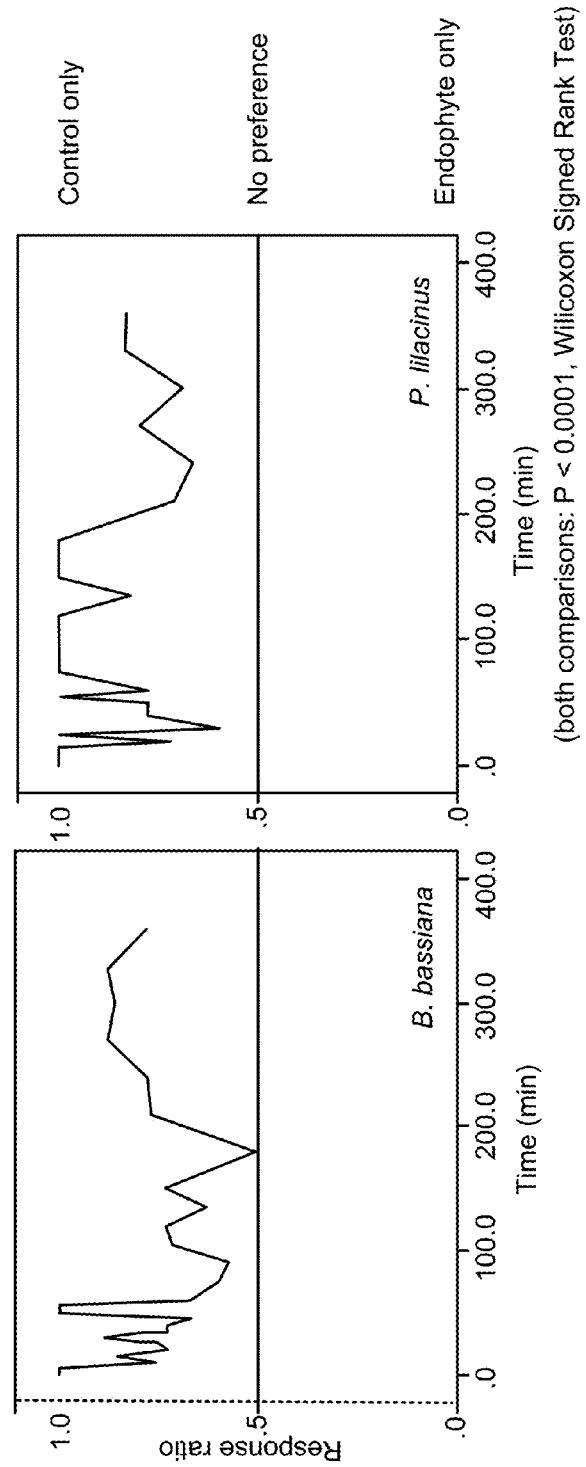
FIG. 6B

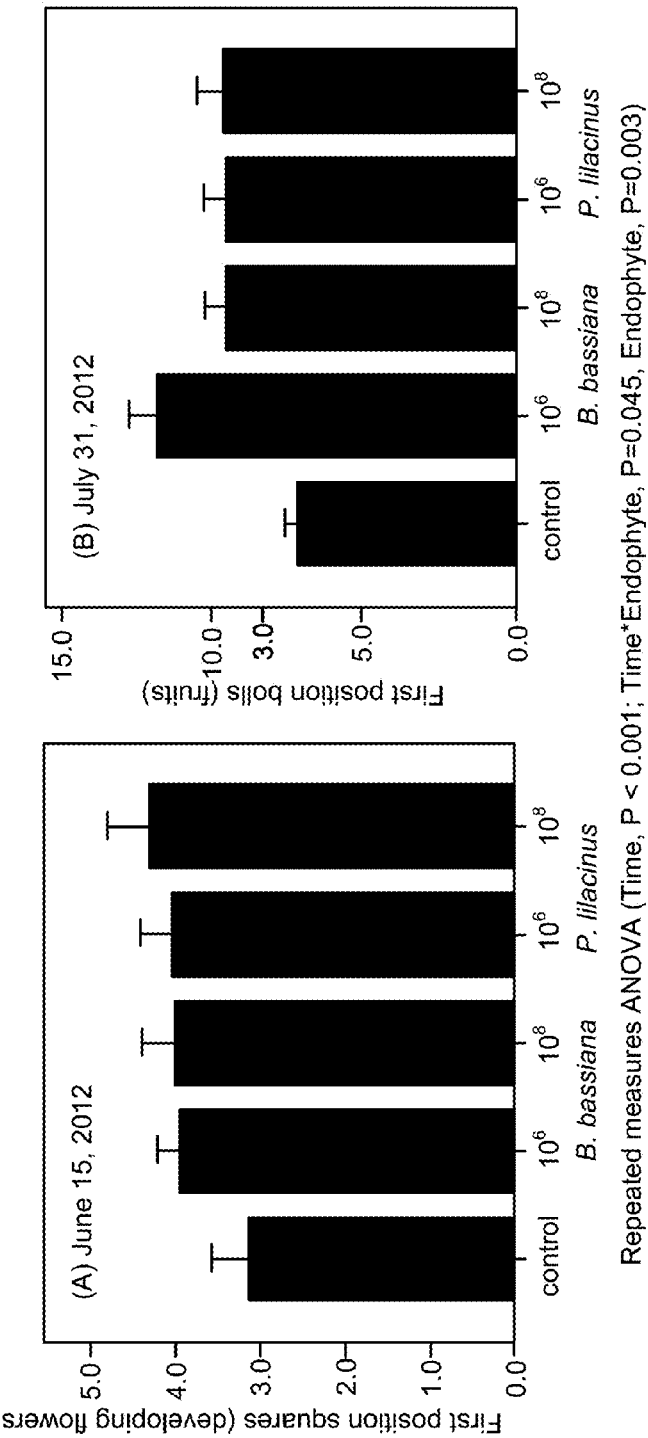
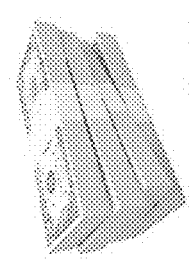
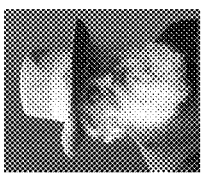
FIG. 10

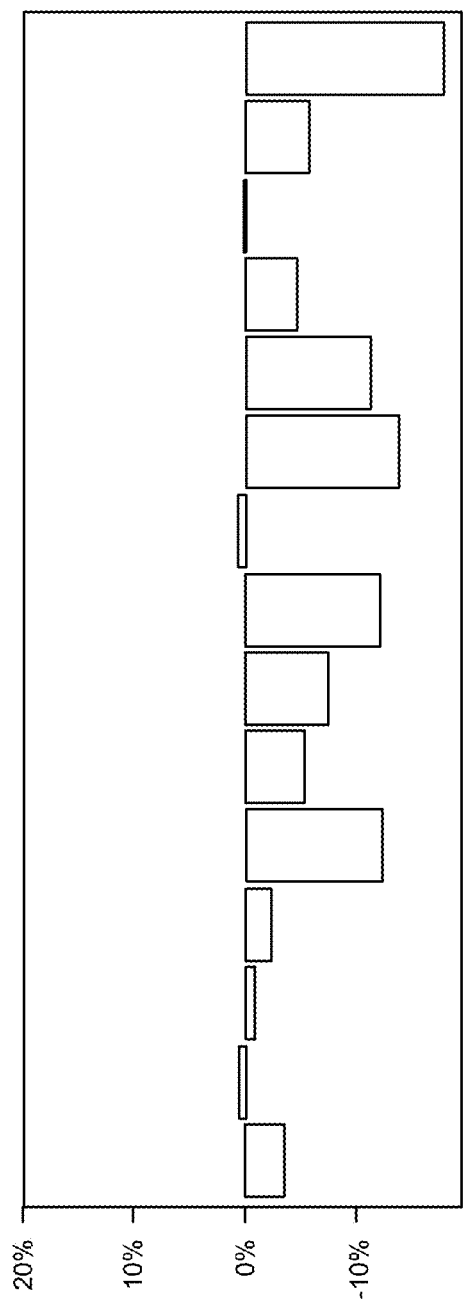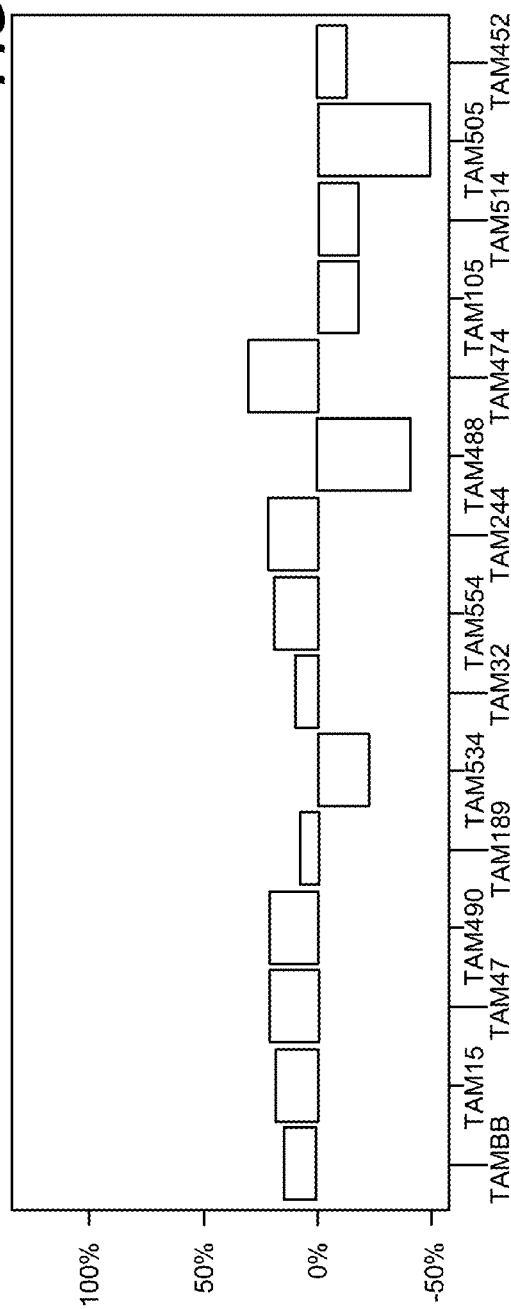

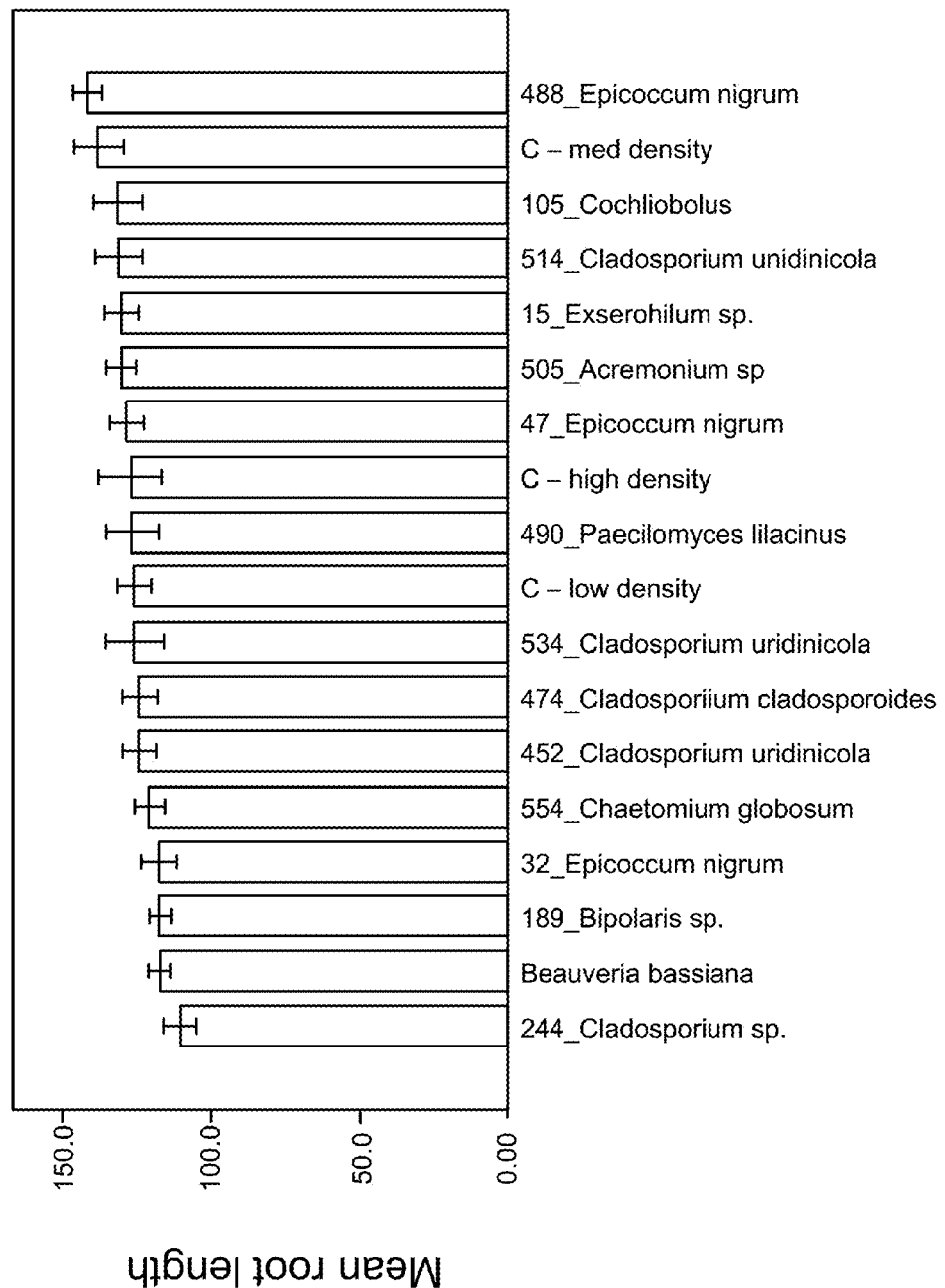

| Genotype | Treatments | Estimate | Std. Error |
|---|---|---|---|
| DTP | 194/Epic | 15.000 | .323 |
|  | 249/Clad | 15.778 | .173 |
|  | 355/Chae | 16.500 | .345 |
|  | 46/Epico | 17.125 | .364 |
|  | 463/Clad | 16.571 | .291 |
|  | 534/Clad | 15.722 | .289 |
|  | 554/Chae | 15.571 | .272 |
|  | 58/Epico | 15.438 | .433 |
|  | control | 16.000 | .296 |
|  | Overall | 15.952 | .116 |
| PHY | 194/Epic | 15.706 | .329 |
|  | 249/Clad | 15.000 | .331 |
|  | 355/Chae | 14.471 | .194 |
|  | 46/Epico | 18.000 | .257 |
|  | 463/Clad | 15.438 | .288 |
|  | 534/Clad | 14.333 | .347 |
|  | 554/Chae | 16.294 | .254 |
|  | 58/Epico | 14.824 | .376 |
|  | control | 16.722 | .289 |
|  | Overall | 15.682 | .135 |
| Overall | Overall | 15.816 | .089 |

*FIG. 24*

| Genotype | Treatments | Estimate | Std. Error |
|---|---|---|---|
| DTP | 194 | 18.899 | .332 |
| | 249 | 19.000 | .370 |
| | 355 | 19.389 | .244 |
| | 46 | 20.188 | .248 |
| | 463 | 19.357 | .289 |
| | 534 | 19.444 | .258 |
| | 554 | 19.429 | .374 |
| | 58 | 19.563 | .343 |
| | control | 20.286 | .294 |
| | Overall | 19.479 | .107 |
| PHY | 194 | 19.176 | .246 |
| | 249 | 18.357 | .341 |
| | 355 | 17.647 | .363 |
| | 46 | 20.353 | .171 |
| | 463 | 19.125 | .340 |
| | 534 | 18.200 | .279 |
| | 554 | 19.529 | .244 |
| | 58 | 19.706 | .319 |
| | control | 19.667 | .354 |
| | Overall | 19.115 | .118 |
| Overall | Overall | 19.296 | .080 |

*FIG. 25*

SEQUENCE LISTING

<160> NUMBER OF SEQ ID NOS: 77

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

```
<400> SEQUENCE: 1
cggcggactc gccccagccc g                                              21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
ccgcgtcggg gttccggtgc g                                              21

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ctcagttgcc tcggcgggaa                                                20

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
gtgcaactca gagaagaaat tccg                                           24

<210> SEQ ID NO 5
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 5
tccgtaggtg aacctgcg                                                  18

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
gctgcgttct tcatcgatgc                                                20

<210> SEQ ID NO 7
<211> LENGTH: 225
<212> TYPE: DNA
<213> ORGANISM: Acremonium alternatum

<400> SEQUENCE: 7
gggtacataa actcccaaac cattgtgaac ttaccactgt tgcttcggcg gcctcgcccc     60
gggcgcgttc gcgcggcccg gacccaggcg tccgccggag gctccaaact cttgtctttt    120
agtgtatttc tgagtggcat aagcaaataa atcaaaactt tcagcaacgg atctcttggt    180
tctggcatcg atgaagaacg cagcaggact aacgtgtgtc gacgg                   225
```

<210> SEQ ID NO 8
<211> LENGTH: 225
<212> TYPE: DNA
<213> ORGANISM: Alternaria alternata

<400> SEQUENCE: 8

```
gccaatgaac acctgcggag ggatcattac acaaatatga aggcgggctg gacctctcgg      60
ggttacagcc ttgctgaata atccccttg tcttttgcgt acttcttgtt tccttggtgg     120
gttcgcccac cactaggaca aacataaacc ttttgtaatt gcaatcagcg tcagtaacaa    180
attaataatt acaactttca acaacggatc tcttggttct ggcat                     225
```

<210> SEQ ID NO 9
<211> LENGTH: 240
<212> TYPE: DNA
<213> ORGANISM: Alternaria brassicae

<400> SEQUENCE: 9

```
gactttcata gtaggaggag cgggctggaa tcaccctctc gggggtaca gccttgctga       60
attatttcac ccttgtcttt tgcgtacttc ttgtttcctt ggtgggttcg cccaccacta     120
ggacaaacat aaaccttttg taattgcaat cagcgtcagt aacaaattaa taattacaac    180
tttcaacaac ggatctcttg ttctggcat cgatgaagaa cgcacagtca gtgtgaaatc      240
```

<210> SEQ ID NO 10
<211> LENGTH: 224
<212> TYPE: DNA
<213> ORGANISM: Alternaria compacta

<400> SEQUENCE: 10

```
tgcgtatgtc cgacatatca ggcgggctgg acctctcggg gttacagcct tgctgaatta      60
ttcaccccctt gtcttttgcg tacttcttgt tccttggtg ggttcgccca ccactaggac    120
aaacataaac cttttgtaat tgcaatcagc gtcagtaaca aattaataat tacaactttc   180
aacaacggat ctcttggttc tggcatcgat gaaaaacgca tcaa                       224
```

<210> SEQ ID NO 11
<211> LENGTH: 297
<212> TYPE: DNA
<213> ORGANISM: Alternaria dianthi

<400> SEQUENCE: 11

```
cctccggact ggctcgagga ggttggcaac gaccacctca agccggaaag ttggtcaaac       60
tcggtcattt agaggaagta aaagtcgtaa caatttctcc gtaggtgaac ctgcggaggg     120
atcattacac aggtatgaag gcgggctgga atctctcggg ttacagcct tgctgaatta     180
ttcacccgtg tcttttgcgt acttcttgtt cctgggtgg gttcgcccac caccaggacc     240
aaccataaac cttttgtaat tgcaatcagc gtcagtaaca aataataat tacaact        297
```

<210> SEQ ID NO 12
<211> LENGTH: 249
<212> TYPE: DNA
<213> ORGANISM: Alternaria longipes

<400> SEQUENCE: 12

```
tggtaattac aaaatgaagc gggctggacc tctcggggtt acagcctgct gaattattca      60
cccttgtctt tgcgtactt cttgtttcct tggtgggttc gcccaccact aggacaaaca    120
```

```
taaaccttttt gtaattgcaa tcagcgtcag taacaaatta ataattacaa ctttcaacaa    180
cggatctctt ggttctggca tcgatgaaga acgcagcaaa ttaatgccgg ctggaacgcc    240
tctgggata                                                              249
```

<210> SEQ ID NO 13
<211> LENGTH: 227
<212> TYPE: DNA
<213> ORGANISM: Alternaria mali

<400> SEQUENCE: 13

```
atcgtggagg tcaggactat tacacatatg aaggcgggct ggaacctctc ggggttacag     60
ccttgctgaa ttattcaccc ttgtcttttg cgtacttctt gtttccttgg tgggttcgcc    120
caccactagg acaaacataa acctttgta attgcaatca gcgtcagtaa caaattaata    180
attacaactt tccacaacgg gatctcttgg gttctggcat cgctagc                  227
```

<210> SEQ ID NO 14
<211> LENGTH: 210
<212> TYPE: DNA
<213> ORGANISM: Alternaria sesami

<400> SEQUENCE: 14

```
aggcgggctg gcacctctcg gggtggccag ccttgctgaa ttattccacc cgtgtctttt     60
gcgtacttct tgtttccttg gtgggctcgc ccaccacaag gaccaaccca taaacctttt    120
tgtaatggca atcagcgtca gtaacaatgt aataattaca actttcaaca acggatctct    180
tggttctggc atcgatgaag aacgcagcaa                                     210
```

<210> SEQ ID NO 15
<211> LENGTH: 256
<212> TYPE: DNA
<213> ORGANISM: Alternaria solani

<400> SEQUENCE: 15

```
atgtgtcatg gtatgaggcg ggctggacct ctcggggtta cagccttgct gaattattca     60
cccttgtctt ttgcgtactt cttgtttcct tggtgggttc gcccaccact aggacaaaca    120 taaaccttttt gtaattgcaa tcagcgtcag taacaaatta ataattacaa ctttcaacaa    180
cggatctctt ggttctggca tcgatgaaga acgcagcgaa atgcgataag tagtgtgaat    240
tgcagaattc agtaat                                                    256
```

<210> SEQ ID NO 16
<211> LENGTH: 263
<212> TYPE: DNA
<213> ORGANISM: Alternaria sp.

<400> SEQUENCE: 16

```
aggcgggctg gacctctcgg ggttacagcc ttgctgaatt attcacccttt gtcttttgcg     60 tacttcttgt tccttggtg ggttcgccca ccactaggac aaacataaac cttttgtaat    120
tgcaatcagc gtcagtaaca aattaataat tacaactttc aacaacggat ctcttggttc    180
tggcatcgat gaagaacgca gctaaataca tatgaaggcg ggctggaacg tcccgcggtt    240
gcagacttgc tgacttattc acc                                            263
```

<210> SEQ ID NO 17
<211> LENGTH: 204
<212> TYPE: DNA
<213> ORGANISM: Alternaria tenuissima

```
<400> SEQUENCE: 17
tgaggcgggc tggacctctc ggggttacag ccttgctgaa ttattcaccc ttgtcttttg      60
cgtacttctt gtttccttgg tgggttcgcc caccactagg acaaacataa accttttgta    120
attgcaatca gcgtcagtaa caaattaata attacaactt tcaacaacgg atctcttggt    180
tctggcatcg atgaagaacg cagc                                            204

<210> SEQ ID NO 18
<211> LENGTH: 244
<212> TYPE: DNA
<213> ORGANISM: Bipolaris spicifera

<400> SEQUENCE: 18
acgaaggccg ttcgcggctg gactatttat taccccttgtc ttttgcgcac ttgttgtttc     60
```

```
acgaaggccg ttcgcggctg gactatttat taccccttgtc ttttgcgcac ttgttgtttc     60
ctgggcgggt tcgctcgcca ccaggaccac aatataaacc ttttttatgc agttgcaatc    120
agcgtcagta taacaaatgt aaatcattta caactttcaa caacggatct cttggttctg    180
gcatcgatga agaacgcagc aatacacact caataaaaaa cgaaggccgt tcgcggacgg    240
acta                                                                  244

<210> SEQ ID NO 19
<211> LENGTH: 246
<212> TYPE: DNA
<213> ORGANISM: Cercospora canescens

<400> SEQUENCE: 19
cttcggtgcg cttccccttt ggggactttt gggagggatc attactgagt gagggccttc     60
gggctcgacc tccaaccctt tgtgaacaca acttgttgct tcgggggcga ccctgccgtt    120
tcgacggcga gcgcccccgg aggccttcaa acactgcatc tttgcgtcgg agtttaagta    180
aattaaacaa aactttcaac aacggatctc ttggttctgg catcgatgaa gaacgcagcg    240
aaatgc                                                                246

<210> SEQ ID NO 20
<211> LENGTH: 280
<212> TYPE: DNA
<213> ORGANISM: Cercospora capsici

<400> SEQUENCE: 20
gactagctac ataggcttcg ggctcgacct ccacccttg tgaacacaac ttgttgcttc     60
gggggcgacc ctgccgtttc gacggcgagc gcccccggag gccttcaaac actgcatctt    120
tgcgtcggag tttaagtaaa ttaaacaaaa cttttcaacaa cggatctctt ggttctggca    180
tcgatgaaga acgcagcaga aatgcgataa gtaatgtgaa ttgcagaatt cagtgaatca    240
tcgaatcttt gaacgcacat tgcgcccctt ggtattccga                            280

<210> SEQ ID NO 21
<211> LENGTH: 220
<212> TYPE: DNA
<213> ORGANISM: Cercospora kikuchii

<400> SEQUENCE: 21
cgtagggtga acctgcggag ggatcattac tgagtgaggg ccttcgggct cgacctccaa     60 cccctttgtga acacaacttg ttgcttcggg ggcgaccctg ccgtttcgac ggcgagcgcc    120
cccggaggcc ttcaaacact gcatctttgc gtcggagttt aagtaaatta aacaaaactt    180
```
tcaacaacgg atctcttggt tctggcatcg atgaagaacg                                                220

<210> SEQ ID NO 22
<211> LENGTH: 243
<212> TYPE: DNA
<213> ORGANISM: Cercospora zinnia

<400> SEQUENCE: 22
tcgattgaat ggctcagtga ggccttcgga ctggcccagg gaggtcggca acgaccaccc              60
agggccggaa agttggtcaa actcggtcat ttagaggaag taaaagtcgt aacaaggtct            120
ccgtaggtga acctgcggag ggatcattac tgagtgaggg ccttcgggct cgacctccaa            180
ccctttgtga acacaacttg ttgcttcggg ggcgaccctg ccgtttcgac ggcgatcact            240
tgt                                                                          243

<210> SEQ ID NO 23
<211> LENGTH: 291
<212> TYPE: DNA
<213> ORGANISM: Chaetomium globosum

<400> SEQUENCE: 23
aaactcccta accattgtga acgttaccta taccgttgct tcggcgggcg ccccggggt              60
ttaccccccg ggcgcccctg ggccccaccg cgggcgcccg ccggaggtca ccaaactctt            120
gataatttat ggcctctctg agtcttctgt actgaataag tcaaaacttt caacaacgga            180
tctcttggtt ctggcatcga tgaagaacgc agccatcatt agagagttgc aaactcccta            240
aaccccttgtg aacgtaaccct ataccgttgc gttcggcggg cggccccggg g                   291

<210> SEQ ID NO 24
<211> LENGTH: 263
<212> TYPE: DNA
<213> ORGANISM: Chaetomium piluliferum

<400> SEQUENCE: 24
cattacagag ttgcaaaact ccctaaaacca ttgtgaacgt taccttcaaa ccgttgcttc            60
ggcgggcggc cccgctccgc ccggtgcccc ctggcccccct agcggggcgc cgccggaggg           120
aaaacccaac tcttgattat aatggcctct ctgtctcttc tgtactgaat aagtcaaaac            180
tttcaacaac ggatctcttg gttctggcat cgatgaagaa cgcagcgaaa tgcgataagt            240
aatgtgaatt gcagaattca gtg                                                    263

<210> SEQ ID NO 25
<211> LENGTH: 210
<212> TYPE: DNA
<213> ORGANISM: Chaetomium sp.

<400> SEQUENCE: 25
ctccctaacc attgtgaacg ttacctaaac cgttgcttcg gcgggcgccc cggggttta             60
cccccgggc gccctgggc ccaccgcgg gcgcccgccg gaggtcacca aactcttgat              120
aatttatggc ctctctgagt cttctgtact gaataagtca aaactttcaa caacggatct            180
cttggttctg gcatcgatga aaaacgcagc                                             210

<210> SEQ ID NO 26
<211> LENGTH: 255
<212> TYPE: DNA
<213> ORGANISM: Cladosporium cladosporioides

<400> SEQUENCE: 26

```
tctaccaccg ggatgttcat aacccttttgt tgtccgactc tgttgcctcc ggggcgaccc      60
tgccttcggg cggggggctcc gggtggacac ttcaaactct tgcgtaactt tgcagtctga    120
gtaaatttaa ttaataaatt aaaactttta acaacggatc tcttggttct ggcatcgatg    180
aagaacgcag ccaaaccagc aaacccggtc taaccccccgg gatgttcatg accctttgtt   240
gtccgactct gaggc                                                     255

<210> SEQ ID NO 27
<211> LENGTH: 240
<212> TYPE: DNA
<213> ORGANISM: Cladosporium sp.

<400> SEQUENCE: 27
actgcttcat tacaacaacg cccgggcttc ggcctggtta ttcaaaaccc tttgttgtcc      60
gactctgttg cctccgcggc gaccctgcct tcgggcgggg gctccgggtg gacacttcaa    120
actcttgcgt aactttgcag tctgagtaaa cttaattaat aaattaaaac ttttaacaac    180
ggatctcttg gttctggcat cgatgaagaa cggagcgaaa tgcgataagt aatgaattgc    240

<210> SEQ ID NO 28
<211> LENGTH: 226
<212> TYPE: DNA
<213> ORGANISM: Cladosporium uredinicola

<400> SEQUENCE: 28
ggtctaccac cgggatgttc ataacccttt gttgtccgac tctgttgcct ccggggcgac      60
cctgccttcg gcggggggct ccgggtggac acttcaaact cttgcgtaac tttgcagtct    120
gagtaaactt aattaataaa ttaaaacttt taacaacgga tctcttggtt ctggcatcga    180
tgaagaacgc agcgaaaatc aagtgggtct gcccccgcga tgggat                  226

<210> SEQ ID NO 29
<211> LENGTH: 250
<212> TYPE: DNA
<213> ORGANISM: Cochliobolus sp

<400> SEQUENCE: 29
gctaattaac caataaccta tgaaggctgt acgccgctgc gccccggcc agttggctga       60 ggctggatta tttattaccc cttgtctttt gcgcacttg tgtttcctgg gcggttcgc      120 ccgcctccag gaccacacca taaaccttt ttatgcagtt gcaatcagcg tcagtacaac     180 aaaatgtaaat catttacaac tttcaacaac ggatctcttg gttctggcat cgatgaagaa   240
ccgcaacagc                                                           250

<210> SEQ ID NO 30
<211> LENGTH: 249
<212> TYPE: DNA
<213> ORGANISM: Phanerochaete crassa

<400> SEQUENCE: 30
ggttgtagct ggcctcatac tgggcatgtg cacacctggc tcatccactc cttaacctct      60
gtgcactttt tgtaggctct ggttgaaagg cgttgcttca cttcggtgtg gtaatcgctg    120
gaagacctgg tctatgtttt attacaaacg cttcagttat acaatgttta tctgcgtata    180
acgcatttat atacaacttt cagcaacgga tctcttggct ctcgcatcga tgaagaacgc    240
agctcgagt                                                           249
```

<210> SEQ ID NO 31
<211> LENGTH: 267
<212> TYPE: DNA
<213> ORGANISM: Phoma americana

<400> SEQUENCE: 31

```
cgtacgctac atggaagtaa agtagtaac aaggtttccg taggtgaacc tgcggaagga      60
tcattaccta gagttgtagg ctttgcctgc tatctcttac ccatgtcttt tgagtacctt    120
cgtttcctcg gcgggtccgc cgccgattg gacaatttaa accatttgca gttgcaatca    180
gcgtctgaaa aaacttaata gttacaactt tcaacaacgg atctcttggt tctggcatca    240
atgaaaaacg cagcaacaca aaattac                                        267
```

<210> SEQ ID NO 32
<211> LENGTH: 205
<212> TYPE: DNA
<213> ORGANISM: Phoma subherbarum

<400> SEQUENCE: 32

```
tacgtgcagc gctttgcctg ctatctctta cccatgtctt ttgagtacct tcgtttcctc     60
ggcgggtccg cccgccgatt ggacaattta aaccatttgc agttgcaatc agcgtctgaa    120
aaaaacttaa tagttacaac tttcaacaac ggatctcttg gttctggcat cgatgaagaa    180
cgcagcttac ctagagaatg cgtgt                                          205
```

<210> SEQ ID NO 33
<211> LENGTH: 264
<212> TYPE: DNA
<213> ORGANISM: Phomopsis liquidambari

<400> SEQUENCE: 33

```
aggcgcaccc agaaaccctt gtgaactta taccttactg ttgcctcggc gcatgctggc     60
cccctcgggg tccctggag acagggagca ggcacgccgg cggccaagtt aactcttgtt    120
tttacactga aactctgaga aaaaaacaca atgaatcaa actttcaac aacggatctc    180 ttggttctgg catcgatgaa gaacgcacaa gtggagggcc ccaggcgccc cccaaaacc    240 tttttttgagt tattacttac tgtt                                          264
```

<210> SEQ ID NO 34
<211> LENGTH: 222
<212> TYPE: DNA
<213> ORGANISM: Phomopsis sp.

<400> SEQUENCE: 34

```
ccggcgcacc cagaaaccct tgtgaactt atacctactg ttgcctcggc gcaggccggc     60
cttttgtcaa aaaaggcccc ctggagacag ggagcagccc gccggcggcc aaccaaactc    120
ttgtttctac agtgaatctc tgaggaaaaa acataaatga atcaaaactt tcaacaacgg    180
atctcttggt tctggcatcg atgaagaacg cagcatgctg gc                       222
```

<210> SEQ ID NO 35
<211> LENGTH: 255
<212> TYPE: DNA
<213> ORGANISM: Pleospora sp.

<400> SEQUENCE: 35

```
cgggttggga cctcacctcg gtgagggctc cagcttgtct gaattattca cccatgtctt     60
ttgcgcactt cttgtttcct gggcgggttc gcccgccacc aggaccaaac cataaacctt    120
```

```
tttgtaattg caatcagcgt cagtaaacaa tgtaattatt acaactttca acaacggatc    180
tcttggttct ggcatcgatg aagaacgcag cgaaatgcga tacgtagtgt gaattgcaga    240
attcagtgat tttgc                                                    255
```

```
<210> SEQ ID NO 36
<211> LENGTH: 349
<212> TYPE: DNA
<213> ORGANISM: Pleosporaceae sp.

<400> SEQUENCE: 36
ggatcattac acaatatgaa ggcgggctgg aacctctcgg ggttacagcc ttgctgaatt     60
attcacccct gtcttttgcg tacttcttgt ttccttggtg ggttcgccca ccactaggac    120
aaacataaac cttttgtaat tgcaatcagc gtcagtaaca aattaataat taccactttc    180
aacaacggga tctcttggtt ctgggcatcg agcagaaaaa cgcagaattg aaggcgggct    240
gggaacctct cggggggggt ccagggcttt ggtgaattat tcaccccttg cctttgcgta    300
cgttgtttgt tttccttggg ggggtaggc acacaaaaaa agaaaacgg              349
```

```
<210> SEQ ID NO 37
<211> LENGTH: 222
<212> TYPE: DNA
<213> ORGANISM: Preussia africana

<400> SEQUENCE: 37
aagtaccatt atcgtagggc ttcggccctg tcgagataga acccttgcct ttttgagtac     60
cttttcgttt cctcggcagg ctcgcctgcc aatggggacc ccaacaaaca ctttgcagta    120
cctgtaaaca gtctgaacaa acttttaaaa attaaaactt tcaacaacgg atctcttggt    180
tctggcatcg atgaagaacg cagcgaaatg cgataaaacg tg                      222
```

```
<210> SEQ ID NO 38
<211> LENGTH: 218
<212> TYPE: DNA
<213> ORGANISM: Preussia sp.

<400> SEQUENCE: 38
ttcgagatac acccttgcct ttttgagtac cttttcgttt cctcggcagg ctcgcctgcc     60
aacggggacc cttcaaaacg ctttgtaata cctgtaactg tctgatataa caagcaaaaa    120
tcaaaacttt caacaacgga tctcttggtt ctggcatcga tgaagaacgc agcaatcgtt    180
gggcttcggc ccattagaga taacacccct gcctttttt                          218
```

```
<210> SEQ ID NO 39
<211> LENGTH: 254
<212> TYPE: DNA
<213> ORGANISM: Pseudozyma sp.

<400> SEQUENCE: 39
acatctcgcg gttcagcctt gttgagtatt caccccttgtt ttttgcggag aaatgtttgg    60
gtggagggag caccagcacc aagacaaatc taaacctttt gcaattgcaa tacgggcgac    120 atttaccttta ataattgttg atttcataag attatatctt ggttgaaact ccactggtaa   180
tgccatcgtc taaaatctaa aaacaacttt tggcaacgga tctcttggtt ctcgcatcga   240
tgaagaacgc agcc                                                     254
```

```
<210> SEQ ID NO 40
```

```
<211> LENGTH: 277
<212> TYPE: DNA
<213> ORGANISM: Pyrenophora teres

<400> SEQUENCE: 40
aggcagattg ggtagtcccc gcttttgggg tttgcccatt ctggcgccat attcacccat      60
gtcttttgcg tactacttgt ttccttggcg ggttcgcccg ccaattggac tttattcaac     120
ccttttttt ttattgcaat cagcgtcagc aaaacaatgt aatcaattta caactttcaa     180
caacggatct cttggttctg gcatcgatga aaaacgcagc cacaatatga tggccgatgg     240
ggcaggcctc ttttggggtt gccccctctg gcgccct                              277

<210> SEQ ID NO 41
<211> LENGTH: 289
<212> TYPE: DNA
<213> ORGANISM: Colletotrichum capsici

<400> SEQUENCE: 41
gctcatcacc ctttgtgaca taccttaact gttgcttcgg cgggtaggcg tcccctgaaa      60
aggacgtctc ccggccctct cccgtccgcg ggtggggcgc ccgccggagg ataaccaaac     120
tctgatttaa cgacgtttct tctgagtgac acaagcaaat aatcaaaact tttaacaacg     180
gatctcttgg ttctggcatc gatgaagaac gcagcaatta ttggggtgtt gctcatcatc     240
ctttgtggtg aaccttaact gttgctgcgg cgggggggcgg cgtcccctg                289

<210> SEQ ID NO 42
<211> LENGTH: 216
<212> TYPE: DNA
<213> ORGANISM: Coniolariella gamsii

<400> SEQUENCE: 42
tgacactccc aaaacccctg tgaacatacc gtacgttgcc tcggcggggg ggcgctcccc      60
ccccgccggc ggcccacgaa actctgttttt gccctgaatc tctgaaacga caaactaaat    120
cagttaaaac tttcaacaac ggatctcttg gttctggcat cgatgaagaa cgcagcgaaa    180
tatagaagtg acccaactcc taaccactgt gaacaa                               216

<210> SEQ ID NO 43
<211> LENGTH: 268
<212> TYPE: DNA
<213> ORGANISM: Coniothyrium aleuritis

<400> SEQUENCE: 43
tagacttcac taaagcttgt agacttcggt ctgctacctc ttacccatgt cttttgagta      60
ccttcgtttc ctcggcgggt ccgccgccg attggacaac attcaaaccc tttgcagttg     120
caatcagcgt ctgaaaaaac ataatagtta caactttcaa caacggatct cttggttctg    180
gcatcgatga agaacgcagc gaaatgcgat aagtagtgtg aattgcagaa ttcagtgaat    240
catcgaatct ttgaacgcac attgcgcc                                        268

<210> SEQ ID NO 44
<211> LENGTH: 210
<212> TYPE: DNA
<213> ORGANISM: Coniothyrium sp.

<400> SEQUENCE: 44
gggctggatc tctcggggtt acagccttgc tgaattattc acccttgtct tttgcgtact      60
tcttgtttcc ttggtgggtt cgcccaccac taggacaaac ataaaccttt tgtaattgca     120
```

```
atcagcgtca gtaacaaatt aataattaca actttcaaca acggatctct tggttctggc    180
atcgatgaag aacgcagcaa cactaatatg                                     210

<210> SEQ ID NO 45
<211> LENGTH: 218
<212> TYPE: DNA
<213> ORGANISM: Corynespora cassiicola

<400> SEQUENCE: 45
cgccccttcg agatagcacc ctttgtttat gagcacctct cgtttcctcg gcaggctcgc     60
ctgccaacgg ggacccacca caaacccatt gtagtacaag aagtacacgt ctgaacaaaa    120
caaaacaaac tatttacaac tttcaacaac ggatctcttg gttctggcat cgatgaagaa    180
cgcagcggat atcgtagggg ccgcgccccc ttccagat                            218

<210> SEQ ID NO 46
<211> LENGTH: 204
<212> TYPE: DNA
<213> ORGANISM: Diaporthe sp.

<400> SEQUENCE: 46 acccttgtg aacttatacc taccgttgcc tcggcgcagg ccggcccccc tcaccggggg      60
ccccccggag acggggagca gcccgccggc ggccaaccaa actcttgttt cttagtgaat    120
ctctgagtaa aaatcataaa tgaatcaaaa ctttcaacaa cggatctctt ggttctggca    180
tcgatgaaga acgcagcaag ttgc                                           204

<210> SEQ ID NO 47
<211> LENGTH: 281
<212> TYPE: DNA
<213> ORGANISM: Diatrype sp.

<400> SEQUENCE: 47
ccatgtgaac ttacctttgt tgcctcggcg ggagagccta cccggtacct accctgtagt     60
tacccgggag cgagctaccc tgtagcccgc tgctggccga cccgccggtg gacagtaaaa    120
ctcttgtttt ttagtgatta tctgagtgtt tatacttaat aagttaaaac tttcaacaac    180
ggatctcttg gttctggcat cgatgaagaa cgcagccaat acagagttat cttctcccag    240
cccatgtgaa cttacctttg ttgccccggc gggagagcct a                        281

<210> SEQ ID NO 48
<211> LENGTH: 338
<212> TYPE: DNA
<213> ORGANISM: Drechslerella dactyloides

<400> SEQUENCE: 48
ggttagaaac tgttgtttcg gcgggatctc tgccccgggg gcgtcgcagc cccggaccaa     60 ggggccgcc ggaggaccaa ccaaaactct ttttgtatac cccctcgcgg ttttttttta    120
taatctgagc cttctcggcg cctctcgtag gcgtttcgaa aatgaatcaa aacttttaaa    180
aacggatctc ttggttctgg catcggatga agaacgcaga gaaatgcgat aagtaatgtg    240
aattgcagaa ttcactgaat catctaatct ttgaacggac attgcgcccg ccagttttct    300
ggcgggcatg cctgtccgag cgtcatttca accctcga                            338

<210> SEQ ID NO 49
<211> LENGTH: 247
<212> TYPE: DNA
```

<213> ORGANISM: Embellisia indefessa

<400> SEQUENCE: 49

| gcatcgatac ctgatccgag gtcaaaagtt gaaaaaaggc tttgtggatg ctgaccttgg | 60 |
|---|---|
| ctggaagaga gcgcgacttg tgctgcgctc cgaaaccagt aggccggctg caatgacttt | 120 |
| aaggcgagtc tccagcgaac tggagacaag acgcccaaca ccaagcaaag cttgagggta | 180 |
| caaatgacgc tcgaacaggc atgccctttg aataccaaa gggcgcaatg tgcgttcaaa | 240 |
| aaaagca | 247 |

<210> SEQ ID NO 50
<211> LENGTH: 207
<212> TYPE: DNA
<213> ORGANISM: Epicoccum nigrum

<400> SEQUENCE: 50

| ttgtagactt cggtctgcta cctcttaccc atgtcttttg agtaccttcg tttcctcggc | 60 |
|---|---|
| gggtccgccc gccgattgga caacattcaa acccttgca gttgcaatca gcgtctgaaa | 120 |
| aaacataata gttacaactt tcaacaacgg atctcttggt tctggcatcg atgaaaaacg | 180 |
| catcacctag agtttgtaga cttcggt | 207 |

<210> SEQ ID NO 51
<211> LENGTH: 234
<212> TYPE: DNA
<213> ORGANISM: Epicoccum sp.

<400> SEQUENCE: 51

| gtacttacct acgatttgtg gagttcggtc tgctacctct tacccatgtc tttttaagta | 60 |
|---|---|
| ccttcgtttc ctcggcgggt ccgcccgccg gttggacaac attcaaaccc tttgcagttg | 120 |
| caatcagcgt ctgaaaaaac ttaatagtta caactttcaa caacggatct cttggttctg | 180 |
| gcatcgaaca caaacgcagc agcttttagg gacctaccgt ctcctcctct tacc | 234 |

<210> SEQ ID NO 52
<211> LENGTH: 237
<212> TYPE: DNA
<213> ORGANISM: Exserohilum rostratum

<400> SEQUENCE: 52

| gctaatttcc ccaccaaact tgtagggtgt ggtttgctgg caacagcgaa ccgccccaag | 60 |
|---|---|
| tattttttcac ccatgtcttt tgcgcacttt ttgtttcctg gccagttcg ctcgccacca | 120 |
| ggacccaacc ataaacctttt ttttatgcag ttgcaatcag cgtcagtata ataattcaat | 180 |
| ttattaaaac tttcaacaac ggatctcttg gttctggcat cgatgaagaa cgcacaa | 237 |

<210> SEQ ID NO 53
<211> LENGTH: 223
<212> TYPE: DNA
<213> ORGANISM: Fusarium chlamydosporum

<400> SEQUENCE: 53

| tcccaaccc tgtgacatac ctatacgttg cctcggcgga tcagcccgcg ccccgtaaaa | 60 |
|---|---|
| cgggacggcc cgcccgagga cccctaaact ctgttttag tggaacttct gagtaaaaca | 120 |
| aacaaataaa tcaaaacttt caacaacgga tctcttggtt ctggcatcga tgaagaacgc | 180 |
| agctcgatga agaacgcagc cccctcccca cgggtgggaa cat | 223 |

<210> SEQ ID NO 54
<211> LENGTH: 258
<212> TYPE: DNA
<213> ORGANISM: Fusarium sp.

<400> SEQUENCE: 54

```
cactcccaac ccatgtgaac ttatctcttt gttgcctcgg cgcaagctac ccgggacctc      60
gcgccccggg cggcccgccg gcggacaaac caaactctgt tatcttagtt gattatctga     120
gtgtcttatt taataagtca aaactttcaa caacggatct cttggttctg gcatcgatga     180
agaacgcagc aaatcattac agaattatcc aactcccaaa cccatgtgaa ctttttctttt    240
tgttgcctcg gcgcaagc                                                   258
```

<210> SEQ ID NO 55
<211> LENGTH: 236
<212> TYPE: DNA
<213> ORGANISM: Gibellulopsis nigrescens

<400> SEQUENCE: 55

```
atactcataa ccctttgtga ccttcatacc tgttgcttcg gcggcgcgcc tctcggggcg      60
tgcccgccgg cattatcaga atctctgttc gaacccgacg atacttctga gtgttctaag    120
cgaactgtta aaactttcaa caacggatct cttggctcca gcatcgatga agaacgcagc    180
aaatgagggg tactactctc accccccttt ggcctcttcc cacttgttgc ttcggc        236
```

<210> SEQ ID NO 56
<211> LENGTH: 243
<212> TYPE: DNA
<213> ORGANISM: Gnomoniopsis sp.

<400> SEQUENCE: 56

```
cgggtgctac ccagaaaccc tttgtgaatt attctcattg ttgcctcggc attgactggc      60
ctcttctgga ggtccctttt ccttcgggga aaggagcagg tcggccggtg ccctataaa     120
ctctttgttt ttacagtgta tcttctgagt aaacaactat aaatgaatca aaactttttaa   180
caacggatct cttggttctg gcatcgatga agaacgcagc aatggaacaa acgccctccg    240
ggg                                                                  243
```

<210> SEQ ID NO 57
<211> LENGTH: 251
<212> TYPE: DNA
<213> ORGANISM: Lewia infectoria

<400> SEQUENCE: 57

```
gcgggctgga caccccagc cgggcactgc ttcacggcgt gcgcggctgg gccggccctg      60
ctgaattatt caccgtgtc ttttgcgtac ttccttgtttc ctgggtgggc tcgcccgcca    120
tcaggaccaa ccacaaacct tttgcaatag caatcacggt cagtaacaac gtaattaatt   180
acaactttca acaacggatc tcttggttct ggcatcgatg aagaacgtag cgaaatgcga    240
tacgtagtgt g                                                         251
```

<210> SEQ ID NO 58
<211> LENGTH: 210
<212> TYPE: DNA
<213> ORGANISM: Mycosphaerella coffeicola

<400> SEQUENCE: 58

```
aagtcgtact ggcttcgggc tcgacctcca ccctttgtga acacaacttg ttgcttcggg     60
```

```
ggcgaccctg ccgtttcgac ggcgagcgcc cccggaggcc ttcaaacact gcatctttgc      120
gtcggagttt aagtaaatta acaaaaactt tcaacaacgg atctcttggt tctggcatcg      180
atgaagaacg cagcggtctg cacacatcag                                       210
```

<210> SEQ ID NO 59
<211> LENGTH: 213
<212> TYPE: DNA
<213> ORGANISM: Mycosphaerellaceae sp.

<400> SEQUENCE: 59

```
gaccacggcc ggccgcgcca gcgataatcc tttgtgcccc gacattgttg cctgccttt       60 gaccctgcct tggggcgggg gctccgggtg gacacttaaa ctcttgcgta actttgcagt      120
ctgagtaaac ttaattaata aattaaaact tttaacaccg gatctcttgg ttctggcatc      180
gatgacaaaa cgcaacaaac gcagcagtta acc                                   213
```

<210> SEQ ID NO 60
<211> LENGTH: 227
<212> TYPE: DNA
<213> ORGANISM: Nigrospora oryzae

<400> SEQUENCE: 60

```
ctcccaaccc atgtgaactt atctctttgt tgcctcggcg caagctaccc gggacctcgc      60
gccccgggcg gccgccggc ggacaaacca aactctgtta tcttcgttga ttatctgagt       120
gtcttattta ataagtcaaa actttcaaca acggatctct tggttctggc atcgatgaag      180
aacgcagcaa aaacgcagc attatcccac tcccaaaccc gtgggaa                    227
```

<210> SEQ ID NO 61
<211> LENGTH: 216
<212> TYPE: DNA
<213> ORGANISM: Nigrospora sp.

<400> SEQUENCE: 61

```
cccatgtgaa catatctctt tgttgcctcg gcgcaagcta cccgggacct cgcgccccgg      60
gcggcccgcc ggcggacaaa ccaaactctg ttatcttcgt tgattatctg agtgtcttat      120
ttaataagtc aaaactttca acaacggatc tcttggttct ggcatcgatg aagaacgcag      180
cagaaacgct cagccaactc ccagacccgt gtgaag                                216
```

<210> SEQ ID NO 62
<211> LENGTH: 249
<212> TYPE: DNA
<213> ORGANISM: Nigrospora sphaerica

<400> SEQUENCE: 62

```
actcccaaac ccatgtgaac atatctcttt gttgcctcgg cgcaagctac ccgggacctc      60
gcgccccggg cggccgccg gcggacaaac caaactctgt tatcttcgtt gattatctga       120
gtgtcttatt taataagtca aaactttcaa caacggatc cttggttctg gcatcgatga      180
agaacgcagc aaaaaaaaaa atattccact ccccaagccg gggggaaaa ttttttttt       240 tttttttgg                                                              249
```

<210> SEQ ID NO 63
<211> LENGTH: 223
<212> TYPE: DNA
<213> ORGANISM: Paecilomyces sp.

<400> SEQUENCE: 63

```
aatgcggact cccaaaccac tgtgaacata cccgtaccgt tgcctcggcg ggcggcccca    60
gggcggggcc gcagcctccc cagcggaggc gcccgccgca ggtcgcaaaa ctataactat   120
atttagtggc atctctgagt aacttccaaa caatcaaaac tttcaacaac ggatctcttg   180
gttctggcat cgatgaagaa cgcagccaat acagaacttc gcg                    223

<210> SEQ ID NO 64
<211> LENGTH: 205
<212> TYPE: DNA
<213> ORGANISM: Penicillium citrinum

<400> SEQUENCE: 64
aagtacgtga acggggcaaa cctcccaccc gtgttgcccg aacctatgtt gcctcggcgg    60
gccccgcgcc cgccgacggc ccccctgaac gctgtctgaa gttgcagtct gagacctata   120
acgaaattag ttaaaacttt caacaacgga tctcttggtt ccggcatcga tgaagaacgc   180
agcatctggc atcggctgca attcg                                        205

<210> SEQ ID NO 65
<211> LENGTH: 213
<212> TYPE: DNA
<213> ORGANISM: Retroconis sp.

<400> SEQUENCE: 65
gctatcccaa ccattgtgaa cctacctaca accgttgctt cggcgggcgg ccccgggtct    60
ccccgggcgc ccctccggcc cctcgcgggg gcccgccgga ggtacgcaac cctctgtatt   120
tgcatggcct ctctgagtct ctgtactgaa taagtcaaaa ctttcaacaa cggatctctt   180
ggttctggca tcgatgaaga acgcagcagc tac                               213

<210> SEQ ID NO 66
<211> LENGTH: 253
<212> TYPE: DNA
<213> ORGANISM: Rhizopycnis sp.

<400> SEQUENCE: 66
gaaatattgg gggtaagttt acgcttaacc aaaccgttcc gtaggtgaac ctgcggaagg    60
atcattatcg atttcggttt acaccgtttt ctacctttgt ctatgcgtac cacacgttcc   120 ctcgggggc ttggccccca ctaggaccaa acataaacct ttggtaatgg caatcggggt   180
ctgaaataat ttaattatta caactttaaa caacggatct ctgggttctg catcggtaa   240 aaaaacacag gaa                                                     253

<210> SEQ ID NO 67
<211> LENGTH: 210
<212> TYPE: DNA
<213> ORGANISM: Schizothecium inaequale

<400> SEQUENCE: 67
tgcaactccc aaccattgtg aacctacctc accgttgcct cggcgggtgg cccccacccg    60
ggccgcgccg gccccaccgg gccggcaacc cgtcagagga ccgcaactct tagtcatcat   120
tggcctctct gagtaactta tacaataagt caaaactttc aacaacggat ctcttggttc   180
tggcatcgat gaagaacgca gcaagtctaa                                   210

<210> SEQ ID NO 68
<211> LENGTH: 237
<212> TYPE: DNA
```

<213> ORGANISM: Stagonospora sp.

<400> SEQUENCE: 68

```
ctagctactg gcatggggac tgttagtctg catggtatca ctaccgatga gcagcaggtc    60
ccctgtctat acccttgttt tttgcgtacc tattgtttcc tcggcgggct tgctcgccgg   120
ctggacaaaa tctataacct ttttttaatc ttcaatcagc gtctgaaatt atacataata   180
attacaactt tcaacaacgg atctcttggt tctggcatcg atgaaaaacg cagccaa     237
```

<210> SEQ ID NO 69
<211> LENGTH: 223
<212> TYPE: DNA
<213> ORGANISM: Stemphylium lancipes

<400> SEQUENCE: 69

```
aaatgtggcg ccctttggta ttccaaaggg catgcctgtt cgagcgtcat ttgtaccctc    60
aagctttgct tggtgttggg cgtctttgtc tctcacgaga ctcgccttaa aatgattggc   120
agccgaccta ctggtttcgg agcgcagcac aattcttgca ctttgaatca gccttggttg   180
agcatccatc aagaccacat ttttttaact ttttaccgta cta                    223
```

<210> SEQ ID NO 70
<211> LENGTH: 209
<212> TYPE: DNA
<213> ORGANISM: Thielavia hyrcaniae

<400> SEQUENCE: 70

```
ctaaaccatt gtgaacctac cttctaccgt tgcttcggcg ggcgggcccc agcgcccccc    60
ccggcccccc gcgggcgccc gccggaggat acccaaactc ttgacattag tggcctctct   120
gagtattctt tactgaataa gtcaaaactt tcaacaacgg atctcttggt tctggcatcg   180
atgaagaacg cagcaattta cagagttgc                                    209
```

<210> SEQ ID NO 71
<211> LENGTH: 252
<212> TYPE: DNA
<213> ORGANISM: Thielavia sp.

<400> SEQUENCE: 71

```
aaccattgtg acgttacctt caaaccgttg cttcggcggg cggcccgggt ccgcccggtg    60
cccccctggcc ccctcgcggg gcgcccgccg gaggaaaccc aactcttgat acattatggc   120
ctctctgagt cttctgtact gaataagtca aaactttcaa caacggatct cttggttctg   180
gcatcgatga agaacgcagc gaaatgcgat aagtaatgtg aattgcagaa ttcagtgaat   240
catcgaatct tt                                                      252
```

<210> SEQ ID NO 72
<211> LENGTH: 217
<212> TYPE: DNA
<213> ORGANISM: Ulocladium chartarum

<400> SEQUENCE: 72

```
tgaagcgggc tggcatcctt cggggttaca gccttgctga attattcacc cgtgtctttt    60
gcgtacttct tgtttccttg gtgggttcgc ccaccatagg acaaaccata aaccttttgt   120
aattgcaatc agcgtcagta aaaaaattaa taattacaac ttttaacaac ggatctcttg   180
gttctggcat cgatgaagaa cgcagccact tacaaaa                            217
```

<210> SEQ ID NO 73
<211> LENGTH: 219
<212> TYPE: DNA
<213> ORGANISM: Verticillium sp.

<400> SEQUENCE: 73

```
gtacacgata ctcataaccc tttgtgaacc ttcatacctg ttgcttcggc ggcgcgcctc    60
tcggggcgtg cccgccggca ttatcagaat ctctgttcga acccgacgat acttctgagt   120
gttctaagcg aactgttaaa actttcaaca acggatctct tggctccagc atcgatgaag   180
aacgcagcaa ggatcaatga atttctcacc acccaagta                          219
```

<210> SEQ ID NO 74
<211> LENGTH: 477
<212> TYPE: DNA
<213> ORGANISM: Beauveria bassiana

<400> SEQUENCE: 74

```
ccgagttttc aactcccaaa cccttatgtg aactcaccta tcgttgcttc ggcggactcg    60
ccccagccgg acgggactgg accagcggcc cgccgggac ctcaaactct tgtattccag    120
catcttctga atacgccgca aggcaaaaca tatgaatcaa actttcaac aacggatctc    180
ttggctctgg catcgatgaa gaacgcagcg aaatgcgata agtaatgtga attgcagaat   240
ccagtgaatc atcgaatctt tgaacgcaca ttgcgcccgc cagcattctg gcgggcatgc   300
cctttcgagc gtcatttcaa ccctcgaccc ccccttgggg aggtcggcgt tggggacggc   360
agcacaccgc cggccctgaa atggagtggc ggcccgtccg cggcgacctc tgcgtagtaa   420
tacagctcgc accgtaaccc gacgcggcct caccgtaaaa cgacccaact tctgaac      477
```

<210> SEQ ID NO 75
<211> LENGTH: 506
<212> TYPE: DNA
<213> ORGANISM: Aspergillus parasiticus

<400> SEQUENCE: 75

```
ccgagtgtag ggttcctagc gagcccaacc tcccacccgt gtttactgta ccttagttgc    60
ttcggcgggc ccgccattca tggccgccgg gggttctcag ccccgggccc gcgcccgccg   120
gagacaccac gaactctgcc tcatctaatg aagtctgagt tgattgtatc gcaatcactt   180
taaactttca acaatggatc tcttggttcc gggatcaatg agcaacccaa caaaatgcga   240
taactagtgt gaattgcaga attccgtgaa tcatcgagtc tttgaacgca cattgcgccc   300
cctggtattc ctgcggggat gcatgtccga gctgaattgc tgcccatcaa gtacgacttg   360
tgtgttgggt cgtcgtcccc tctccggggg gacgggccc caaacgcagc tgaggcaccg   420
cggccgatcc tagagggtat gggcgctttg tcacctgatc tataggccag gccggcgcta   480
gcctaaccca aatcaatctt ttacag                                        506
```

<210> SEQ ID NO 76
<211> LENGTH: 451
<212> TYPE: DNA
<213> ORGANISM: Lecanicillium lecanii
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:

```
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t

<400> SEQUENCE: 76
ccggcgtccg gacggcctcg cgccgcccgc ggcccggacc caggcggccg ccggagacct      60
ctaaactctg tattatcagc attttctgaa tccgccgcaa ggcaaaacaa atgaatcaaa     120
actttcaaca acggaacctc ttgggtttcg ggcatcgatg aagaacgcag cgaaatgcga     180
taagtaatgt gaattgcaga attcagtgaa tcatcgaatc tttgaacgca cattgcgccc     240
gccagcattc tggcgggcat gcctgttcga gcgtcatttc aaccctcgac ttcccttggg     300
ggaaatccgc gttgggaaa cggcagcata cccgccnggc cccgaaatgg gagtggcggc      360
ccggtcccgc ngcgacccct ctgcgtaagt aatccaactc ggcaccggaa cccnacgtg     420 gccaccccng taaaacaccc aacttccgaa c                                    451

<210> SEQ ID NO 77
<211> LENGTH: 549
<212> TYPE: DNA
<213> ORGANISM: Paecilomyces lilacinus

<400> SEQUENCE: 77
ggagggatca ttaccgagtt tacaactccc aaaccccctg tgaacttata ccattactgt      60
tgcttcggcg ggttattgcc ccggggaagg atagggtgcc gcgaggtgcc ctgcccgccc     120
ccccggaaac aggcgcccgc cggaggactc aaactctgta tttttcttg ttttagtgta      180 tactatctga gtaaaaaaca atataatgaa tcaaaacttt caacaacgga tctcttggtt     240
ctggcatcga tgaagaacgc agcgaaatgc gataagtaat gtgaattgca gaattcagtg     300
aatcatcgaa tctttgaacg cacattgcgc ccgccagtat tctggcgggc atgcctgttc     360
gagcgtcatt tcaaccctca gcccctttg gacttggtgt tggggaccgg cgatggacaa     420
actgtccttt cgccgccccc taaatgactt ggcggcctcg tcgcggccct cctctgcgta     480
gtagcacaca cctcgcaaca ggagcccggc gaatggccac tgccgtaaaa cccccccaact     540 tttttcaga                                                             549
```

FUNGAL ENDOPHYTES FOR IMPROVED CROP YIELDS AND PROTECTION FROM PESTS

CROSS REFERENCE TO RELATED APPLICATIONS

This application claims priority to U.S. Provisional Patent Application Nos. 61/900,929 and 61/900,935, both filed Nov. 6, 2013, which are herein incorporated by reference in their entirety.

INCORPORATION OF SEQUENCE LISTING

The sequence listing that is contained in the file named TAMC027US_ST25.txt, which is 33 kilobytes as measured in Microsoft Windows operating system and was created on Nov. 6, 2014, is filed electronically herewith and incorporated herein by reference.

FIELD OF THE INVENTION

The present invention relates to fungal endophytes of agricultural crops for improving yield and/or for protection from pests.

DESCRIPTION OF RELATED ART

Fungal endophytes are fungi that internally colonize plant tissues without causing evident damage or disease. Particular fungal endophytes, such as mycorrhiza, survive within various host plant tissues, often colonizing the intercellular spaces of host leaves, stems, flowers or roots. The symbiotic endophyte-host relationships can provide several fitness benefits to the host plant, such as enhancement of nutrition, and/or increased drought tolerance. Root-colonizing mycorrhizae survive on photosynthetic carbohydrates from the plant, and in return, aid in the solubilization and uptake of water and minerals to the host, which can lead to the promotion of seed germination and plant growth. Additionally, the association of a fungal endophyte with a host plant can provide tolerance to a variety of biotic and abiotic stresses. Host growth, fitness promotion and protection are thought to be achieved through multiple beneficial properties of the endophyte-host association. For instance, the endophytic organisms may produce growth-regulating substances to induce biomass production and alkaloids or other metabolites. Additionally, fungal endophytes may directly suppress or compete with disease-causing microbes, protecting the plant from potential pathogens.

SUMMARY OF THE INVENTION

In one aspect, the invention provides methods for improving a trait in an agricultural plant comprising contacting an agricultural seed of said plant with a formulation comprising a purified facultative fungal endophytes of at least one species, wherein the endophytes are capable of producing substances that are beneficial to plants or detrimental to pests or both, and wherein the endophytes are present in the formulation in an amount effective to modulate the colonization frequencies of the endophytes that are native to the agricultural plant grown from the seed compared to a reference seed that is planted in an agricultural environment, and to provide a benefit to the seeds or the agricultural plants grown from the seeds.

In another aspect, the invention provides methods for providing a benefit to an agricultural plant comprising treating said plant, the seed of said plant, or the rhizosphere of said plant or seed with a composition comprising purified facultative fungal endophytes and an agriculturally-acceptable carrier, wherein the endophyte is capable of at least one of: reducing pest reproduction, killing pests, and deterring pests, and wherein the endophyte is present in the composition in an amount effective to provide a benefit to the seeds or the agricultural plants derived from the seeds.

In yet another aspect, the invention provides methods for providing a benefit to an agricultural plant, comprising obtaining a synthetic combination of an agricultural plant seed and a purified facultative fungal endophyte, wherein the endophyte is capable of at least one of: reducing pest reproduction, killing pests, and deterring pests, and wherein the endophyte is present in the synthetic combination in an amount effective to provide a benefit to the seeds or the agricultural plants derived from the seeds.

In another embodiments, methods of producing a plant with a non-naturally occurring ratio of endophytes is provided, where the methods comprise contacting an agricultural seed of the plant with a formulation comprising facultative fungal endophytes of at least one species, wherein endophytes are present in the formulation in an amount effective to modulate the colonization frequencies of the endophytes that are native to the agricultural plant grown from the seed compared to a reference seed that is planted in an agricultural environment, wherein the plant with the non-naturally occurring ratio of endophytes has an improved trait as compared to a plant with a naturally-occurring ratio. In a further aspect, the facultative fungal endophytes are capable of producing substances that are beneficial to plants or detrimental to pests or both.

In another aspect, the invention provides methods for altering the systemic defensive pathway in a plant comprising contacting an agricultural seed of said plant with a formulation comprising a purified facultative fungal endophytes of at least one species, wherein the endophytes are capable of producing substances that are beneficial to plants or detrimental to pests or both, and wherein the endophyte is present in the synthetic combination in an amount effective to modulate the level of at least one phytohormone within an agricultural plant grown from the plant seed, and to provide a benefit to the seeds or the agricultural plants grown from the seeds. In a further aspect, the facultative fungal endophytes are capable of producing substances that are beneficial to plants or detrimental to pests or both.

In other embodiments, the invention provides methods of modulating the colonization frequencies of endophytes that are native to the agricultural plant grown from the seed compared to a reference seed that is planted in an agricultural environment, comprising contacting the seed of the agricultural plant with a formulation comprising facultative fungal endophytes of at least one species, and wherein endophytes are present in the formulation in an amount effective to modulate the colonization frequencies of native endophytes and to provide a benefit to the seeds or the agricultural plants grown from the seeds. In certain aspects, the native endophytes are of genus *Alternaria*. In a further aspect, the facultative fungal endophytes are capable of producing substances that are beneficial to plants or detrimental to pests or both.

In another aspect, the invention provides methods for altering the systemic defensive pathway in a plant comprising contacting an agricultural seed of said plant with a formulation comprising a purified facultative fungal endophytes of at least one species, and wherein the endophyte is present in the synthetic combination in an amount effective to modulate the level of at least one phytohormone within an agricultural plant grown from the plant seed, and to provide a benefit to the seeds or the agricultural plants grown from the seeds. In a further aspect, the facultative fungal endophytes are capable of producing substances that are beneficial to plants or detrimental to pests or both.

In yet another aspect, the invention provides methods of producing a plant with a network of fungal endophytes that comprises endophytes of the genus *Alternaria*, comprising (a) contacting the seed of an agricultural plant with a formulation comprising facultative fungal endophytes of at least one non-*Alternaria* species, wherein endophytes are present in the formulation in an amount effective to provide a benefit to the seeds or the agricultural plants grown from the seeds, and wherein the plant grown from the seed comprises endophytes of the genus *Alternaria*. In a further aspect, the facultative fungal endophytes are capable of producing substances that are beneficial to plants or detrimental to pests or both.

Also provided herein are synthetic combinations of an agricultural plant seed and a composition comprising purified entomopathogenic fungal endophytes of at least one species, wherein the endophytes are capable of (1) colonizing the agricultural plant grown from the plant seed (2) and at least one of: reducing pest reproduction, killing pests, and deterring pests, from within the agricultural plant; wherein the endophytes are not of species *Beauveria bassiana*, and wherein the endophyte is present in the synthetic combination in an amount effective to provide a benefit other than enhanced resistance to biotic stress to the seeds or the agricultural plants derived from the seeds when the seeds or plants are grown in an agricultural setting.

In yet another aspect, the invention provides synthetic combinations of an agricultural plant seed and a composition comprising purified facultative fungal endophytes of at least one species, wherein the endophyte is present in the synthetic combination in an amount effective to modulate the level of at least one phytohormone within an agricultural plant grown from the plant seed, and to provide a benefit to the seeds or the agricultural plants grown from the seeds. In a further aspect, the facultative fungal endophytes are capable of producing substances that are beneficial to plants or detrimental to pests or both.

In another embodiment, the invention provides synthetic combinations of an agricultural plant seed and a composition comprising purified facultative fungal endophytes of at least one species, wherein the facultative fungal endophytes are present in the synthetic combination in an amount effective to modulate the colonization frequencies of endophytes that are native to the agricultural plant grown from the seed compared to a reference seed that is planted in an agricultural environment, and to provide a benefit to the seeds or the agricultural plants grown from the seeds. In a further aspect, the facultative fungal endophytes are capable of producing substances that are beneficial to plants or detrimental to pests or both. In certain aspects, the facultative fungal endophytes are present in the synthetic combination in an amount effective to modulate the colonization frequencies of endophytes of genus *Alternaria* that are native to the agricultural plant grown from the seed compared to a reference seed that is planted in an agricultural environment.

In a further aspect for certain of these methods and synthetic combinations, the composition comprising purified facultative fungal endophytes also comprises an agriculturally acceptable carrier.

In a further aspect for certain of these methods and synthetic combinations, the facultative fungal endophyte may be a filamentous fungal endophyte. In other embodiments, the facultative endophyte may be spore-forming. In yet other embodiments, the facultative fungal endophyte may be a septate fungal endophyte. In yet other embodiments, the facultative fungal endophyte may be a dark septate fungal endophyte. In some embodiments, the facultative endophyte may be an entomopathogen. In some embodiments, the facultative fungal endophyte may belong to the phylum Ascomycota or Basidiomycota. In a further aspect, the facultative fungal endophyte may belong to subphylum Pezizomycotina, Agaricomycotina, or Ustilaginomycotina. In yet another aspect, facultative fungal endophyte may belong to class Sordariomycetes, Dothideomycetes, Agaricomycetes, Ustilaginomycetes, Orbiliomycetes, or Eurotiomycetes. In yet another aspect, the facultative fungal endophyte may belong to order Hypocreales, Pleosporales, Capnodiales, Sordariales, Polyporales, Diaporthales, Ustilaginales, Xylariales, Orbiliales, Trichosphaeriales, or Eurotiales.

In a further aspect, the facultative fungal endophyte may be a species from Table 1, namely *Acremonium altematum, Alternaria altemata, Alternaria brassicae, Alternaria compacta, Alternaria dianthi, Alternaria longipes, Alternaria mali, Alternaria sesami, Alternaria solani, Alternaria* sp., *Alternaria tenuissima, Ascomycota* sp., *Bipolaris spicifera, Cercospora canescens, Cercospora capsici, Cercospora kikuchii, Cercospora zinnia, Chaetomium globosum, Chaetomium piluliferum, Chaetomium* sp., *Cladosporium cladosporioides, Cladosporium* sp., *Cladosporium uredinicola, Cochliobolus* sp, *Phanerochaete crassa, Phoma americana, Phoma subherbarum, Phomopsis liquidambari, Phomopsis* sp., *Pleospora* sp., *Pleosporaceae* sp., *Polyporales* sp., *Preussia africana, Preussia* sp., *Pseudozyma* sp., *Pyrenophora teres, Colletotrichumcapsici, Coniolariella gamsii, Coniothyrium aleuritis, Coniothyrium* sp., *Corynespora cassiicola, Diaporthe* sp., *Diatrype* sp., *Drechslerella dactyloides, Embellisia indefessa, Epicoccum nigrum, Epicoccum* sp., *Exserohilum rostratum, Fusarium chlamydosporum, Fusarium* sp., *Gibellulopsis nigrescens, Gnomoniopsis* sp., *Lewia infectoria, Mycosphaerella coffeicola, Mycosphaerellaceae* sp., *Nigrospora oryzae, Nigrospora* sp., *Nigrospora sphaerica, Paecilomyces* sp., *Penicillium citrinum, Retroconis* sp., *Rhizopycnis* sp., *Schizothecium inaequale, Stagonospora* sp., *Stemphylium lancipes, Thielavia hyrcaniae, Thielavia* sp., *Ulocladium chartarum, Verticillium* sp., *Beauveria bassiana, Aspergillus parasiticus, Lecanicillium lecanii*, and *Paecilomyces lilacinus*.

In a further aspect, the facultative fungal endophyte comprises a nucleic acid that is at least 97% identical, for example, at least 98% identical, at least 99% identical, at least 99.5% identical, or 100% identical to the nucleic acids provided in any of SEQ ID NO:7 through SEQ ID NO:77, for example those listed in Example 16.

In another aspect for certain of these methods is an additional step of packaging the contacted seeds in a container may be included. In certain aspects, the packaging material may be selected from a bag, box, bin, envelope, carton, or container, and may comprise a dessicant.

In a further aspect for certain of these methods and synthetic combinations, the benefit to the treated seed or plant grown from the treated seed is measured at the level of the population, as compared to a reference population of plants. In certain aspects, the facultative fungal endophyte may be providing a benefit to a crop comprising a plurality of agricultural plants produced from the seeds treated with the endophyte. In certain aspects, the present invention discloses a substantially uniform population of plants produced by growing the population of seeds described above. In one embodiment, at least 75%, at least 80%, at least 90%, at least 95% or more of the plants comprise in one or more tissues an effective amount of the endophyte or endophytes. In another embodiment, at least 10%, 20%, 30%, 40%, 50%, 60%, 70%, 75%, at least 80%, at least 90%, at least 95% or more of the plants comprise a microbe population that is substantially similar.

In a further aspect for certain of these methods and synthetic combinations, the plant is grown in an agricultural setting or environment, including a greenhouse. In one embodiment, the agricultural setting or environment comprises at least 100 plants. In another embodiment, the population occupies at least about 100 square feet of space, wherein at least about 10%, 20%, 30%, 40%, 50%, 60%, 70%, 80%, 90% or more than 90% of the population comprises an effective amount of the microbe. In another embodiment, the population occupies at least about 100 square feet of space, wherein at least about 10%, 20%, 30%, 40%, 50%, 60%, 70%, 80%, 90% or more than 90% of the population comprises the microbe in reproductive tissue. In still another embodiment, the population occupies at least about 100 square feet of space, wherein at least about 10%, 20%, 30%, 40%, 50%, 60%, 70%, 80%, 90% or more than 90% of the population comprises at least 10 CFUs, 100 CFUs, 1,000 CFUs, 10,000 CFUs or more of the facultative fungal endophyte of the invention. In yet another embodiment, the population occupies at least about 100 square feet of space, wherein at least about 10%, 20%, 30%, 40%, 50%, 60%, 70%, 80%, 90% or more than 90% of the population comprises the facultative fungal endophyte of the invention.

In one embodiment, at least 10%, at least 20%, at least 30%, at least 40%, at least 50%, at least 60%, at least 70%, at least 75%, at least 80%, at least 90%, at least 95% or more of the seeds in the population, contains a viable endophyte or endophytes disposed on the surface of the seeds. In a particular embodiment, at least 10%, at least 20%, at least 30%, at least 40%, at least 50%, at least 60%, at least 70%, at least 75%, at least 80%, at least 90%, at least 95% or more of the seeds in the population contains at least 10 CFU, for example, at least 30 CFU, at least 100 CFU, at least 300 CFU, at least 1,000 CFU, at least 3,000 CFU, at least 10,000 CFU or more, of the endophyte or endophytes coated onto the surface of the seed.

In a further aspect for certain of these methods and synthetic combinations, the endophytes that are native to the agricultural plant and whose colonization frequencies or ratios are altered may belong to phylum Ascomycota or Basidiomycota. In yet another aspect, the endophytes that are native to the agricultural plant may be of class Leotiomycetes, Dothideomycetes, Eurotiomycetes, Saccharomycetes, Sordariomycetes, Agaricomycetes, Microbotryomycetes, Tremellomycetes. In yet another aspect, the native endophytes may belong to order Capnodiales, Pleosporales, Chaetothyriales, Eurotiales, Saccharomycetales, Diaporthales, Hypocreales, Ophiostomatales, Sordariales, Trichosphaeriales, Xylariales, Cantharellales, Corticiales, Polyporales, Russulates, Sporidiobolales, or Tremellales. In a further aspect, the native endophytes may belong to genus *Davidiellaceae, Mycosphaerellaceae, Pleosporaceae, Didymellaceae, Sporormiaceae, Chaetothyriaceae, Trichocomaceae, Saccharomycetaceae, Gnomoniaceae, Cordycipitaceae, Nectriaceae, Hypocreaceae, Plectosphaerellaceae, Ophiostomataceae, Chaetomiaceae, Lasiosphaeriaceae, Trichosphaeriaceae, Ceratobasidiaceae, Corticiaceae, Coriolaceae, Peniophoraceae, Sporidiobolaceae,* or *Tremellaceae.* In a further aspect, the endophytes that are native to the agricultural plant may be a species from Table 2, namely *Cladosporium* sp., *Cladosporium cladosporioides, Davidiella* sp., *Cercospora* sp., *Cercospora beticola, Alternaria* sp., *Alternaria alternata, Alternaria citri, Alternaria tenuissima, Cochliobolus* sp., *Curvularia* sp., *Exserohilum* sp., *Lewia* sp., *Lewia infectoria, Pyrenophora* sp., *Pyrenophora tritici-repentis, Pleospora* sp., *Phoma americana, Preussia africana, Penicillium* sp., *Thermomyces* sp., *Thermomyces lanuginosus, Candida* sp., *Candida quercitrusa, Candida tropicalis, Cyberlindnera* sp., *Cyberlindnera jadinii, Kluyvemmyces* sp., *Kluyveromyces marxianus, Gnomoniopsis* sp., *Beauveria bassiana, Cordyceps* sp., *Cordyceps bassiana, Fusarium* sp., *Gibellulopsis nigrescens, Hypocrea* sp., *Hypocrea lixii, Hypocrea virens, Trichoderma* sp., *Trichoderma tomentosum, Verticillium* sp., *Ophiostoma* sp., *Ophiostoma dendifundum, Chaetomium* sp., *Chaetomium globosum, Thielavia hyrcaniae, Taifanglania* sp., *Taifanglania inflata, Schizothecium inaequale, Nigrospora* sp., *Rhizoctonia* sp., *Phanerochaete* sp., *Trametes* sp., *Trametes hirsuta, Trametes viliosa, Rhodotorula* sp., *Rhodotorula mucilaginosa, Cryptococcus* sp, *Cryptococcus skinneri,* or *Tremella* sp.

In a further aspect for certain of these methods and synthetic combinations, the benefit provided by the facultative fungal endophyte to the agricultural plant is an improved agronomic property selected from the group consisting of increased biomass, increased tillering, increased root mass, increased flowering, increased yield, increased water use efficiency, reduction of yield loss, altered plant height, decreased time to emergence, increased seedling height, increased root length, increased chlorophyll levels, retention of developing flowers, retention of developing fruits, altered phytohormone levels, and enhanced resistance to environmental stress relative to a reference plant. In some aspects, the benefit provided is the alteration of levels of at least two phytohormones. In some aspects, the environmental stress is selected from the group consisting of drought stress, cold stress, heat stress, nutrient deficiency, salt toxicity, aluminum toxicity, grazing by herbivores, insect infestation, nematode infection, and fungal infection, bacterial infection and viral infection. In some aspects, the benefit to agricultural plants derived from the seed is increased yield in a population of said plants by about 5%, 10%, 15%, 20%, 30%, 40%, or 45% relative to a reference population of plants. In other aspects, the benefit to agricultural plants derived from the seed is a reduction of yield loss in a population of said plants by more than 40%, 30%, 20%, 10%, 5%, or 1% relative to a reference population of plants. In some aspects, treatment of seeds with facultative fungal endophytes may decrease thrip damage, decrease fleahopper damage, increase canopy temperature, increase drought tolerance, increase above ground biomass, and increase below ground biomass in the plants grown from the treated seeds.

In a further aspect for certain of these methods and synthetic combinations, the facultative fungal endophyte is present in the synthetic combination in an amount effective to obtain at least 50% colonization of the leaves, stems or roots of an agricultural plant grown from the seed.

In a further aspect for certain of these methods and synthetic combinations, the facultative fungal endophytes are capable of producing substances that are detrimental to pests. In certain aspects, the pest may be a nematode and/or an insect, for example, a root knot nematode, a aphid, a lygus bug, a stink bug, or combinations thereof.

In a further aspect for certain of these methods and synthetic combinations, the synthetic combination may comprise at least 1, 2, 3, 4, 5, 6, 7, 8, 9, 10, 11, 12, 13, 14, 15, 16, 17, 18, 19, or 20 facultative fungal endophytes. In one aspect, the invention provides a synthetic combination of a cotton plant or seed and a fungal endophyte comprising at least 1, 2, 3, 4, 5, 6, 7, 8, 9, 10, 11, 12, 13, 14, 15, 16, 17, 18, 19, or 20 endophytes selected from those in Table 1, wherein the cotton or seed is a host of the endophyte.

In another aspect, a seed coating is provided comprising a fungal endophyte comprising at least 1, 2, 3, 4, 5, 6, 7, 8, 9, 10, 11, 12, 13, 14, 15, 16, 17, 18, 19, or 20 endophytes from Table 1; and at least one sticker, wherein the fungal endophyte is in contact with the sticker. In certain aspects, the sticker may comprise, for example, alginic acid, carrageenan, dextrin, dextran, pelgel, polyethelene glycol, polyvinyl pyrrolidone, methyl cellulose, polyvinyl alcohol, gelatin, or combinations thereof. In certain aspects, the sticker may have a weight ratio between fungal endophyte and sticker of 1:1-10, 1:10-50, 1:50-100, 1:100-500, 1:500-1000, or 1:1000-5000. The seed coating may be a solid or fluid. In certain aspects, the seed coating is a powder. In certain aspects, the fungal endophyte may comprise fungal spores. In various aspects, the seed coating may comprise about 1, 2, 5, 10, 50, $10^2$, $10^3$, $10^4$, $10^5$, $10^6$, $10^7$, $10^8$, or $10^9$ or more colony forming units per gram or spores per gram.

In certain embodiments, compositions for foliar or soil application may comprise a fungal endophyte comprising at least 1, 2, 3, 4, 5, 6, 7, 8, 9, 10, 11, 12, 13, 14, 15, 16, 17, 18, 19, or 20 endophytes from Table 1, and at least one carrier, surfactant or diluent. In certain aspects, the compositions may comprise may comprise about 1, 2, 5, 10, 50, $10^2$, $10^3$, $10^4$, $10^5$, $10^6$, $10^7$, $10^8$, or $10^9$ or more colony forming units per gram or spores per gram. In various aspects, the composition may comprise water, a detergent, Triton X, insecticides, fungicides, or combinations thereof, for example. In further embodiments, seed compositions comprise a plant seed and the above-described seed coating. In certain aspects, the plant seed comprises a cotton seed, a seed of an agronomically elite plant, a dicot plant seed, and/or a monocot plant seed. In certain aspects, the seed composition may be resistant to a pest comprising an insect and/or a nematode.

In yet another aspect, the invention provides methods for preventing pest infestation or increasing yield, which may comprise treating a plant, plant seed, or the rhizosphere of said plant or seed with the endophyte containing compositions described herein. In certain aspects, the method may also comprise identifying a plant or seed as in need of endophyte treatment. The pest may comprise, for example, a nematode and/or insect. In certain aspects, the pest may comprise a root knot nematode, a aphid, a lygus bug, a stink bug, or combinations thereof.

In still yet another aspect, methods for preventing pest infestation are provided comprising obtaining a seed described herein and planting the seed. The method may further comprise identifying a need of preventing pest infestation. In certain aspects, the pest may comprise a nematode and/or a insect; and/or the pest may comprise a root knot nematode, a aphid, a lygus bug, a stink bug, or combinations thereof.

In a further embodiment, a method for treating a pest infestation comprises identifying a plant suspected of being infected with a pest, applying an above-described composition to the plant, whereby an endophyte-treated plant is generated. In certain aspects, the pest may comprise a nematode and/or an insect; and/or the pest may comprise a root knot nematode, a aphid, a lygus bug, a stink bug, or combinations thereof.

In still yet another aspect, a method of manufacturing pest-resistant seeds is provided comprising providing a fungal endophyte composition comprising at least 1, 2, 3, 4, 5, 6, 7, 8, 9, 10, 11, 12, 13, 14, 15, 16, 17, 18, 19, or 20 endophytes from Table 1, providing seeds; and combining the seeds with the endophyte composition, whereby pest-resistant seeds are generated. In certain aspects, the method increases the percentage of colonization with the endophyte of the plant developing from the seed.

In still yet another aspect, methods of increasing a yield of a crop or a reduction of loss are disclosed comprising providing a fungal endophyte composition comprising at least 1, 2, 3, 4, 5, 6, 7, 8, 9, 10, 11, 12, 13, 14, 15, 16, 17, 18, 19, or 20 endophytes from Table 1; and applying the endophyte composition to a seed, plant or part thereof, whereby the yield of the crop increases. In certain aspects, the crop may be cotton, and the increase of yield may be at least about 2%, 3% 5%, 15%, 20%, or 25% relative to a crop to which no endophyte composition has been applied. In certain aspects, the increase of yield is about 2%-5%, 3%-5%, 5%-10%, 10%-15%, or greater than about 20%, 30%, or more relative to a crop to which no endophyte composition has been applied. In certain aspects, the crop is cotton and the increase of yield comprises reduced boll damage. In certain aspects, the reduction of loss comprises reduction of loss due to insect infestation or drought, and the loss is less than 50%, 40%, 30%, 20%, 10%, 5%, or 5% relative to a crop to which no endophyte composition has been applied.

Also described herein are commodity plant products comprising a plant or part of a plant (including a seed) and further comprising the facultative fungal endophyte described above that is present in a detectable level, for example, as detected by the presence of its nucleic acid by PCR. In another aspect, disclosed is a method of producing a commodity plant product, comprising obtaining a plant or plant tissue from the synthetic combination described above, and producing the commodity plant product therefrom. The commodity plant product can be produced from the seed, or the plant (or a part of the plant) grown from the seed. The commodity plant product can also be produced from the progeny of such plant or plant part. The commodity plant product can be is selected from the group consisting of grain, flour, starch, seed oil, syrup, meal, flour, oil, film, packaging, nutraceutical product, an animal feed, a fish fodder, a cereal product, a processed human-food product, a sugar or an alcohol and protein.

BRIEF DESCRIPTION OF THE DRAWINGS

FIG. 4A demonstrates that the presence of *Beauveria bassiana* in cotton negatively affects the reproduction of cotton aphids. FIG. 4B demonstrates that the presence of *Paecilomyces lilacinus* in cotton negatively affects the reproduction of cotton aphids.

FIGS. 6A, 6B: The effect of the endophytic fungi *Beauveria bassiana* and *Paecilomyces lilacinus* on western tarnished plant bugs *Lygus hesperus* (Miridae). FIG. 6A demonstrates that *Beauveria bassiana* and *Paecilomyces lilacinus* negatively affect host plant selection of western tarnished plant bugs when present as an endophyte in cotton. FIG. 6B demonstrates that *Beauveria bassiana* and *Paecilomyces lilacinus* negatively affect host plant selection behavior of western tarnished plant bugs when present as an endophyte in cotton.

FIG. 7A demonstrates that *Beauveria bassiana* and *Paecilomyces lilacinus* negatively affect host plant selection of southern green stink bugs when present as an endophyte in cotton. FIG. 7B demonstrates that *Beauveria bassiana* and *Paecilomyces lilacinus* negatively affect host plant selection behavior of southern green stink bugs when present as an endophyte in cotton.

FIG. 10: Positive effects of fungal endophytes on cotton plant performance under field conditions. Box A (left) demonstrates an early season trend for higher square retention in the treated versus untreated plants. Box B (right) demonstrates that significantly more bolls were retained in the endophyte treatment groups later in the season, relative to control. This is demonstrated with both endophyte species used and with both seed treatment concentration employed (Repeated measures ANOVA: Time, P<0.001; Time*Endophyte, P=0.045, Endophyte, P=0.003).

FIG. 16: Average percent difference in thrip damage (A) and fleahopper damage (B) between endophyte treated and control cotton plants. The thrip damage was assessed in the Delta Pine (DP 0912B2RF) cultivar (n=6 replicate plots in a dryland field, College Station, Tex.) for 15 facultative fungal endophytes. 12 out of the 15 facultative fungal endophytes tested showed a decrease in thrip damage relative to the untreated cotton plants. The fleahopper damage was assessed in cotton plants of the Phytogen (PHY 499WRF) cultivar (n=6 replicate plots in a dryland field, College Station, Tex.) for 15 facultative fungal endophytes. 6 out of the 15 facultative fungal endophytes tested showed an average decrease in fleahopper damage as compared to untreated cotton plants.

FIG. 24: Table showing the time to wilt following drought stress in days for plants grown from seeds treated with fungal endophytes and control.

FIG. 25: Table showing the time to death following drought stress in days for plants grown from seeds treated with fungal endophytes and control.

DETAILED DESCRIPTION OF THE INVENTION

Figure 1:
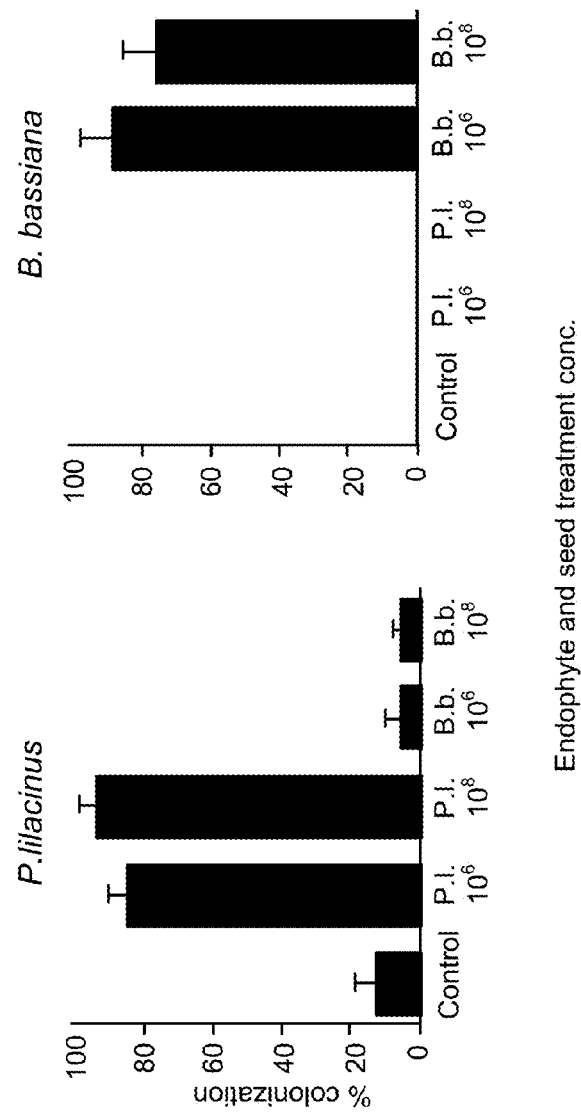
FIG. 1: The colonization efficiencies demonstrate that endophytes can be manipulated in the field. Depicted are the mean+/−SE endophytic colonization frequencies of cotton seedlings under field conditions inoculated by seed treatments with different spore concentrations of either (left) *Paecilomyces lilacinus* or (right) *Beauveria bassiana*.

Endophytic fungi are ubiquitous in nature, infecting virtually all plants in both natural and agronomic ecosystems. Plants commonly harbor a diversity of fungi living within their tissues as asymptomatic endophytes that can provide protection from a range of biotic and abiotic stressors. The present disclosure describes certain fungal endophytes that can be pathogens, parasites or antagonists to plant pathogens, insects, and nematode pests, thereby providing health and performance benefits to crop plants. The symbiotic endophyte-host relationships can provide several general health and fitness benefits to the host plant, such as enhancement of nutrition, increased drought tolerance and/or chemical defense from potential herbivores and often enhanced biomass production. Root-colonizing mycorrhizae survive on photosynthetic carbohydrates from the plant, and in return, aid in the solubilization and uptake of water and minerals to the host, which can lead to the promotion of seed germination and plant growth. Additionally, the association of a fungal endophyte with a host plant often provides protection from pathogens or tolerance to a variety of biotic and abiotic stresses, such as insect infestation, grazing, water or nutrient deficiency, heat stress, salt or aluminum toxicity, and freezing temperatures. Host growth and fitness promotion and protection are thought to be achieved through multiple beneficial properties of the endophyte-host association.

These fungal endophytes provided in Table 1 were originally collected as fungal endophytes of cotton. These endophytic fungi can be inoculated to live within cotton using either seed, soil or foliar applications and exhibited surprisingly beneficial effects by providing protection from pest infestation. Pests can be nematode and/or insect pests. In addition, these endophytic fungi have an unexpected beneficial effect on cotton yield.

Described is the application of beneficial fungi to establish endophytically within crop plants to improve plant performance and yield while conferring protection against insect and nematode pests. In this regard, the present invention overcomes the limitations of the prior art such as the susceptibility of the fungi to degradation by UV light, desiccation or heat after exposure to the environment following application as an inundative soil or foliar biopesticide. Inoculation and endophytic establishment of the fungi within the plant protects the fungi from UV light, desiccation, and unfavorable temperatures, while harboring the fungi in the very plant tissues they are intended to protect. Introducing fungi to live endophytically within plants requires no genetic modification of the plant or microorganisms, and the fungi themselves can be a source for natural products. In various embodiments, the fungal inoculant can be formulated and applied, for example, as treatment of seeds, in furrow applications, before or during planting, or as foliar application after plant germination, and after inoculation, the fungal endophytes provide season-long protective effects and higher crop yields (approximately 25% higher). In certain embodiments, the increase of yield is about 5%, 10%, 15%, 20%, 30%, 40%, 45%, 50%, or greater than 50% relative to a crop to which no endophyte composition has been applied. In further embodiments, the increase of yield is the result of reduction of loss that comprises reduction of loss due to insect infestation or drought and the loss is less than 50%, 40%, 30%, 20%, 10%, 5%, or 5% relative to a crop to which no endophyte composition has been applied. In certain embodiments, the crop is cotton and the reduction of loss comprises reduced boll damage.

Thus, in one aspect, the invention provides a combination (also termed a "symbiotum") of a host plant and an endophyte that allows for improved agronomic properties of host plants. The combination may be achieved by artificial inoculation, application, or other infection of a host plant or seeds thereof, such as a cotton plant or seed thereof, or host plant tissues, with a fungal endophyte strain of the present invention. Thus, a combination achieved by such an inoculation is termed a "synthetic" combination, synthetic composition, synthetic seed coating, and/or synthetic pest-resistant seed composition. The fungal endophyte may be present in intercellular spaces within plant tissue, such as the root. Its presence may also occur or may also be maintained within a plant or plant population by means of grafting or other inoculation methods such as treating seeds, plants or parts thereof with endophyte mycelia, or endophyte spores. In certain embodiments, the plant, part of the plant, roots, seed, or leaves are sterilized to remove microorganisms before applying the endophyte. In particular embodiments, seeds are sterilized to remove native endophytes before adding the endophyte compositions herein described. In certain aspects, the ability of the seed to germinate is not affected by the sterilization.

The invention also provides methods for detecting the presence of the fungal endophyte of the present invention within a host plant. This may be accomplished, for instance, by isolation of total DNA from tissues of a potential plant-endophyte combination, followed by PCR, or alternatively, Southern blotting, western blotting, or other methods known in the art, to detect the presence of specific nucleic or amino acid sequences associated with the presence of a fungal endophyte strain of the present invention. Alternatively, biochemical methods such as ELISA, HPLC, TLC, or fungal metabolite assays may be utilized to determine the presence of an endophyte strain of the present invention in a given sample of crop tissue. Additionally, methods for identification may include microscopic analysis, such as root staining, or culturing methods, such as grow out tests or other methods known in the art (Deshmukh et al. 2006). In particular embodiments, the roots of a potential grass plant-endophyte combination may be stained with fungal specific stains, such as WGA-Alexa 488, and microscopically assayed to determine fungal root associates.

In certain embodiments, the agronomic qualities may be selected from the group consisting of: increased biomass, increased tillering, increased root mass, increased flowering, increased seed yield, and enhanced resistance to biotic and/or abiotic stresses, each of these qualities being rated in comparison to otherwise identical plants grown under the same conditions, and differing only with respect to the presence or absence of a fungal endophyte. The synthetic combinations and methods of the present invention may be applied to respond to actual or anticipated stresses. Such stresses may include, for instance, drought (water deficit), cold, heat stress, nutrient deficiency, salt toxicity, aluminum toxicity, grazing by herbivores, insect infestation, nematode infection, and fungal, bacteria or viral infection, among others.

The present disclosure provides, in one embodiment, fungal endophytes selected from those in Table 1 that negatively affect the reproduction of insect herbivores feeding on leaves above ground (cotton aphids, *Aphis gossypii*) and plant parasitic nematodes attacking roots below ground (root knot nematodes, *Meloidogyne incognita*). In addition, improved plant performance and yields in colonized versus uncolonized control plants may be observed in field trials employing seed treatment with such endophytes. Plant growth enhancement and increased resistance to root knot nematodes was demonstrated in cotton, for example, employing *Chaetomium globosum* as an endophyte in greenhouse trials. In addition and as a further non-limiting illustrative example, using *Beauveria bassiana* as an endophyte in cotton, reductions in insect (cotton aphid) reproduction was demonstrated in both greenhouse and field trials. The endophytic presence of *Paecilomyces lilacinus* and *Beauveria bassiana* also had negative effects on the host selection behavior of key sucking bug pests (*Lygus hesperus* and *Nezara viridula*) that attack developing flowers and fruits in cotton. Furthermore, in field trials using *Beauveria bassiana* as an endophyte in cotton positive effects on plant performance and higher yields in endophyte colonized versus uncolonized control plants was demonstrated.

Metabolomic differences between the plants can be detected using methods known in the art. For example, a biological sample (whole tissue, exudate, phloem sap, xylem sap, root exudate, etc.) from the endophyte-associated and reference agricultural plants can be analyzed essentially as described in Fiehn et al., (2000) Nature Biotechnol., 18, 1157-1161, or Roessner et al., (2001) Plant Cell, 13, 11-29. Such metabolomic methods can be used to detect differences in levels in hormones, nutrients, secondary metabolites, root exudates, phloem sap content, xylem sap content, heavy metal content, and the like.

In another embodiment, the present invention contemplates methods of coating the seed of a plant with a plurality of endophytes, as well as seed compositions comprising a plurality of endophytes on and/or in the seed. The methods according to this embodiment can be performed in a manner similar to those described herein for single endophyte coating. In one example, multiple endophytes can be prepared in a single preparation that is coated onto the seed. The endophytes can be from a common origin (i.e., a same plant). Alternatively, the endophytes can be from different plants.

Where multiple endophytes are coated onto the seed, any or all of the endophytes may be capable of conferring a beneficial trait onto the host plant. In some cases, all of the endophytes are capable of conferring a beneficial trait onto the host plant. The trait conferred by each of the endophytes may be the same (e.g., both improve the host plant's tolerance to a particular biotic stress), or may be distinct (e.g., one improves the host plant's tolerance to drought, while another improves phosphate utilization). In other cases the conferred trait may be the result of interactions between the endophytes.

DEFINITIONS

In the description and tables herein, a number of terms are used. In order to provide a clear and consistent understanding of the specification and claims, the following definitions are provided. Unless otherwise noted, terms are to be understood according to conventional usage by those of ordinary skill in the relevant art.

When a term is provided in the singular, the inventors also contemplate aspects of the invention described by the plural of that term. The singular form "a," "an," and "the" include plural references unless the context clearly dictates otherwise. For example, the term "a cell" includes one or more cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and agriculturally acceptable carriers. "Consisting of" shall mean excluding more than trace elements of other ingredients and substantial method steps for applying the compositions of this invention. Embodiments defined by each of these transition terms are within the scope of this invention.

Biological control: the term "biological control" and its abbreviated form "biocontrol," as used herein, is defined as control of a pest, pathogen, or insect or any other undesirable organism by the use of at least one endophyte.

A "composition" is intended to mean a combination of active agent and at least another compound, carrier or composition, inert (for example, a detectable agent or label or liquid carrier) or active, such as a pesticide.

As used herein, an "agricultural seed" is a seed used to grow plants in agriculture (an "agricultural plant"). The seed may be of a monocot or dicot plant, and is planted for the production of an agricultural product, for example grain, food, fiber, etc. As used herein, an agricultural seed is a seed that is prepared for planting, for example, in farms for growing. Agricultural seeds are distinguished from commodity seeds in that the former is not used to generate products, for example commodity plant products.

As used herein, a "commodity plant product" refers to any composition or product that is comprised of material derived from a plant, seed, plant cell, or plant part of the present invention. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, and any other food for human or animal consumption; and biomasses and fuel products. Any such commodity plant product that is derived from the plants of the present invention may contain at least a detectable amount of the specific and unique DNA corresponding to the endophytes described herein. Any standard method of detection for polynucleotide molecules may be used, including methods of detection disclosed herein.

As used herein, the phrase "agronomically elite plants" refers to a genotype or cultivar with a phenotype adapted for commercial cultivation. Traits comprised by an agronomically elite plant may include biomass, carbohydrate, and/or seed yield; biotic or abiotic stress resistance, including drought resistance, insect resistance, fungus resistance, virus resistance, bacteria resistance, cold tolerance, and salt tolerance; improved standability, enhanced nutrient use efficiency, and reduced lignin content.

In certain embodiments, cotton agronomically elite plants include, for example, known cotton varieties AM 1550 B2RF, NG 1511 B2RF, NG 1511 B2RF, FM 1845LLB2, FM 1944GLB2, FM 1740B2F, PHY 499 WRF, PHY 375 WRF, PHY 367 WRF, PHY 339 WRF, PHY 575 WRF, DP 1252 B2RF, DP 1050 B2RF, DP 1137 B2RF, DP 1048 B2RF, and/or DP 1137 B2RF.

As used herein, the phrase "culture filtrate" refers to broth or media obtained from cultures inoculated with a strain of fungi and allowed to grow. The media is typically filtered to remove any suspended cells, leaving the nutrients, hormones, or other chemicals.

As used herein, the term "endophyte" refers to an organism capable of living within a plant or plant tissue. An endophyte may comprise a fungal organism that may confer an increase in yield, biomass, resistance, or fitness in its host plant. Fungal endophytes may occupy the intracellular or extracellular spaces of plant tissue, including the leaves, stems, flowers, or roots.

The phrase "pest resistance" refers to inhibiting or reducing attack from pests. Pest resistance provides at least some increase in pest resistance over that which is already possessed by the plant.

As used herein, the term "genotypes" refers to the genetic constitution of a cell or organism.

As used herein, the term "phenotype" refers to the detectable characteristics of a cell or organism, which characteristics are either the direct or indirect manifestation of gene expression.

As used herein, the phrase "host plant" refers to any plant that an endophytic fungi colonizes. In certain embodiments, the host plant comprises progeny of colonized plant.

As used herein, the phrase "increased yield" refers to an increase in biomass or seed weight, seed or fruit size, seed number per plant, seed number per unit area, bushels per acre, tons per acre, kilo per hectare, carbohydrate yield, or cotton yield. Such increased yield is relative to a plant or crop that has not been inoculated with the endophyte. In certain embodiments, the increase yield is relative to other commonly used pest treatments or other methods of addressing the biotic or abiotic stress.

As used herein, the phrase "biomass" means the total mass or weight (fresh or dry), at a given time, of a plant tissue, plant tissues, an entire plant, or population of plants, usually given as weight per unit area. The term may also refer to all the plants or species in the community (community biomass).

As used herein, "sticker" refers to compounds to enhance binding of spores to the seed surface. Non-limiting examples of such compounds are alginic acid, carrageenan, dextrin, dextran, pelgel, polyethelene glycol, polyvinyl pyrrolidone, methyl cellulose, polyvinyl alcohol, or gelatin.

As used herein, an "agriculturally acceptable" excipient or carrier is one that is suitable for use in agriculture without undue adverse side effects to the plants, the environment, or to humans or animals who consume the resulting agricultural products derived therefrom commensurate with a reasonable benefit/risk ratio.

As used herein, the term "synthetic" or the phrase "synthetic combination" refers to an artificial combination that includes mycelia and/or spores of a endophyte that is or leads to an endophytic fungal-host relationship (also termed a "symbiotum") of a host plant and an endophyte. The synthetic combination may be achieved, for example, by artificial inoculation, application, or other infection of a host plant, host plant seeds, or host plant tissues with the endophyte. In addition, the combination of host plant and an endophyte may be achieved by inoculating the soil or growth media of the plant.

The present invention contemplates the use of "isolated" microbe. As used herein, an isolated microbe is a microbe that is isolated from its native environment, and carries with it an inference that the isolation was carried out by the hand of man. An isolated microbe is one that has been separated from at least some of the components with which it was previously associated (whether in nature or in an experimental setting) or occurs at a higher concentration, viability, or other functional aspect than occurring in its native environment. Therefore, an "isolated" microbe is partially or completely separated from any other substance(s) as it is found in nature or as it is cultured, propagated, stored or subsisted in naturally or non-naturally occurring environments. Specific examples of isolated microbes include partially pure microbes, substantially pure microbes and microbes cultured in a medium that is non-naturally occurring.

As used herein, a microbe is considered to be "native" to a plant or a portion of the plant, and is said to be "natively" present in the plant or a portion of plant, if that plant or portion of the plant contains the microbe, for example, in the absence of any contacting with the microbe preparation, or contains the microbe at much lower concentrations than the contacting with the microbe preparation would provide.

Some of the methods described herein allow the colonization of plant seeds by microbes. As used herein, a microbe is said to "colonize" a plant or seed when it can exist in a symbiotic or non-detrimental relationship with the plant in the plant environment, for example on, in close proximity to or inside a plant, including the seed.

A "population" of plants, as used herein, refers to a plurality of plants that were either grown from the seeds treated with the endophytes as described herein, or are progeny of a plant or group of plants that were subjected to the inoculation methods. The plants within a population are typically of the same species, and/or typically share a common genetic derivation.

EXAMPLES

Example 1

Creating Spore Suspensions and Treatment of Seeds

Cultivation of plants and endophytic fungi strains: The cotton seed variety used in particular embodiments was variety LA122 (available from All-Tex Seed, Inc., Levelland, Tex. 79336). *Paecilomyces lilacinus* and *Chaetomium globosum* were obtained from cotton plants as described (Ek-Ramos et al. 2013, PLoS ONE 8(6): e66049. doi:10.1371/journal.pone.0066049). Persons of ordinary skill in the art can obtain endophytes suitable for performing the various embodiments of the present invention by performing the procedures described therein. In short, plant samples were rinsed in tap water and surface sterilized by immersion in 70% ethanol for 5 min, 10% bleach solution for 3 min, and rinsed twice with autoclaved distilled water. Samples were blotted dry using autoclaved paper towels. Five individual surface sterilized leaves, squares and bolls (N=15 total samples) were randomly selected and imprinted onto fresh potato dextrose agar (PDA) and V8 media as a way to monitor surface sterilization efficiency. For endophyte isolation, leaves were cut in small fragments of approximately 1 $cm^2$. Squares and bolls were cut in six pieces. Any fiber present was removed and cut into six smaller pieces. Leaf fragments were placed upside down on PDA and V8 medium plates in triplicate. Each plate contained 3 leaf fragments for a total of 9 fragments assayed per plant. For squares collected early in the season, 3 slices per square were plated on PDA and V8 media as with the leaf fragments. Because of similarity in size and location within a plant, when collected later in the season, squares and bolls from a given plant were plated together on petri dishes containing two square slices, two boll slices and two pieces of fiber. Antibiotics Penicillin G (100 Units/mL) and Streptomycin (100 μg/mL) (Sigma, St Louis, Mo., USA) were added to the media to suppress bacterial growth. All plates were incubated in the dark at room temperature for, in average, two weeks until growth of fungal endophyte hyphae from plant tissues was detected.

An inclusive combination of morphological and molecular fungal endophyte identification was employed for identification. Once fungal hyphae were detected growing from the plant material, samples were taken to obtain pure fungal isolates. For identification by PCR, genomic DNA was extracted from mycelium of each isolated fungal strain, following a chloroform:isoamyl alcohol 24:1 protocol and fungal specific primers were used to amplify the ITS (Internal Transcribed Spacer) region of nuclear ribosomal DNA. This region is the primary barcoding marker for fungi and includes the ITS1 and ITS2 regions, separated by the 5.8S ribosomal gene. In order to avoid introducing biases during PCR (taxonomy bias and introduction of mismatches), it has been suggested to amplify the ITS1 region only, therefore the primers ITS1 (5' TCC GTA GGT GAA CCT GCG G 3') (SEQ ID NO:5) and ITS2 (5' GCT GCG TTC TTC ATC GAT GC 3') (SEQ ID NO:6) were used to amplify and sequence the ~240 bp ITS1 region of each one of the isolated fungal strains. The resulting sequences were aligned as query sequences with the publicly available databases GenBank nucleotide, UNITE and PlutoF. The last two are specifically compiled and used for fungi identification. Table 1 provides a list of endophytes identified and useful in the present invention. All of these endophytes belong to phylum Ascomycota, subphylum Pezizomycotina, except for *Phanerochaete crassa*, which belongs to phylum Basidiomycota, subphylum Agaricomycotina, and *Pseudozyma* sp, which belongs to phylum Basidiomycota, subphylum Ustilaginomycotina. Table 1 shows the species/genus, family, order, subclass, class, and the SEQ ID NO corresponding to the ~240 bp ITS1 region for each one of the isolated fungal strains, except for *Beauveria bassiana*, *Aspergillus parasiticus*, *Lecanicillium lecanii*, and *Paecilomyces lilacinus*, where the sequences shown includes the ITS1, ITS2, 5.8S, 18S, and 28S sequences and were obtained from the UNITE database for GenBank numbers JF837090, JX857815, FJ643076, and EU553283, respectively.

TABLE 1 endophytes identified and useful in the present invention

| Genus/Species | Family | Order | Subclass | Class | SEQ ID NO. |
|---|---|---|---|---|---|
| Acremonium alternatum | Incertaesedis | Hypocreales | Hypocreomycetidae | Sordariomycetes | 7 |
| Alternaria alternata | Pleosporaceae | Pleosporales | Pleosporomycetidae | Dothideomycetes | 8 |
| Alternaria brassicae | Pleosporaceae | Pleosporales | Pleosporomycetidae | Dothideomycetes | 9 |
| Alternaria compacta | Pleosporaceae | Pleosporales | Pleosporomycetidae | Dothideomycetes | 10 |
| Alternaria dianthi | Pleosporaceae | Pleosporales | Pleosporomycetidae | Dothideomycetes | 11 |
| Alternaria longipes | Pleosporaceae | Pleosporales | Pleosporomycetidae | Dothideomycetes | 12 |
| Alternaria mall | Pleosporaceae | Pleosporales | Pleosporomycetidae | Dothideomycetes | 13 |
| Alternaria sesami | Pleosporaceae | Pleosporales | Pleosporomycetidae | Dothideomycetes | 14 |
| Alternaria solani | Pleosporaceae | Pleosporales | Pleosporomycetidae | Dothideomycetes | 15 |
| Alternaria sp. | Pleosporaceae | Pleosporales | Pleosporomycetidae | Dothideomycetes | 16 |
| Alternaria tenuissima | Pleosporaceae | Pleosporales | Pleosporomycetidae | Dothideomycetes | 17 |
| Bipolaris spicifera | Pleosporaceae | Pleosporales | Pleosporomycetidae | Dothideomycetes | 18 |
| Cercospora canescens | Mycosphaerellaceae | Capnodiales | Dothideomycetidae | Dothideomycetes | 19 |
| Cercospora capsici | Mycosphaerellaceae | Capnodiales | Dothideomycetidae | Dothideomycetes | 20 |
| Cercospora kikuchii | Mycosphaerellaceae | Capnodiales | Dothideomycetidae | Dothideomycetes | 21 |
| Cercospora zinnia | Mycosphaerellaceae | Capnodiales | Dothideomycetidae | Dothideomycetes | 22 |
| Chaetomium globosum | Chaetomiaceae | Sordariales | Sordariomycetidae | Sordariomycetes | 23 |
| Chaetomium piluliferum | Chaetomiaceae | Sordariales | Sordariomycetidae | Sordariomycetes | 24 |
| Chaetomium sp. | Chaetomiaceae | Sordariales | Sordariomycetidae | Sordariomycetes | 25 |
| Cladosporium cladosporioides | Cladosporiaceae | Capnodiales | Dothideomycetidae | Dothideomycetes | 26 |
| Cladosporium sp. | Cladosporiaceae | Capnodiales | Dothideomycetidae | Dothideomycetes | 27 |
| Cladosporium uredinicola | Cladosporiaceae | Capnodiales | Dothideomycetidae | Dothideomycetes | 28 |
| Cochliobolus sp | Pleosporaceae | Pleosporales | Pleosporomycetidae | Dothideomycetes | 29 |
| Phanerochaete crassa | Phanerochaetaceae | Polyporales | Incertae sedis | Agaricomycetes | 30 |
| Phoma americana | Incertae sedis | Pleosporales | Pleosporomycetidae | Dothideomycetes | 31 |
| Phoma subherbarum | Incertae sedis | Pleosporales | Pleosporomycetidae | Dothideomycetes | 32 |
| Phomopsis liquidambari | Diaporthaceae | Diaporthales | Sordariomycetidae | Sordariomycetes | 33 |
| Phomopsis sp. | Diaporthaceae | Diaporthales | Sordariomycetidae | Sordariomycetes | 34 |
| Pleospora sp. | Pleosporaceae | Pleosporales | Pleosporomycetidae | Dothideomycetes | 35 |

TABLE 1-continued endophytes identified and useful in the present invention

| Genus/Species | Family | Order | Subclass | Class | SEQ ID NO. |
|---|---|---|---|---|---|
| *Pleosporaceae sp.* | Pleosporaceae | Pleosporales | Pleosporomycetidae | Dothideomycetes | 36 |
| *Preussia africana* | Sporormiaceae | Pleosporales | Pleosporomycetidae | Dothideomycetes | 37 |
| *Preussia sp.* | Sporormiaceae | Pleosporales | Pleosporomycetidae | Dothideomycetes | 38 |
| *Pseudozyma sp.* | Ustilaginaceae | Ustilaginales | Ustilaginomycetidae | Ustilaginomycetes | 39 |
| *Pyrenophora teres* | Pleosporaceae | Pleosporales | Pleosporomycetidae | Dothideomycetes | 40 |
| *Colletotrichum capsici* | Glomerellaceae | Incertae sedis | Sordariomycetidae | Sordariomycetes | 41 |
| *Coniolariella gamsii* | Incertae sedis | Xylariales | Xylariomycetidae | Sordariomycetes | 42 |
| *Coniothyrium aleuritis* | Coniothyriaceae | Pleosporales | Pleosporomycetidae | Dothideomycetes | 43 |
| *Coniothyrium sp.* | Coniothyriaceae | Pleosporales | Pleosporomycetidae | Dothideomycetes | 44 |
| *Corynespora cassiicola* | Corynesporascaceae | Pleosporales | Pleosporomycetidae | Dothideomycetes | 45 |
| *Diaporthe sp.* | Diaporthaceae | Diaporthales | Sordariomycetidae | Sordariomycetes | 46 |
| *Diatrype sp.* | Diatrypaceae | Xylariales | Xylariomycetidae | Sordariomycetes | 47 |
| *Drechslerella dactyloides* | Orbiliaceae | Orbiliales | Orbiliomycetidae | Orbiliomycetes | 48 |
| *Embellisia indefessa* | Pleosporaceae | Pleosporales | Pleosporomycetidae | Dothideomycetes | 49 |
| *Epicoccum nigrum* | Pleosporaceae | Pleosporales | Pleosporomycetidae | Dothideomycetes | 50 |
| *Epicoccum sp.* | Pleosporaceae | Pleosporales | Pleosporomycetidae | Dothideomycetes | 51 |
| *Exserohilum rostratum* | Pleosporaceae | Pleosporales | Pleosporomycetidae | Dothideomycetes | 52 |
| *Fusarium chlamydosporum* | Nectriaceae | Hypocreales | Hypocreomycetidae | Sordariomycetes | 53 |
| *Fusarium sp.* | Nectriaceae | Hypocreales | Hypocreomycetidae | Sordariomycetes | 54 |
| *Gibellulopsis nigrescens* | Plectosphaerellaceae | Incertae sedis | Hypocreomycetidae | Sordariomycetes | 55 |
| *Gnomoniopsis sp.* | Glomerellaceae | Incertae sedis | Hypocreomycetidae | Sordariomycetes | 56 |
| *Lewia infectoria* | Pleosporaceae | Pleosporales | Pleosporomycetidae | Dothideomycetes | 57 |
| *Mycosphaerella coffeicola* | Mycosphaerellaceae | Capnodiales | Dothideomycetidae | Dothideomycetes | 58 |
| *Mycosphaerellaceae sp.* | Mycosphaerellaceae | Capnodiales | Dothideomycetidae | Dothideomycetes | 59 |
| *Nigrospora oryzae* | Incertae sedis | Trichosphaeriales | Incertae sedis | Sordariomycetes | 60 |
| *Nigrospora sp.* | Incertae sedis | Trichosphaeriales | Incertae sedis | Sordariomycetes | 61 |
| *Nigrospora sphaerica* | Incertae sedis | Trichosphaeriales | Incertae sedis | Sordariomycetes | 62 |
| *Paecilomyces sp.* | Trichocomaceae | Eurotiales | Eurotiomycetidae | Eurotiomycetes | 63 |
| *Penicillium citrinum* | Trichocomaceae | Eurotiales | Eurotiomycetidae | Eurotiomycetes | 64 |
| *Retroconis sp.* | Incertae sedis | Incertae sedis | Incertae sedis | Incertae sedis | 65 |
| *Rhizopycnis sp.* | Incertae sedis | Incertae sedis | Incertae sedis | Dothideomycetes | 66 |
| *Schizothecium inaequale* | Lasiosphaeriaceae | Sordariales | Sordariomycetidae | Sordariomycetes | 67 |
| *Stagonospora sp.* | Phaeosphaeriaceae | Pleosporales | Pleosporomycetidae | Dothideomycetes | 68 |
| *Stemphylium lancipes* | Pleosporaceae | Pleosporales | Pleosporomycetidae | Dothideomycetes | 69 |
| *Thielavia hyrcaniae* | Chaetomiaceae | Sordariales | Sordariomycetidae | Sordariomycetes | 70 |
| *Thielavia sp.* | Chaetomiaceae | Sordariales | Sordariomycetidae | Sordariomycetes | 71 |
| *Ulocladium chartarum* | Pleosporaceae | Pleosporales | Pleosporomycetidae | Dothideomycetes | 72 |
| *Verticillium sp.* | Plectosphaerellaceae | Incertae sedis | Hypocreomycetidae | Sordariomycetes | 73 |
| *Beauveria bassiana* | Cordycipitaceae | Hypocreales | Hypocreomycetidae | Sordariomycetes | 74 |
| *Aspergillus parasiticus* | Trichocomaceae | Eurotiales | Eurotiomycetidae | Eurotiomycetes | 75 |
| *Lecanicillium lecanii* | Cordycipitaceae | Hypocreales | Hypocreomycetidae | Sordariomycetes | 76 |
| *Paecilomyces lilacinus* | Trichocomaceae | Eurotiales | Eurotiomycetidae | Eurotiomycetes | 77 |

TABLE 1 List of Endophytes:

*Acremonium alternatum, Alternaria alternata, Alternaria brassicae, Alternaria compacta, Alternaria dianthi, Alternaria longipes, Alternaria mali, Alternaria sesami, Alternaria solani, Alternaria* sp., *Alternaria tenuissima, Ascomycota* sp., *Bipolaris spicifera, Cercospora canescens, Cercospora capsici, Cercospora kikuchii, Cercospora zinnia, Chaetomium globosum, Chaetomium piluliferum, Chaetomium* sp., *Cladosporium cladosporioides, Cladosporium* sp., *Cladosporium uredinicola, Cochliobolus* sp, *Phanerochaete crassa, Phoma americana, Phoma subherbarum, Phomopsis liquidambari, Phomopsis* sp., *Pleospora* sp., *Pleosporaceae* sp., *Polyporales* sp., *Preussia africana*, *Preussia* sp., *Pseudozyma* sp., *Pyrenophora teres*, *Colletotrichumcapsici*, *Coniolariella gamsii*, *Coniothyrium aleuritis*, *Coniothyrium* sp., *Corynespora cassiicola*, *Diaporthe* sp., *Diatrype* sp., *Drechslerella dactyloides*, *Embellisia indefessa*, *Epicoccum nigrum*, *Epicoccum* sp., *Exserohilum rostratum*, *Fusarium chlamydosporum*, *Fusarium* sp., *Gibellulopsis nigrescens*, *Gnomoniopsis* sp., *Lewia infectoria*, *Mycosphaerella coffeicola*, *Mycosphaerellaceae* sp., *Nigrospora oryzae*, *Nigrospora* sp., *Nigrospora sphaerica*, *Paecilomyces* sp., *Penicillium citrinum*, *Retroconis* sp., *Rhizopycnis* sp., *Schizothecium inaequale*, *Stagonospora* sp., *Stemphylium lancipes*, *Thielavia hyrcaniae*, *Thielavia* sp., *Ulocladium chartarum*, *Verticillium* sp., *Beauveria bassiana*, *Aspergillus parasiticus*, *Lecanicillium lecanii*, *Paecilomyces lilacinus*.

*Beauveria bassiana* was cultured from a commercially obtained strain (available from Botanigard). *Beauveria bassiana*, *Paecilomyces lilacinus*, and *Chaetomium globosum* were cultured on potato dextrose agar media (PDA). Stock spore concentration solutions of each fungi were made by adding 10 ml of sterile water to the fungi plates and scraping them free of the agar with a sterile scalpel. The resulting mycelia and spores obtained were then filtered into a sterile beaker utilizing a cheese cloth to filter out the mycelia, thereby creating stock solutions. A haemocytometer was used to measure and calculate spore concentrations of the stock solutions. The desired concentrations were created by dilution, and seeds were placed into spore suspensions with the desired spore concentrations. In various embodiments, the final treatment concentrations can be about $10^2$, $10^3$, $10^4$, $10^5$, $10^6$, $10^7$, $10^8$, or $10^9$ spores/ml which can be reached by serial dilutions in sterile water or in an appropriate solution or buffer.

For seed inoculation, the seeds were surface sterilized prior to soaking them in spore suspensions with the desired concentration by immersion the seeds in 70% ethanol for 3 minutes with constant shaking followed by incubation in 2% NaOCl for 3 minutes; followed by three washes in sterile water. The third sterile water wash was plated onto potato dextrose agar media (PDA) to confirm that surface sterilization was effective. Seeds were then soaked for 24 hours in beakers containing spore suspensions with two different concentrations of fungi. Control group seeds were treated with sterile water only. Spore concentrations for *Beauveria bassiana* were zero (control), $1\times10^6$ (treatment 1) and $1\times10^9$ (treatment 2) and for *Paecilomyces lilacinus* or *Chaetomium globosum* were zero (control), $1\times10^6$ (treatment 1) and $1\times10^7$ (treatment 2). These beakers were incubated for 24 hours at 32° C. in a culture chamber until next day for planting (24 hr).

Soaked seeds were planted in L22 mix soil (Borlaug Institute, Texas A&M). All plants were grown in a laboratory greenhouse at ~28° C. with a natural light photoperiod. There was no fertilization of the plants, and watering was done consistently across all treatments as needed.

Direct seed inoculation: In particular embodiments, individual seeds and the surrounding soil can be directly inoculated with the spore solution ($10^2$-$10^3$, $10^3$-$10^4$, $10^4$-$10^5$, $10^6$-$10^7$, or $10^7$-$10^8$ spores/ml) at planting before covering the seed with soil.

In various embodiments, any seed or plant treatments that are suitable for application of biological agents to seeds or plants and known to persons having ordinary skill in the art can be employed.

Example 2

Application of Endophyte Spores as a Dry Powder Composition

In addition to application of a spore solution for seed treatment, the endophytes or endophyte spores can also be applied as dry powder or using a sicker such as methyl cellulose for seed treatment. In certain embodiments, the concentration may be at least $10^5$, $10^6$, $10^7$, $10^8$, $10^9$, or higher colony forming units or spores/g dry weight.

In certain embodiments, endophytes can be grown in fungi cultivation media in a fermenter. Endophytic mycelial fragments or spores can be collected, dried and ground. A sticker such as caboxymethyl cellulose may also be added to the ground endophytic material.

In certain embodiments the weight ratio between endophytic material and sticker may be between 1:10-50, 1:50-100, 1:100-500, or 1:500-1000 to obtain the seed coating or seed inoculation material. This seed inoculation material can be applied to seeds. In various embodiments, the weight ratio between seed inoculation material and seed may be 1:10-50, 1:50-100, 1:100-500, 1:500-1000, or 1:1000-5000.

Example 3

Soil (in Furrow) Endophyte Treatments

Soil drench (in furrow) application may be performed by applying an endophyte composition to the surface of the soil and/or seed during planting. In particular embodiments, the endophyte composition may comprise an endophyte suspension or an endophyte dry powder formulation. In various embodiments the endophyte may comprise mycelia and/or spores. In particular embodiments, the soil drench application may comprise applying the endophyte composition to the surface of the soil directly above each seed. In certain embodiments, the endophyte composition may comprise 0.01-0.1, 0.1-1, or 1-10 ml endophyte suspension, which may be a endophyte spore suspension.

Soil inoculation: In certain embodiments, seeds can be planted into inoculated soil. The inoculum can be obtained by multiplying the endophyte on fungal growth media. The fungal growth media can be potato dextrose agar media (PDA). In other embodiments the fungal growth media can be as wheat grain. In a non-limiting example, 100 g of wheat grain can be washed and soaked overnight in sterile water. Excess water can be drained, seeds dried on paper towel, packed in a 500 ml conical flask and autoclaved at 15 psi for 1 h. One milliliter of the endophytic fungal spore suspension ($10^7$ spores/ml) can be inoculated to the flask, and the cultures can be incubated at 25° C. for 2 weeks. To avoid clumping, the flasks can be shaken vigorously to separate the grain and break the mycelial mat. Approximately 5 g of inoculum can be placed in soil at planting. In certain embodiments, the inoculum can be placed in the soil at the same time or within 1 month of planting the seeds. In certain embodiments, the seeds may comprise sterilized seeds.

Example 4

Foliar Endophyte Treatments

Plants were inoculated via foliar application at the third true leaf stage by spraying the surface of fully expanded leaves to run-off with a spore suspension ($10^8$ spores/ml) using a hand-held plastic sprayer (1 L). In certain embodiments, endophyte spore suspensions were made in water. In certain embodiments, the water was supplemented with a detergent. In a particular non-limiting example, the spore suspension contained 0.02% Triton X 100 as a detergent.

Foliar endophyte treatment may be performed using any suitable method known to a person having ordinary skill in the art. In particular, foliar endophyte treatment may be performed using a sprayer by directly spraying leaves with an endophyte suspension, which may be a endophyte spore suspension.

Figure 9:
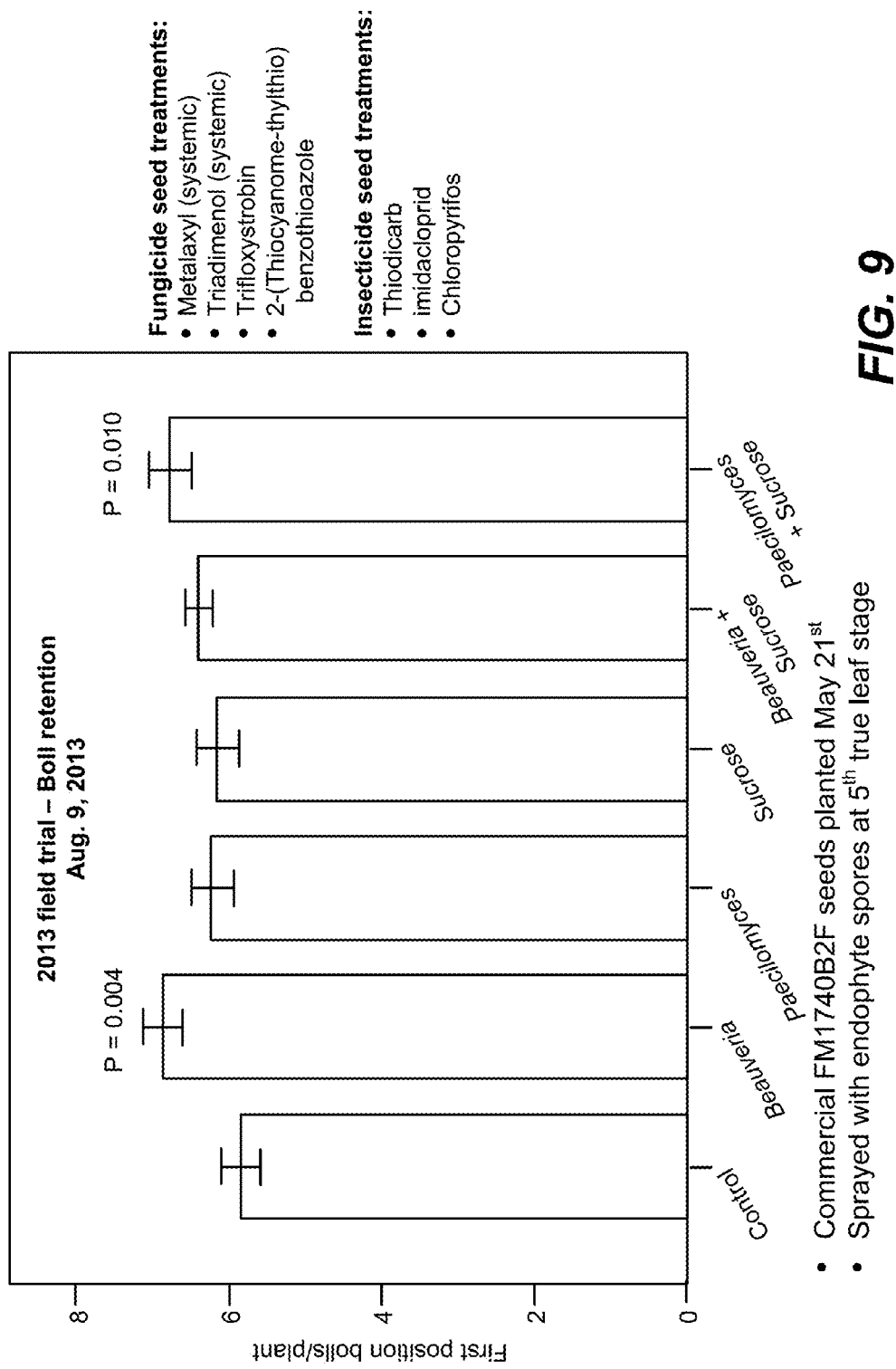
FIG. 9: Foliar application of cotton in the field with spores of endophytic entomopathogenic fungi improves plant performance. Cotton (variety FM1740B2F) seeds treated with a variety of typical fungicide (Metalaxyl, Triadimenol, Trifloxystrobin, 2-(Thiocyanome-thylthio)benzothioazole) and insecticide (Thiodicarb, Imidacloprid, Chloropyrifos) seed treatments were planted and grown under field conditions. The plants were sprayed at the 5th true leaf stage with aqueous solutions of *Beauveria bassiana* and *Paecilomyces fumosoroseus*. Sucrose was included (1% wt/vol) as an additional nutritional resource for the fungi. Significantly higher first position boll (developing fruit) retention was observed in plants sprayed with *Beauveria bassiana* without sucrose and *Paecilomyces fumosoroseus* plus sucrose.

FIG. 9 demonstrates that foliar application of cotton in the field with spores of endophytic entomopathogenic fungi improved plant performance. Cotton (variety FM1740B2F) seeds were treated with a variety of typical fungicide (Metalaxyl, Triadimenol, Trifloxystrobin, 2-(Thiocyanome-thylthio)benzothioazole) and insecticide (Thiodicarb, Imidacloprid, Chloropyrifos), and seed treatments were planted and grown under field conditions. The plants were sprayed at the 5th true leaf stage with aqueous solutions of *Beauveria bassiana* and *Paecilomyces fumosoroseus*. Sucrose was included (1% wt/vol) as an additional nutritional resource for the fungi. Significantly higher first position boll (developing fruit) retention was observed in plants sprayed with *Beauveria bassiana* without sucrose and *P. fumosoroseus* plus sucrose.

Example 5

Confirmation of Plant Colonization by Endophytic Fungi

Plants were individually placed in plastic bags, which were labeled with plant number, treatment, and final aphid number, and stored in 4° C. until the next day for endophyte confirmation. Half of each plant was utilized for plating on PDA agar and the other half was freeze-dried for to conduct diagnostic PCR assays for endophyte confirmation. The surface sterilization protocol and plating of third sterile water wash on PDA to test for surface contamination was conducted as described above. For diagnostic PCR assays, plant tissue was freeze-dried and DNA was extracted utilizing the CTAB protocol (Doyle & Doyle, 1987, Phytochemistry Bulletin 19:11-15). The oligonucleotide primer sequences synthesized were based upon a NCBI BLAST search corresponding to the laboratory culture sequence results isolated (Ek-Ramos et al., 2013). Sense and antisense oligonucleotide sequences for *Beauveria bassiana* were: 5'-CGGCGGACTCGCCCCAGC-CCG-3' (SEQ ID NO:1) and 5'-CCGCGTCGGGGTTCCG-GTGCG-3' (SEQ ID NO:2) respectively. The oligonucleotides used to amplify *Paecelomyces lilacinus* were: 5' CTCAGTTGCCTCGGCGGGAA 3' (SEQ ID NO:3) and 5' GTGCAACTCAGAGAAGAAATTCCG 3' (SEQ ID NO:4).

The PCR protocol consisted of a denaturation step at 95° C. for 5 min, followed by alignment of oligonucleotides at 56° C. for 2 min and an extension step of 7 min at 72° C. with a total of 35 cycles. The PCR products were visualized in a 2% agarose gel containing 1% ethidium bromide. Electrophoresis was performed at 70 volts for 30 min.

Example 6

Endophytic Fungi can be Manipulated in the Field

A field trial using isolates of *Paecilomyces lilacinus* and *Beauveria bassiana* was conducted during the summer. A randomized block design with five replicate plots that were planted with seeds that were inoculated by soaking for 9 hr in three different aqueous spore concentrations (0, $10^6$, or $10^8$ spores/ml) of the candidate endophyte (such as *Paecilomyces lilacinus* or *Beauveria bassiana*). Each plot consisted of four 15.24 m (40 ft) rows, each separated by 101.6 cm (40 in).

Colonization efficiency: At the first true leaf stage, four plants from each plot for a total of 20 plants per treatment were randomly sampled and tested for colonization by each of the candidate endophytes. Colonization frequencies were determined by incubating surface sterilized root, stem and leaf fragments on PDA media and observing for fungal growth. Colonization frequencies are reported as the number of plants per treatment group with at least one positively colonized plant fragment.

The high endophytic colonization frequency of seedlings by *Paecilomyces lilacinus* or *Beauveria bassiana* demonstrates that the presence of specific endophytes can be manipulated under field planting conditions (FIG. 1).

Example 7

Cotton Aphid Reproduction Test

Figure 4A:
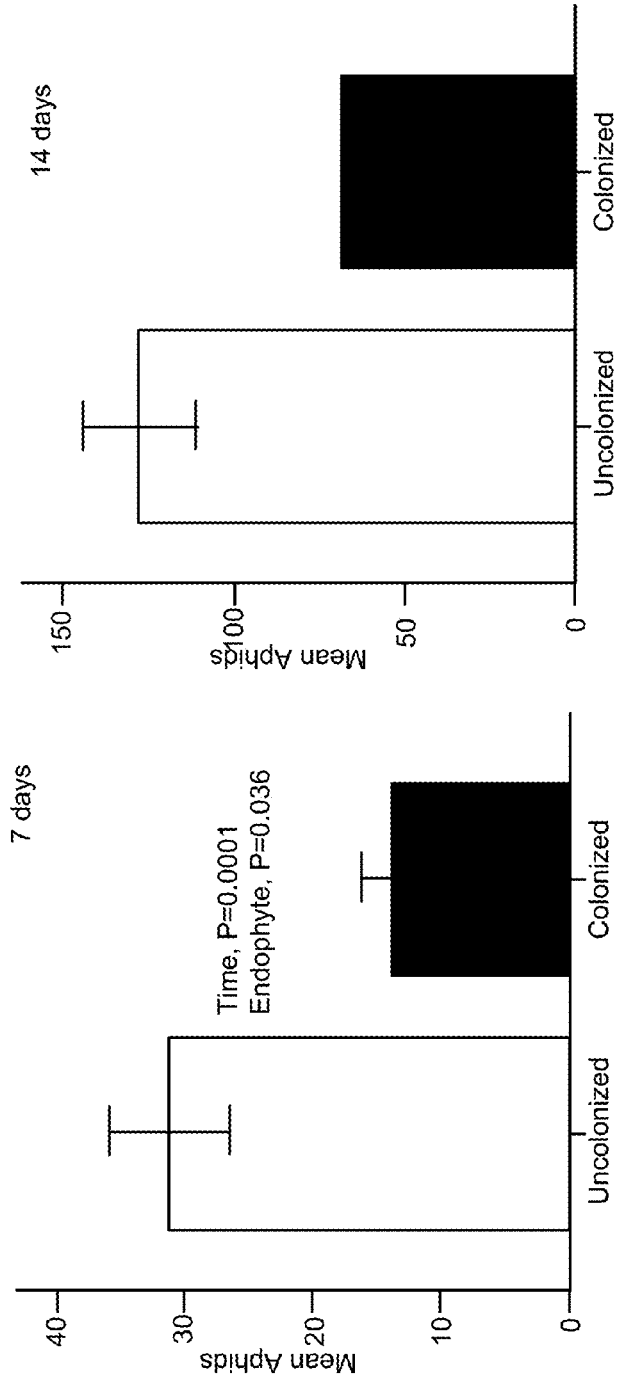
FIGS. 4A, 4B: The effect of endophytic fungi on cotton aphids (*Aphis gossypii*) reproduction.
Figure 4B:
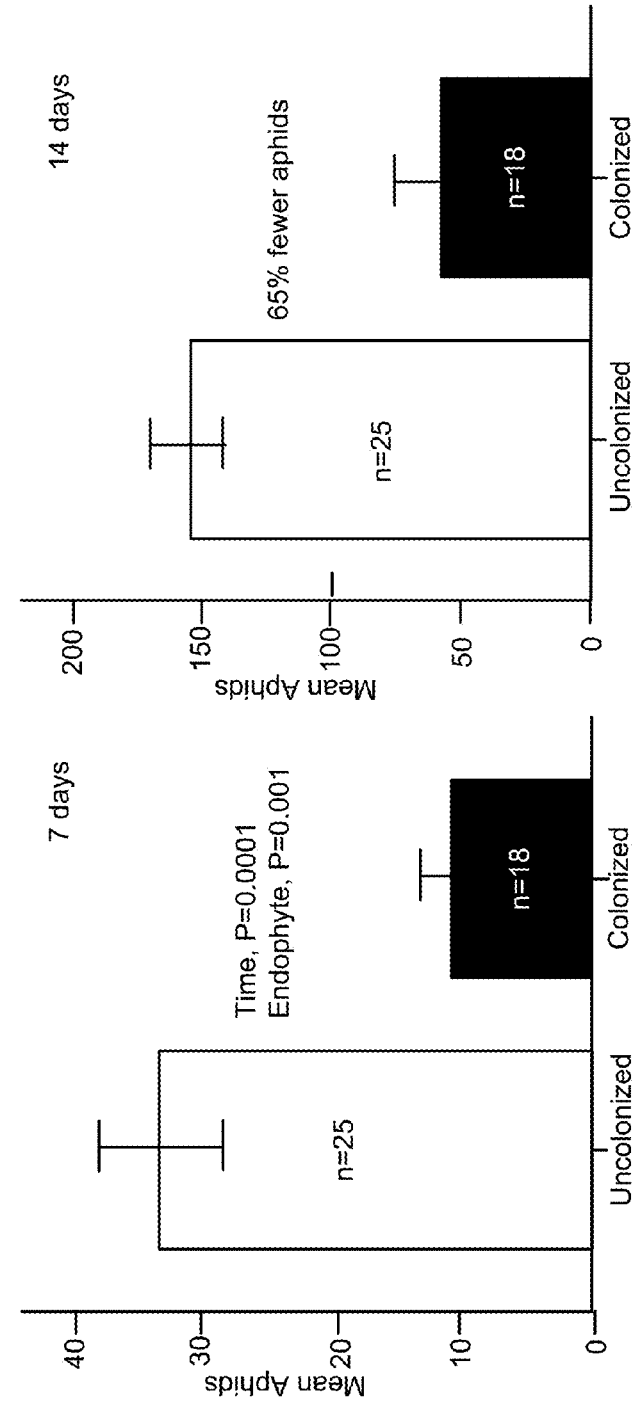
Figure 5:
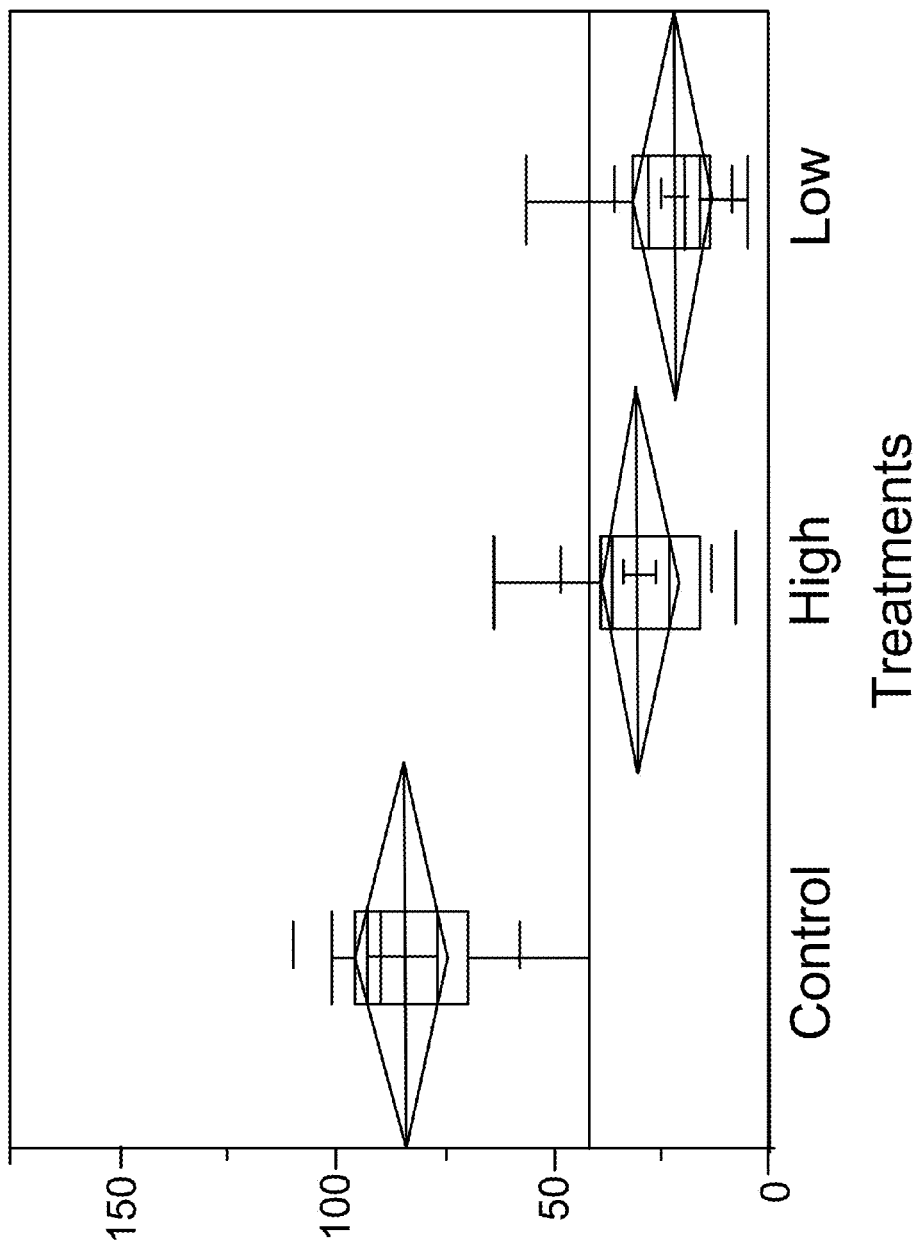
FIG. 5: Effects of *Chaetomium globosum* on cotton aphids. Endophytic *Chaetomium globosum* in cotton negatively affects cotton aphid population growth rates as evidenced by reduced reproduction after 14 days on endophyte-colonized versus control plants. Cotton plants were grown from seeds treated by soaking in spore solutions of 0 (control), $10^6$ (low) and 108 (high) spores/ml.

A colony of *A. gossypii* was reared on cotton in cages in a greenhouse kept at approximately 28° C. with natural light photoperiod. Second instar nymphs were placed directly onto endophyte-treated cotton plants and control plants. Ten plants were utilized per treatment group and ten aphids were placed per plant. After plants were inoculated with the aphids, the plants were placed in individual plastic 45×20 cm cups and sealed with no-see-um mesh (Eastex products, NJ) to avoid aphid movement from plant to plant. In one embodiment, the plants used were 13 days old, approximately in the first true leaf stage, and aphids were left to reproduce for seven days under greenhouse conditions. In another embodiment, aphids were left to reproduce for 14 days on plants initially 20 days old at the beginning of the experiment, approximately in the third true leaf stage. At the end of each embodiment, aphid numbers were counted and recorded per individual plant. The presence of *Beauveria bassiana* or *Paecilomyces lilacinus* as an endophyte in cotton significantly reduced the reproduction of cotton aphids on endophyte treated plants versus untreated control plants (FIG. 4A, 4B, and FIG. 5)

Example 8

Fungal Endophytes Reduce Nematode Reproduction

Plants were germinated from treated and untreated control seeds in an environment chamber and then transplanted to soil in pots 11 days after planting. Two replicate seedlings per treatment were sampled to examine the endophyte colonization efficiency by surface sterilization and plating on PDA agar. Nematode treatment group seedlings were treated with either 2,000 or 10,000 eggs/plant at day six after transplanting. Plants were harvested and processed 6 weeks after nematode inoculation. The numbers of galls per gram of root tissue and total egg numbers in the population for each plant were quantified to compare nematode performance between endophyte-treated and untreated (control) plants.

Figure 2:
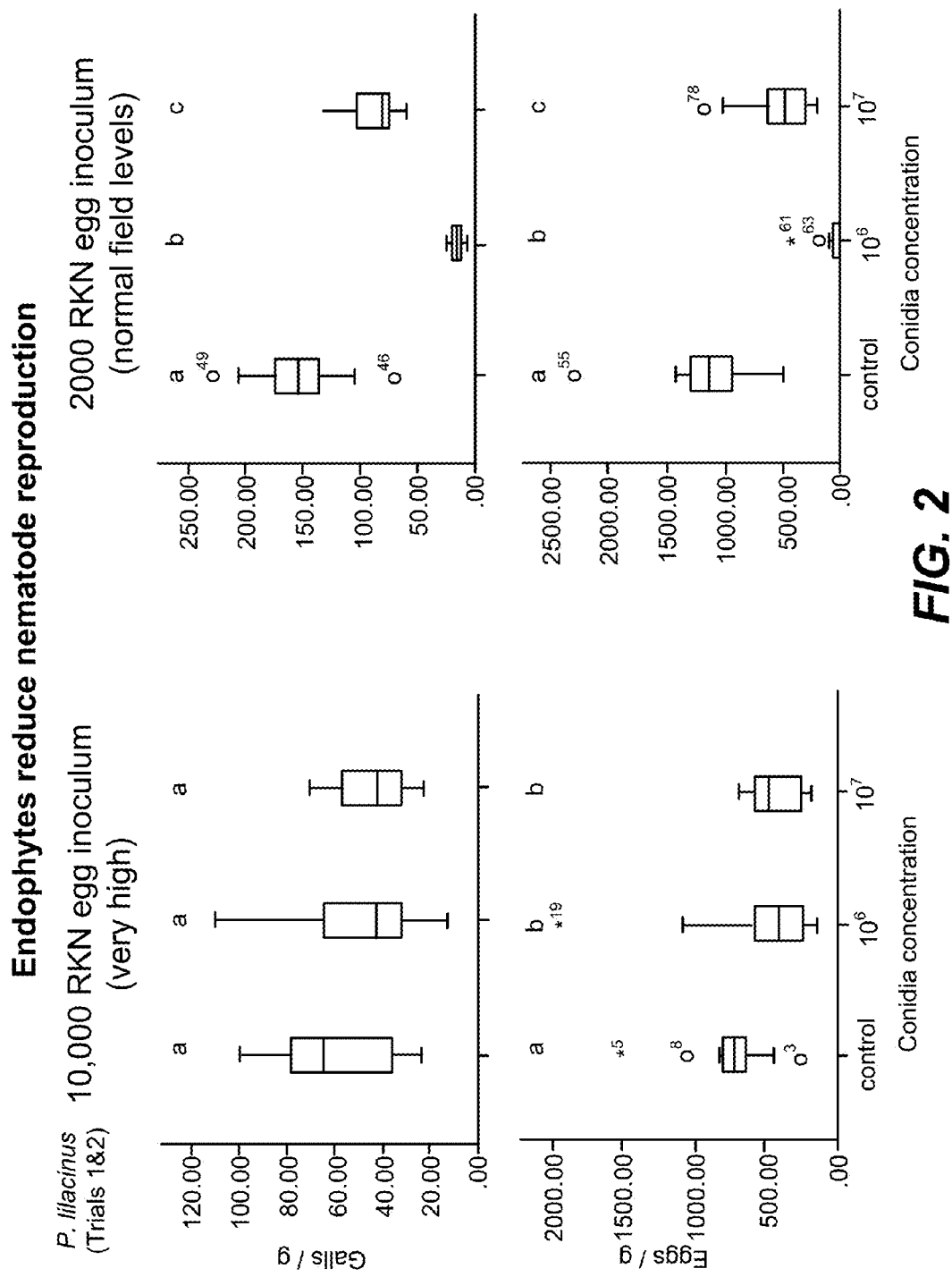
FIG. 2: The endophytic fungus *Paecilomyces lilacinus* negatively affects root knot nematode (*Meloidogyne incognita*) reproduction when present as an endophyte in cotton. At high nematode inoculum levels (10,000 eggs), the endophyte reduced egg production in plants following treatment of seeds with solutions containing either $10^6$ or $10^7$ spores/ml when compared to untreated control seeds. At field inoculum levels (2000 eggs), the presence of the endophyte significantly reduced both galls and egg production at both seed treatment concentrations.
Figure 3:
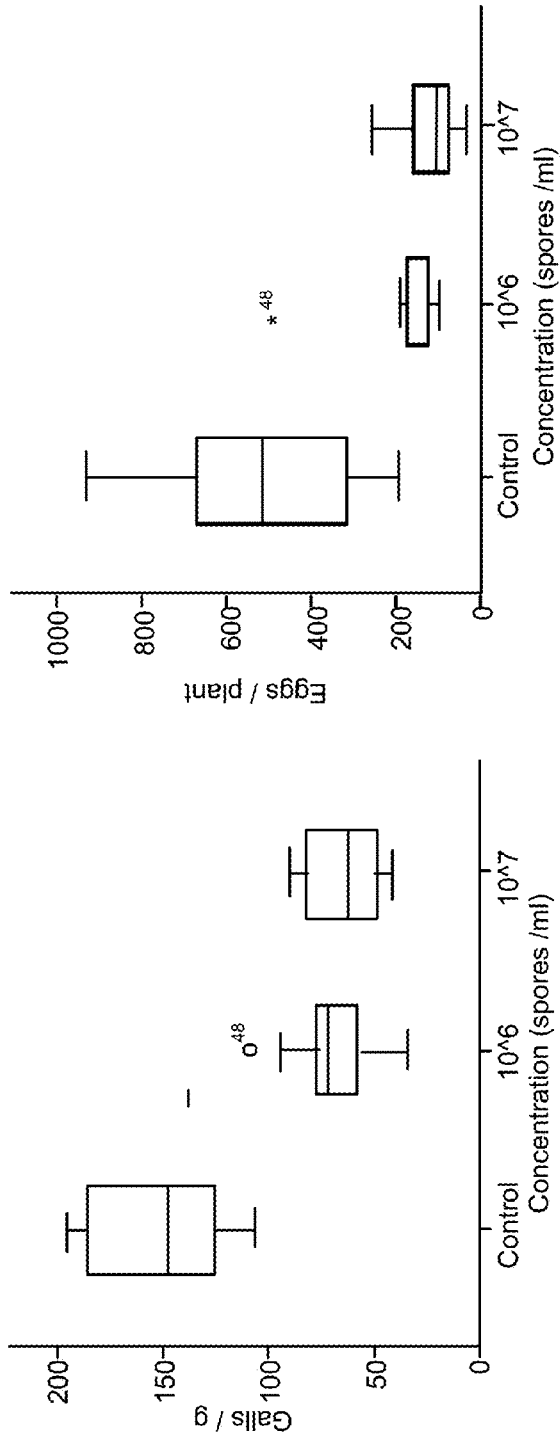
FIG. 3: Endophytic *Chaetomium globosum* negatively affects root-knot nematode reproduction. Negative effects of endophytic *Chaetomium globosum* on root-knot nematode gall formation and egg production following cotton seed soaking treatments in solutions of 0 (untreated controls), $10^6$ and $10^8$ spores/ml. Seedlings were inoculated with 1000 nematode eggs and grown in the greenhouse. Egg production by hatching nematodes that successfully infected the seedlings was quantified 60 days later.

FIGS. 2 and 3 demonstrate that the endophytic fungi *Paecilomyces lilacinus* and *Chaetomium globosum* negatively affected root knot nematode (*Meloidogyne incognita*) reproduction when present as an endophyte in cotton. At high nematode inoculum levels (10,000 eggs), *Paecilomyces lilacinus* reduced egg production in plants following treatment of seeds with solutions containing either $10^6$ or $10^7$ spores/ml when compared to untreated control seeds. At field inoculum levels (2000 eggs), the presence of *Paecilomyces lilacinus* significantly reduced both galls and egg production at both seed treatment concentrations. Endophytic *Chaetomium globosum* negatively affects root-knot nematode reproduction. Negative effects of endophytic *Chaetomium globosum* on root-knot nematode gall formation and egg production were demonstrated following cotton seed soaking treatments in solutions of 0 (untreated controls), $10^6$ and $10^8$ spores/ml.

Example 9

Effect of Fungal Endophytes on Insects

Endophyte-treated and control plants were grown from non-transgenic cotton seeds (*Gossypium hirsutum*)(variety LA122, AllTex Seed Co.). Seeds were soaked for 24 hours in beakers containing $10^8$ spores/ml solutions of the fungi utilized plus sterile water-only as a control. The beakers were placed in a 32° C. culture chamber overnight (approx. 9 h) until planting the next day. The plants were grown under both greenhouse and field conditions. Greenhouse plants were first germinated in seedling trays and then transferred to 30 cm pots. Field grown plants were concurrently planted and grown.

Behavioral assays: No-choice and choice behavioral assays were conducted to compare the response of western tarnished plant bugs (*L. hesperus*) and green stink bugs (*N. viridula*) to squares and bolls from endophyte-treated and untreated plants. The assays were conducted at 30° C. in 10 cm diameter petri dishes with a thin layer of 2% agar on the bottom to provide moisture for the squares (*L. hesperus* assays) and bolls (*N. viridula* assays) from experimental plants offered to the insects during the observations. For no-choice assays, a single square or boll was inserted by the base into the agar in the center of the dish. A single young adult (1-7 days post molt) insect was placed in each dish and covered with the top. A total of 30 insects were observed in each trial with N=10 insects each in the *Beauveria bassiana*, *Paecilomyces lilacinus* and control treatment groups. The *L. hesperus* no-choice trials were replicated four times (N=40 per treatment) with squares from greenhouse grown plants used in all but one trial. The *N. viridula* no-choice trials were replicated three times (N=20 per treatment) with bolls from greenhouse grown plants used in one trial.

Choice tests were conducted under the similar conditions using the same arenas, but with two equal sized squares (*L. hesperus*) or bolls (*N. viridula*) placed 4 cm apart in the center of the petri dish. The two squares or bolls per arena were from an untreated control plant and either a *Beauveria bassiana* or *Paecilomyces lilacinus* treated plant. A total of 20 insects were observed in each trial, with N=10 each in the *Beauveria bassiana* vs. control and *Paecilomyces lilacinus* vs. control treatment groups. The *L. hesperus* and *N. viridula* choice trials were both replicated twice (N=20 per treatment) with squares from field-grown plants in all trials.

Insects were observed for 6 hours per trial using a point sampling procedure for both the no-choice and choice assays. Preliminary observations indicated that the insects of both species were more active at the beginning of the assay, thus staged sampling schedule was adopted with observations recorded at 5 minute intervals early in the assay (0-60 min), 15 minute intervals in the middle (61-180 min) and 30 minute intervals late (181-360 min) in the assay. At each sampling interval, the insects were recorded as either off the square/boll or feeding or roosting upon the square/boll.

Data analysis: In the no-choice assays, the proportion of insects observed either feeding or resting upon cotton squares (*L. hesperus*) or bolls (*N. viridula*) was compared between treatment groups at each observation point across the duration of the assay using the Wilcoxon Signed Ranks Test. To test for variation in responses over time, for each individual the proportion of observations either feeding or upon the plant sample was calculated for early (0-60 min), middle (61-180 min) and late (181-360 min) periods of the assay and compared across treatment groups using a repeated measures analysis of variance (ANOVA) with the endophyte treatment group as the main factor and time as the repeat effect. The observed frequency of individuals failing to make contact with squares or bolls from endophyte-treated plants was compared to the expected frequency of individuals failing to do so based on the control group using a X2 test. Among the insects that did make contact with either a square or boll, the time to first contact (latency) was compared among treatment groups using a one-way ANOVA. All analyses including tests of normality and homogeneity of variances were conducted in SPSS 21 (SPSS Inc.).

Results of the *L. hesperus* no-choice assays: Over the duration of the assay, a significantly higher proportion of *L. hesperus* individuals over time was observed in contact with and feeding upon squares from untreated control plants relative to those from either of the *Beauveria bassiana* or *Paecilomyces lilacinus* endophyte treatment groups (Wilcoxon Signed Ranks test, P<0.0001 for both comparisons) (FIG. 6A). Repeated measures ANOVA indicated a significant effect of time ($F_{1,116}$=86.175; P<0.001) with a higher proportion of insects contacting the square as the assay progressed (FIG. 6B). There was also a significant effect of endophyte treatment ($F_{2,116}$=4.929; P=0.009) with no significant time X endophyte treatment interaction ($F_{2,116}$=1.015; P=0.366). Of the 40 insects in each treatment group, 12.5% of the control group failed to make contact with the square over the course of the assay, while a significantly higher 35% and 32.5% the *Beauveria bassiana* and *Paecilomyces lilacinus* treatment group insect respectively failed to make contact (X2 test, P<0.0001). Among the insects that did make contact with a square, there was significant difference in the latency to first contact among the treatment groups ($F_{2,85}$=7.225; P<0.0001) with the control group exhibiting a shorter latency to contact than either the *Beauveria bassiana* (posthoc LSD test; P=0.001) or *Paecilomyces lilacinus* endophyte treatment groups (posthoc LSD test; P=0.006 (FIG. 6A).

Results of the *L. hesperus* choice assays: In simultaneous choice tests, *L. hesperus* individuals selected squares from untreated control plants more often than those from endophyte-treated plants. Response ratios were significantly greater than 0.5 over the duration of the assays, indicating that the insects non-randomly selected bolls from control plants over bolls from plants endophytically colonized by either (A) *Beauveria bassiana* (P<0.0001; Wilcoxon Signed Ranks test) or (B) *Paecilomyces lilacinus* (P<0.0001; Wilcoxon Signed Ranks test)(FIG. 6B).

Figure 7A:
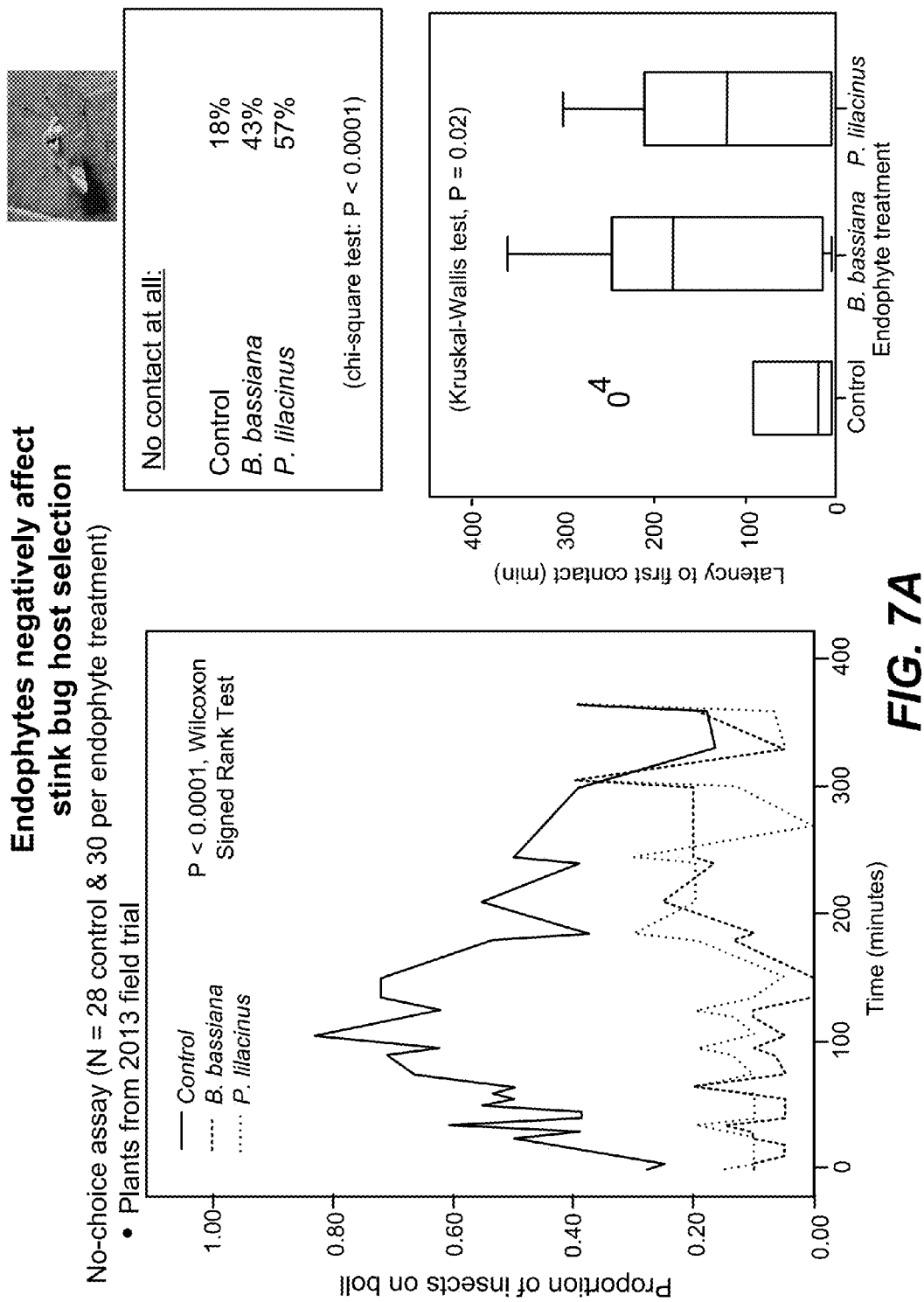
FIGS. 7A, 7B: The effect of the endophytic fungi *Beauveria bassiana* and *Paecilomyces lilacinus* on southern green stink bugs (*Nezara viridula* (Pentatomidae).
Figure 7B:
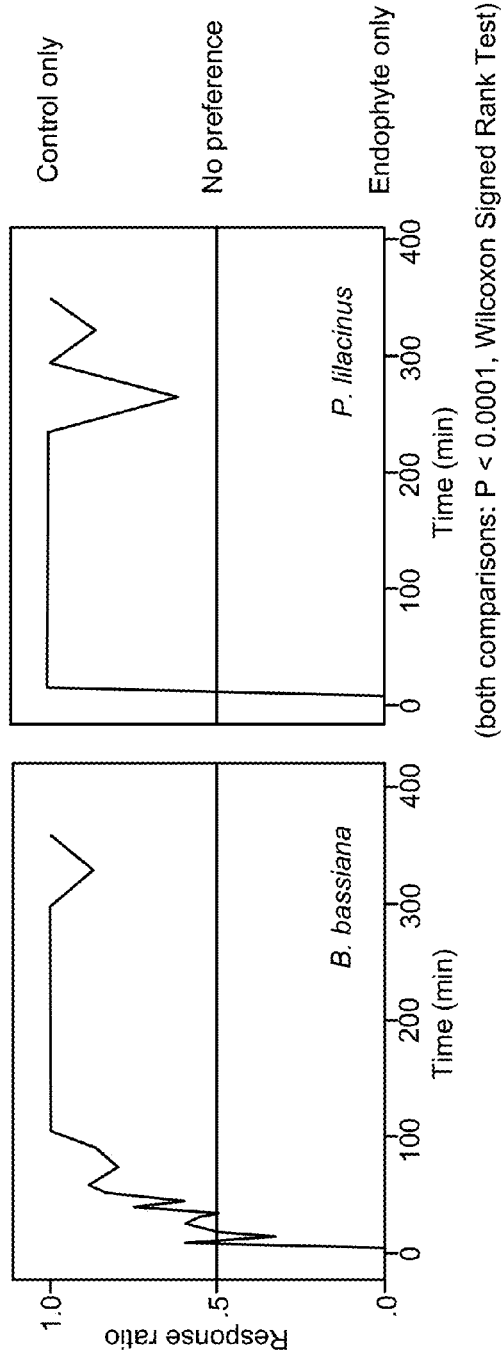

Results of the *N. viridula* no-choice assays: Over the duration of the assay, a significantly higher proportion of *N. viridula* individuals over time was observed in contact with and feeding upon bolls from untreated control plants relative to those from either of the *Beauveria bassiana* or *Paecilomyces lilacinus* endophyte treatment groups (Wilcoxon Signed Ranks test, P<0.0001 for both comparisons)(FIG. 7A). Repeated measures ANOVA indicated a significant effect of time ($F_{1,116}$=86.175; P<0.001) with a higher proportion of insects contacting the square as the assay progressed (FIG. 1), There was also a significant effect of endophyte treatment ($F_{2,116}$=4.929; P=0.009) with no significant time X endophyte treatment interaction ($F_{2,116}$=1.015; P=0.366). Of the 40 insects in each treatment group, 12.5% of the control group failed to make contact with the square over the course of the assay, while a significantly higher 35% and 32.5% the *Beauveria bassiana* and *Paecilomyces lilacinus* treatment group insect respectively failed to make contact (X2 test, P<0.0001). Among the insects that did make contact with a square, there was significant difference in the latency to first contact among the treatment groups ($F_{2,85}$=7.225; P<0.0001) with the control group exhibiting a shorter latency to contact than either the *Beauveria bassiana* (posthoc LSD test; P=0.001) or *Paecilomyces lilacinus* endophyte treatment groups (posthoc LSD test; P=0.006 (FIG. 7B).

Example 10

More Bolls are Retained after Endophyte Treatment

During the field trial, cotton phenology and development was quantified using a plant mapping and information system developed specifically for cotton to track fruit development and retention by the plant as a means of monitoring plant development and stress (COTMAN™, Cotton Inc.). One measure of cotton stress is the retention of developing flowers (squares) and fruits (bolls) in the first fruiting position on branches. First position squares and bolls were measured on 5 plants per row in two rows in each of the five replicate plots (N=10 plants per plot) for each treatment group.

FIG. 10 demonstrates that early in the growing season as flowers begin to develop, a trend for higher square retention in the endophyte-treated plants relative to controls was observed. This trend continued later in the season as evidenced by significantly higher boll retention among the endophyte treatment groups relative to the untreated control plants.

Figure 8:
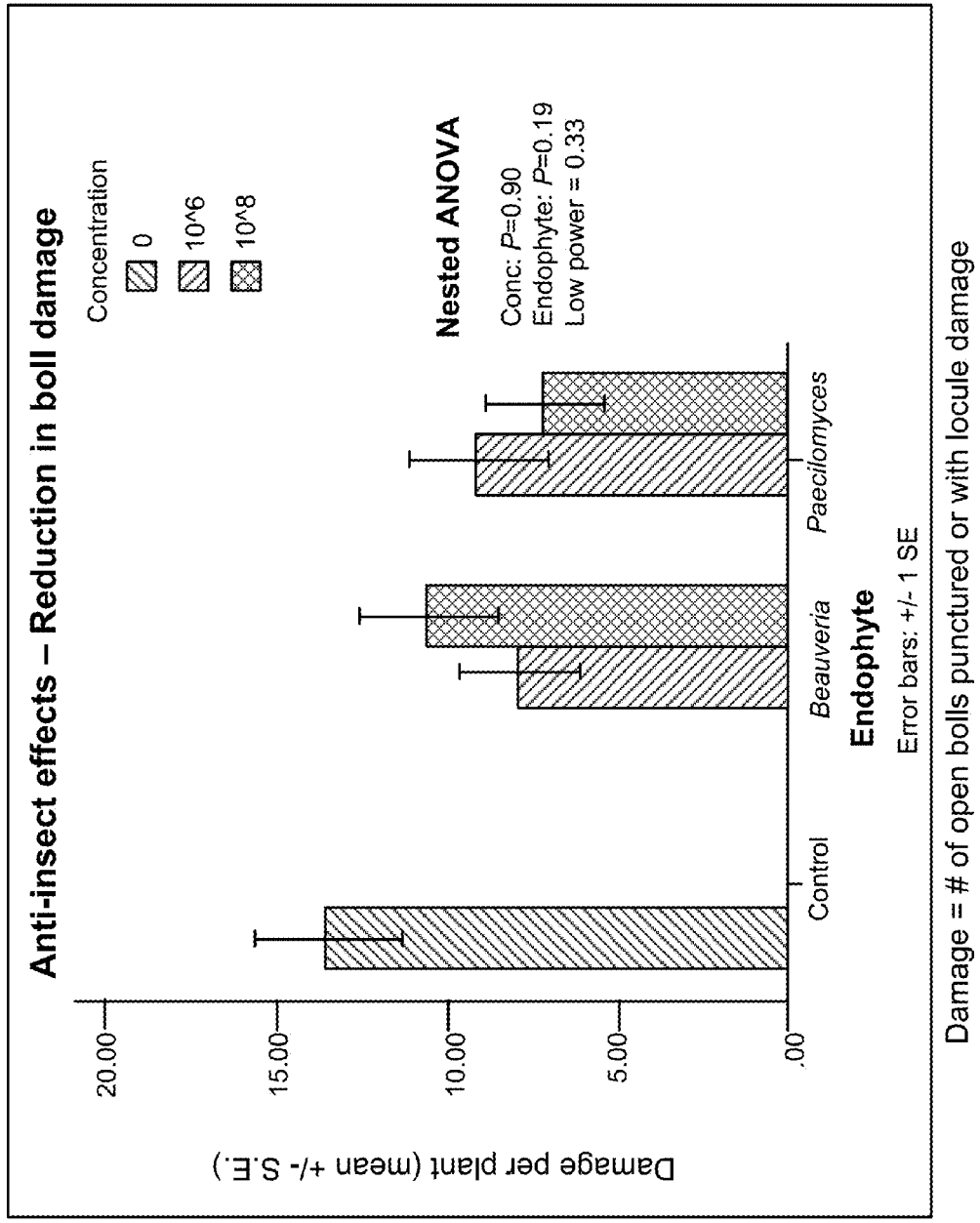
FIG. 8: A reduction in cotton boll damage was observed during field trials. Relative to control plants, levels of insect-related boll damage were lower among plants that were treated by soaking seeds in spore solutions of *Beauveria bassiana* and *Paecilomyces lilacinus* at concentrations of $10^6$ and $10^8$ spore/ml.

FIG. 8 demonstrates reduction in cotton boll damage during field trials. Relative to control plants, levels of insect-related boll damage were lower among plants that were treated by soaking seeds in spore solutions of *Beauveria bassiana* and *Paecilomyces lilacinus* at concentrations of $10^6$ and $10^8$ spore/ml. Positive effects of fungal endophytes on cotton plant performance under field conditions.

Example 11

Endophyte Treatment Increases Yield

Figure 11:
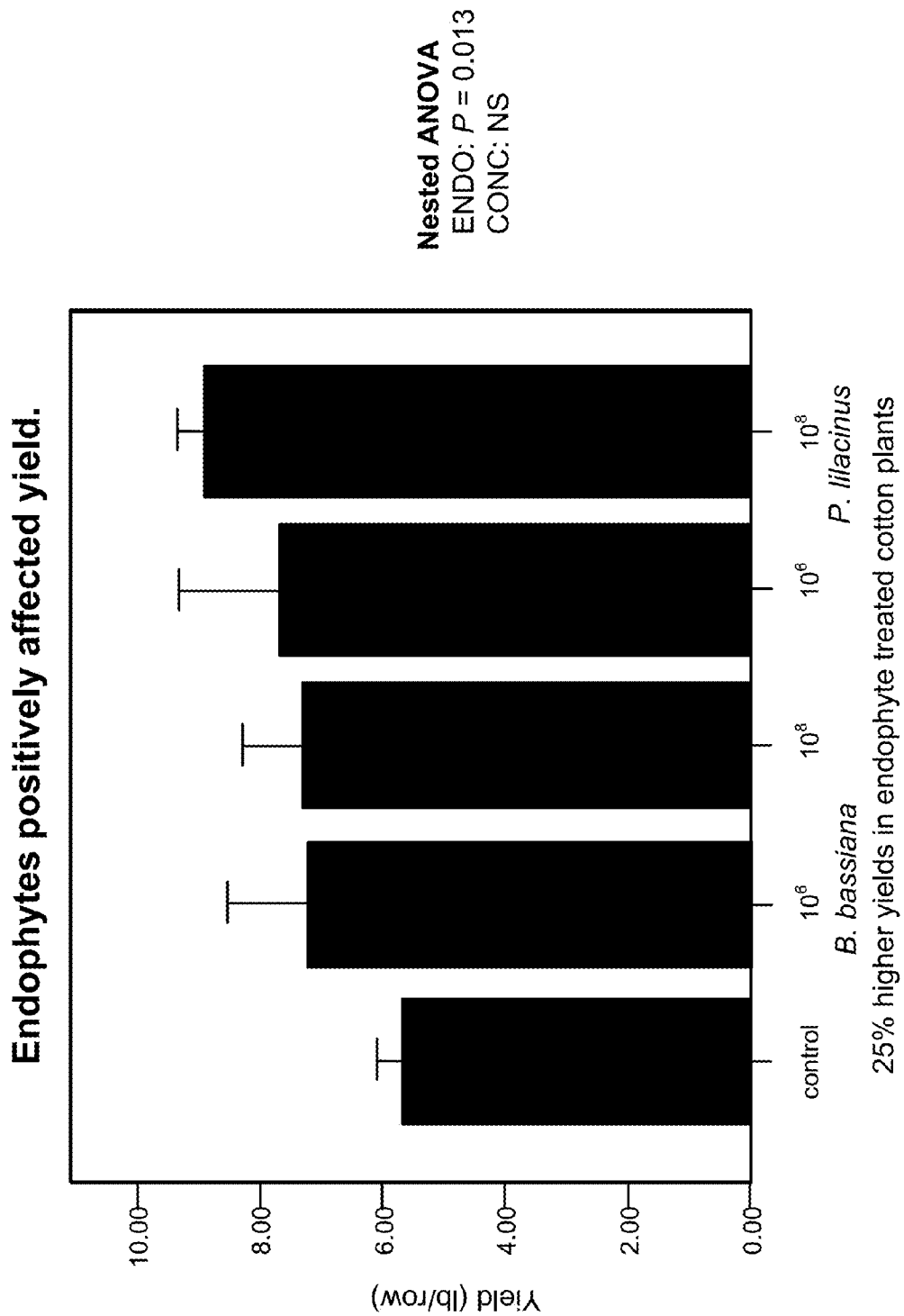
FIG. 11: Positive effects of fungal endophytes on cotton yields under field conditions. The data demonstrate that endophyte treatments achieved 25% higher yields in treated cotton plants.

At the end of the field trial employing endophyte treatment and treatment plants, plots were machine harvested with a 1-row picker. Surprisingly, the final yields at harvest were significantly higher than expected (25% higher than the untreated controls). Unexpectedly, treatment with *Paecilomyces lilacinus* or *Beauveria bassiana* resulted in higher yields than untreated control plants with regardless of the initial seed treatment concentration. (FIG. 11)

Example 12

Endophyte Treatment of Sorghum Increased Growth in the Greenhouse

Figure 12A:
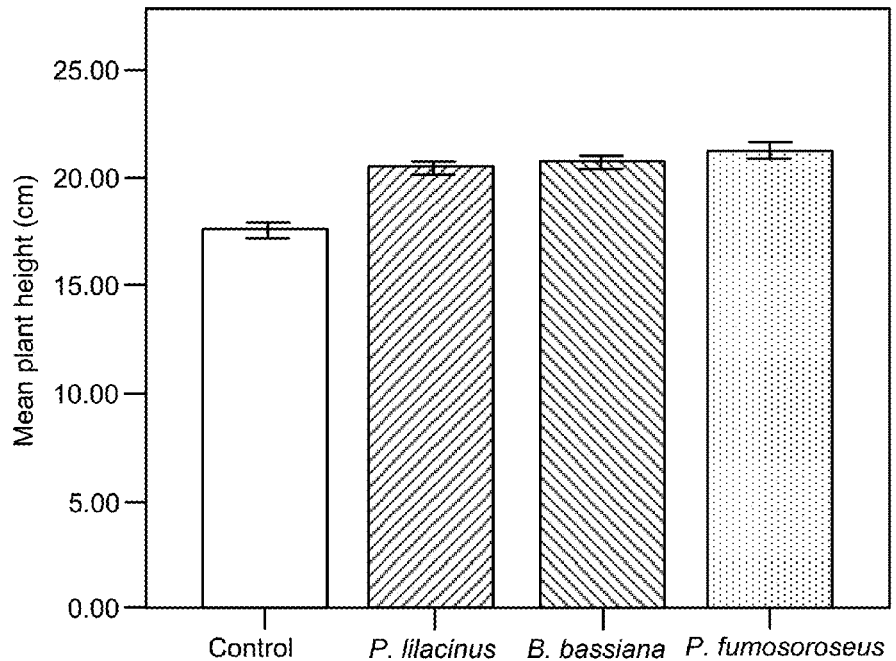
FIG. 12: Positive effects of fungal endophytes on sorghum (a) plant height and (b) total fresh biomass under growth chamber seedling assays. Data shown is average plant height (cm) and total fresh biomass (g) of n=10 independent replicates. Error bars represent±1 standard error. All three fungal endophytes improve both traits relative to the untreated control.
Figure 12B:
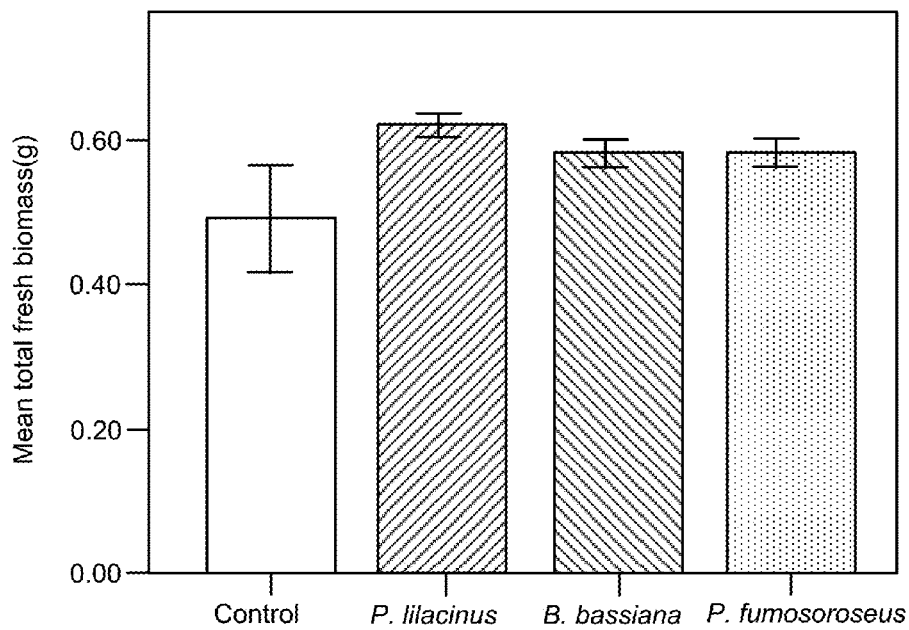

The effect of the described microbial compositions on sorghum was tested in a seedling assay. Sorghum bicolor seeds were surface sterilized using ethanol and bleach as described in Example 1 for cotton. Three strains (*B. bassiana, P. fumosoroseus,* and *P. lilacinus*) were prepared as conidia suspensions at $10^7$ conidia/ml, and coated on the sorghum seeds as described in Example 1. Control seeds were soaked in sterile water instead of a conidia suspension. Planted seeds were held in constant growth chamber conditions for two weeks at a replication of 10. At the end of two weeks, the plants were removed from the growth chamber and the plant height and biomass were measured. FIG. 12A shows the increase in plant height when applied with the described microbial composition relative to the control (p<0.05). FIG. 12B shows the increase in plant biomass in plants grown from seed that were treated with the described microbial composition relative to the control (p<0.05).

Example 13

Figure 13:
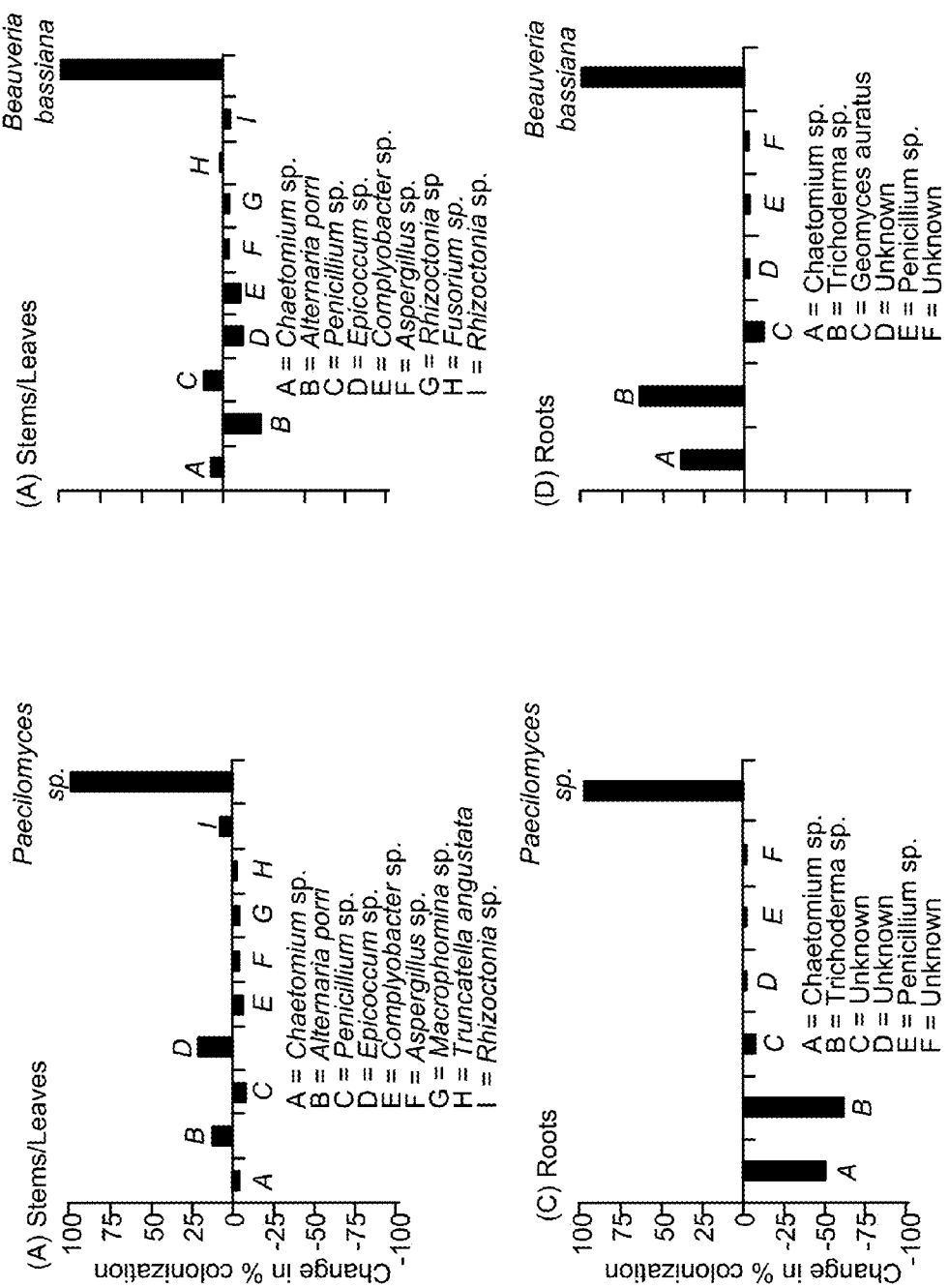
FIG. 13: The in-field modulation of the colonization of endogenous cotton endophytes in (a, b) stems and (c, d) roots when treated with fungal endophytes *Paecilomyces lilacinus* (a, c) and *Beauveria bassiana* (b, d). Data shown is a percentage change in colonization relative to the corresponding untreated control and plant tissue.

Treatment with Fungal Endophytes Modulates the Colonization Frequencies of Native Endophytes To determine whether endophyte seed treatments could alter the microbiome of the plant grown from the seed, cotton seeds were treated with spore suspensions of *Paecilomyces lilacinus* or *Beauveria bassiana*. Plants were grown in the field as part of a field trial planted and maintained under standard agricultural practices. Endophytic fungi were isolated on PDA media separately from surface-sterilized above-ground stem/leaf and below-ground root tissue to assess changes in the microbial community. The comparison shown in FIG. 13 is relative to the fungal endophyte communities in untreated control plants. The results show that these treatments can alter the colonization rates of native fungal endophytes.

Fungal endophyte treatments may alter the colonization frequencies of any of the fungal endophytes naturally present in plants. To determine what other native endophytes may be affected by seed treatments with fungal endophytes, the identity of cotton fungal endophytes isolated from plants of two commercial cotton varieties, CG3787B2RF and PHY499WRF, were assessed. The samples were obtained during a variety trial near Lubbock, Tex., USA identified as Lubbock-RACE. One single healthy leaf was collected from each of nine individual plants sampled per variety across multiple replicate plots arranged in a randomized block design to control for spatial variation in the field. To identify the fungal endophyte species, whole genomic DNA was extracted and the ribosomal DNA internal transcribed spacer (ITS) region was amplified as a barcode for 454 pyrosequencing using ITS1F forward and ITS2 reverse universal fusion primers. The fungal endophytes identified in this experiment, along with those shown in FIG. 13, are listed in Table 2.

TABLE 2

Native fungal endophytes that may be altered by seed treatments with other fungal endophytes

| Phylum | Class | Order | Family | Genus species |
|---|---|---|---|---|
| Ascomycota | | | | |
| | Leotiomycetes | | | |
| | Leotiomycetes | | | *Geomyces auratus* |
| | Dothideomycetes | Botryosphaeriales | Botryosphaeriaceae | *Macrophomina sp.* |
| | Dothideomycetes | Capnodiales | Davidiellaceae | |
| | Dothideomycetes | Capnodiales | Davidiellaceae | *Cladosporium sp.* |
| | Dothideomycetes | Capnodiales | Davidiellaceae | *Cladosporium cladosporioides* |

TABLE 2-continued

Native fungal endophytes that may be altered by seed treatments with other fungal endophytes

| Phylum | Class | Order | Family | Genus species |
|---|---|---|---|---|
| | Dothideomycetes | Capnodiales | Davidiellaceae | *Davidiella sp.* |
| | Dothideomycetes | Capnodiales | Mycosphaerellaceae | *Cercospora sp.* |
| | Dothideomycetes | Capnodiales | Mycosphaerellaceae | *Cercospora beticola* |
| | Dothideomycetes | Pleosporales | | |
| | Dothideomycetes | Pleosporales | Pleosporaceae | |
| | Dothideomycetes | Pleosporales | Pleosporaceae | *Alternaria sp.* |
| | Dothideomycetes | Pleosporales | Pleosporaceae | *Alternaria alternata* |
| | Dothideomycetes | Pleosporales | Pleosporaceae | *Alternaria citri* |
| | Dothideomycetes | Pleosporales | Pleosporaceae | *Alternaria porri* |
| | Dothideomycetes | Pleosporales | Pleosporaceae | *Alternaria tenuissima* |
| | Dothideomycetes | Pleosporales | Pleosporaceae | *Cochliobolus sp.* |
| | Dothideomycetes | Pleosporales | Pleosporaceae | *Curvularia sp.* |
| | Dothideomycetes | Pleosporales | Pleosporaceae | *Epicoccum sp.* |
| | Dothideomycetes | Pleosporales | Pleosporaceae | *Exserohilum sp.* |
| | Dothideomycetes | Pleosporales | Pleosporaceae | *Lewia sp.* |
| | Dothideomycetes | Pleosporales | Pleosporaceae | *Lewia infectoria* |
| | Dothideomycetes | Pleosporales | Pleosporaceae | *Pyrenophora sp.* |
| | Dothideomycetes | Pleosporales | Pleosporaceae | *Pyrenophora tritici-repentis* |
| | Dothideomycetes | Pleosporales | Pleosporaceae | *Pleospora sp.* |
| | Dothideomycetes | Pleosporales | Didymellaceae | *Phoma americana* |
| | Dothideomycetes | Pleosporales | Sporormiaceae | *Preussia africana* |
| | Eurotiomycetes | Chaetothyriales | | |
| | Eurotiomycetes | Chaetothyriales | Chaetothyriaceae | |
| | Eurotiomycetes | Eurotiales | Trichocomaceae | |
| | Eurotiomycetes | Eurotiales | Trichocomaceae | *Aspergillus sp.* |
| | Eurotiomycetes | Eurotiales | Trichocomaceae | *Penicillium sp.* |
| | Eurotiomycetes | Eurotiales | Trichocomaceae | *Thermomyces sp.* |
| | Eurotiomycetes | Eurotiales | Trichocomaceae | *Thermomyces lanuginosus* |
| | Saccharomycetes | Saccharomycetales | | |
| | Saccharomycetes | Saccharomycetales | Saccharomycetaceae | |
| | Saccharomycetes | Saccharomycetales | Saccharomycetaceae | *Candida sp.* |
| | Saccharomycetes | Saccharomycetales | Saccharomycetaceae | *Candida quercitrusa* |
| | Saccharomycetes | Saccharomycetales | Saccharomycetaceae | *Candida tropicalis* |
| | Saccharomycetes | Saccharomycetales | Saccharomycetaceae | *Cyberlindnera sp.* |
| | Saccharomycetes | Saccharomycetales | Saccharomycetaceae | *Cyberlindnera jadinii* |
| | Saccharomycetes | Saccharomycetales | Saccharomycetaceae | *Kluyveromyces sp.* |
| | Saccharomycetes | Saccharomycetales | Saccharomycetaceae | *Kluyveromyces marxianus* |
| | Sordariomycetes | | | |
| | Sordariomycetes | Diaporthales | Gnomoniaceae | *Gnomoniopsis sp.* |
| | Sordariomycetes | Hypocreales | Cordycipitaceae | *Beauveria bassiana* |
| | Sordariomycetes | Hypocreales | Cordycipitaceae | *Cordyceps sp.* |
| | Sordariomycetes | Hypocreales | Cordycipitaceae | *Cordyceps bassiana* |
| | Sordariomycetes | Hypocreales | Nectriaceae | |
| | Sordariomycetes | Hypocreales | Nectriaceae | *Fusarium sp.* |
| | Sordariomycetes | Hypocreales | Hypocreaceae | |
| | Sordariomycetes | Hypocreales | Hypocreaceae | *Gibellulopsis nigrescens* |
| | Sordariomycetes | Hypocreales | Hypocreaceae | *Hypocrea sp.* |
| | Sordariomycetes | Hypocreales | Hypocreaceae | *Hypocrea lixii* |
| | Sordariomycetes | Hypocreales | Hypocreaceae | *Hypocrea virens* |
| | Sordariomycetes | Hypocreales | Hypocreaceae | *Trichoderma sp.* |
| | Sordariomycetes | Hypocreales | Hypocreaceae | *Trichoderma tomentosum* |
| | Sordariomycetes | Hypocreales | Plectosphaerellaceae | *Verticillium sp.* |
| | Sordariomycetes | Ophiostomatales | Ophiostomataceae | |
| | Sordariomycetes | Ophiostomatales | Ophiostomataceae | *Ophiostoma sp.* |
| | Sordariomycetes | Ophiostomatales | Ophiostomataceae | *Ophiostoma dendifundum* |
| | Sordariomycetes | Sordariales | Chaetomiaceae | *Chaetomium sp.* |
| | Sordariomycetes | Sordariales | Chaetomiaceae | *Chaetomium globosum* |
| | Sordariomycetes | Sordariales | Chaetomiaceae | *Thielavia hyrcaniae* |
| | Sordariomycetes | Sordariales | Chaetomiaceae | *Taifanglania sp.* |
| | Sordariomycetes | Sordariales | Chaetomiaceae | *Taifanglania inflata* |
| | Sordariomycetes | Sordariales | Lasiosphaeriaceae | *Schizothecium inaequale* |
| | Sordariomycetes | Trichosphaeriales | Trichosphaeriaceae | *Nigrospora sp.* |
| | Sordariomycetes | Xylariales | Amphisphaeriaceae | *Truncatella angustata* |
| Basidiomycota | Agaricomycetes | Cantharellales | Ceratobasidiaceae | *Rhizoctonia sp.* |
| | Agaricomycetes | Corticiales | Corticiaceae | |
| | Agaricomycetes | Corticiales | Corticiaceae | *Phanerochaete sp* |
| | Agaricomycetes | Polyporales | Coriolaceae | |
| | Agaricomycetes | Polyporales | Coriolaceae | *Trametes sp.* |

TABLE 2-continued

Native fungal endophytes that may be altered by seed treatments with other fungal endophytes

| Phylum | Class | Order | Family | Genus species |
|---|---|---|---|---|
| | Agaricomycetes | Polyporales | Coriolaceae | *Trametes hirsuta* |
| | Agaricomycetes | Polyporales | Coriolaceae | *Trametes villosa* |
| | Agaricomycetes | Russulales | Peniophoraceae | |
| | Microbotryomycetes | Sporidiobolales | | |
| | Microbotryomycetes | Sporidiobolales | Sporidiobolaceae | *Rhodotorula sp.* |
| | Microbotryomycetes | Sporidiobolales | Sporidiobolaceae | *Rhodotorula mucilaginosa* |
| | Tremellomycetes | | | |
| | Tremellomycetes | Tremellales | | |
| | Tremellomycetes | Tremellales | Tremellaceae | *Cryptococcus sp* |
| | Tremellomycetes | Tremellales | Tremellaceae | *Cryptococcus skinneri* |
| | Tremellomycetes | Tremellales | Tremellaceae | *Tremella sp.* |

Example 14

Fungal Endophyte Seed Treatment Leads to Modulation of Phytohormone Levels in Plants Grown from the Seed To determine whether fungal endophyte seed treatment affects phytohormone levels in plants grown from the seed, tissue was harvested from the root or third true leaf of cotton plants inoculated with either endophytic *Beauveria bassiana* or *Paecilomyces lilacinus*. The experiment was done with three endophyte treatments (uncolonized control, *B. bassiana* or *P. lilacinus*) and, for *Beauveria bassiana*, two herbivory treatments (no aphids, or aphid herbivory for either 1, 4, 8, 24 or 48 hours). Phytohormone levels for abscisic acid (ABA), tuberonic acid (12-OH-JA, an oxidation product of JA-Ile) (TA), ascorbic acid (AA), 12-Oxophytodienoic acid (a JA precursor) (OPDA), JA isoleucine (JA-Ile), and salicylic acid (SA) were assessed by LC-MS in leaf and root tissues separately. All phytohormone level comparisons were made versus plants in the uncolonized control group with significance at $P<0.05$. Phytohormone levels in plants grown from seed treated with *Beauveria bassiana* are shown in Table 3, and phytohormone levels in plants grown from seed treated with *Paecilomyces lilacinus* are shown in Table 4.

TABLE 3

Phytohormone levels in plants grown from seed treated with *Beauveria bassiana*

| Herbivory | Phytohormone | Tissue | Upregulated/downregulated | Tissue | Upregulated/downregulated |
|---|---|---|---|---|---|
| Yes | ABA | Leaves | Down at 8 hours of feeding | Roots | Upregulated at 48 hrs of feeding |
| No | | | Not significant | | Upregulated |
| Yes | TA | Leaves | Not significant | Roots | Upreguated at 48 hrs of feeding |
| No | | | Not significant | | Not significant |
| Yes | AA | Leaves | Down at 4 hrs up at 24 hrs | Roots | Up at 8 hrs down at 48 hrs |
| No | | | Not significant | | Upregulated |
| Yes | OPDA | Leaves | Not significant | Roots | Up at 4 hrs and 8 hrs |
| No | | | Not significant | | Upregulated |
| Yes | JA-Ile | Leaves | Up at 48 hrs | Roots | Up at 48 hrs |
| No | | | Not significant | | Upregulated |
| Yes | SA | Leaves | Up at 1 hr, 8 hr, 24 and 48 hr | Roots | Down at 4 hr the rest n.s |
| No | | | Not significant | | Not significant |

TABLE 4

Phytohormone levels in plants grown from seed treated with *Paecilomyces lilacinus*

| Yes | ABA | Leaves | Down at 48 hrs | Roots | Up at 1 hr and 8 hrs |
|---|---|---|---|---|---|
| Yes | TA | Leaves | down at 4 and 8 hrs | Roots | up at 4 hrs |
| Yes | AA | Leaves | down at 4 and 8 hrs | Roots | up at 4 hrs |
| Yes | OPDA | Leaves | down at 4 and 8 hrs | Roots | Up at 4 and 48 hrs, down at 24 hrs |
| Yes | JA-Ile | Leaves | Down at 8 and 48 hrs | Roots | Up at 4 and 24 hrs |
| Yes | SA | Leaves | Up at 1 and 4 hr, down at 8 hrs | Roots | Up at 1, down at 8 hrs |

Example 15

Figure 14:
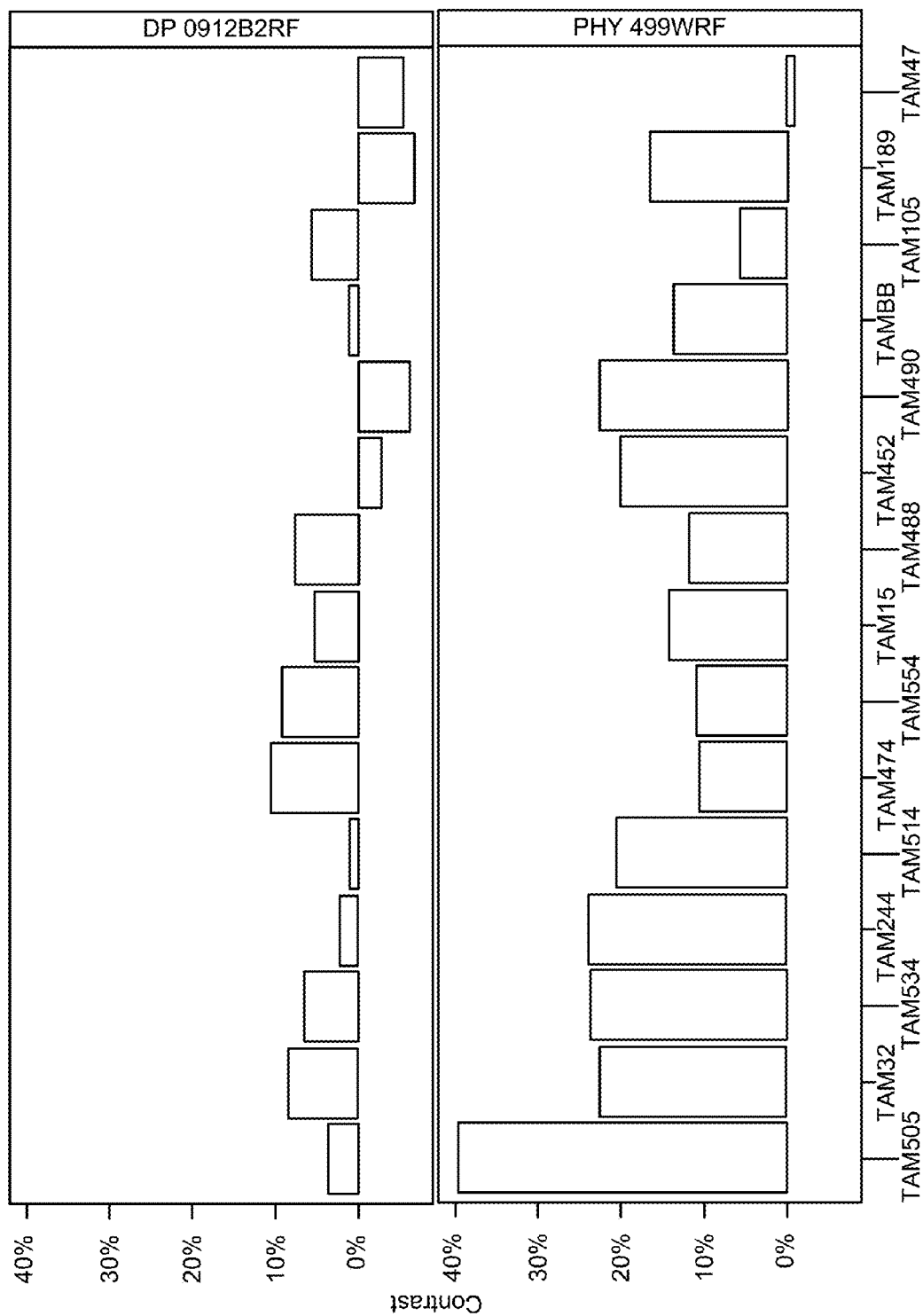
FIG. 14: Average percent difference in yield between endophyte treated and control cotton plants (n=6 replicate plots in a dryland field, College Station, Tex.) for 15 facultative fungal endophytes in the Phytogen (PHY 499WRF) cultivar.
Figure 15:
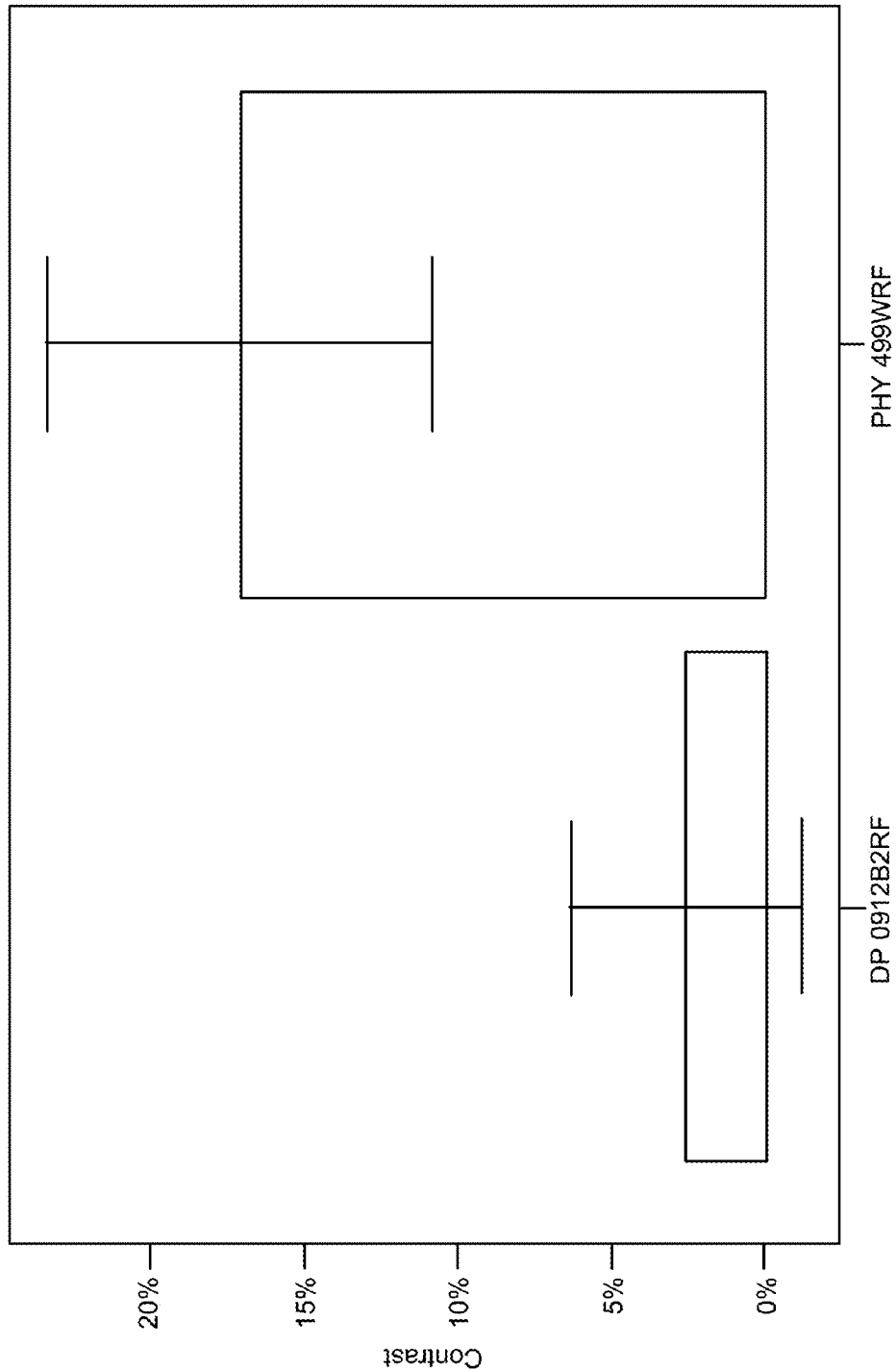
FIG. 15: Aggregated average percent difference in yield between endophyte treated and control cotton plants (n=6 replicate plots in a dryland field, College Station, Tex.) for 15 facultative fungal endophytes and two cotton cultivars; Delta Pine (DP 0912B2RF) and Phytogen (PHY 499WRF). Bars represent a 95% confidence interval around the mean.

Fungal Endophyte Seed Treatments Alter Traits in Certain Cotton Cultivars in Field Trials The 2014 field trials were executed in a similar fashion as described in Example 6. A field trial using isolates of listed below was conducted during the summer. Each plot consisted of four 15.24 m (40 ft) rows, each separated by 101.6 cm (40 in), and there were 6 replicate plots per treatment. Yield from plots treated with the described microbial compositions was compared relative to the untreated control plots. For thrips, this damage assessment was on a scale of 0-5; 0=no damage, 1=noticeable feeding scars, but no stunting, 2=noticeable feeding and 25% stunting, 3=feeding with blackened leaf terminals and 50% stunting, 4=severe feeding and 75% stunting, and 5=severe feeding and 90% stunting. For fleahoppers, the number of insects per plant were quantified and reported as an average for each plot. FIG. 14 shows the yield improvement of crops when treated with the described microbial compositions, for Delta Pine and Phytogen cultivars, respectively. FIG. 15 shows the aggregated yield improvement of the microbes across the two cultivars. Bars represent 95% confidence intervals. FIG. 16A shows the beneficial effect of 12 out of 15 microbial compositions tested on thrip damage in the Delta Pine cultivar. In the Phytogen cultivar, only 2 out of the 15 microbial compositions tested showed a benefit by reducing thrip damage. FIG. 16B shows the beneficial effect of reducing fleahopper damage in the Phytogen cultivar, where 6 out of the 15 facultative fungal endophytes tested showed an average decrease in fleahopper damage as compared to untreated cotton plants. In the Delta Pine cultivar, only one microbial composition showed a beneficial effect on fleahopper damage.

Figure 17B:
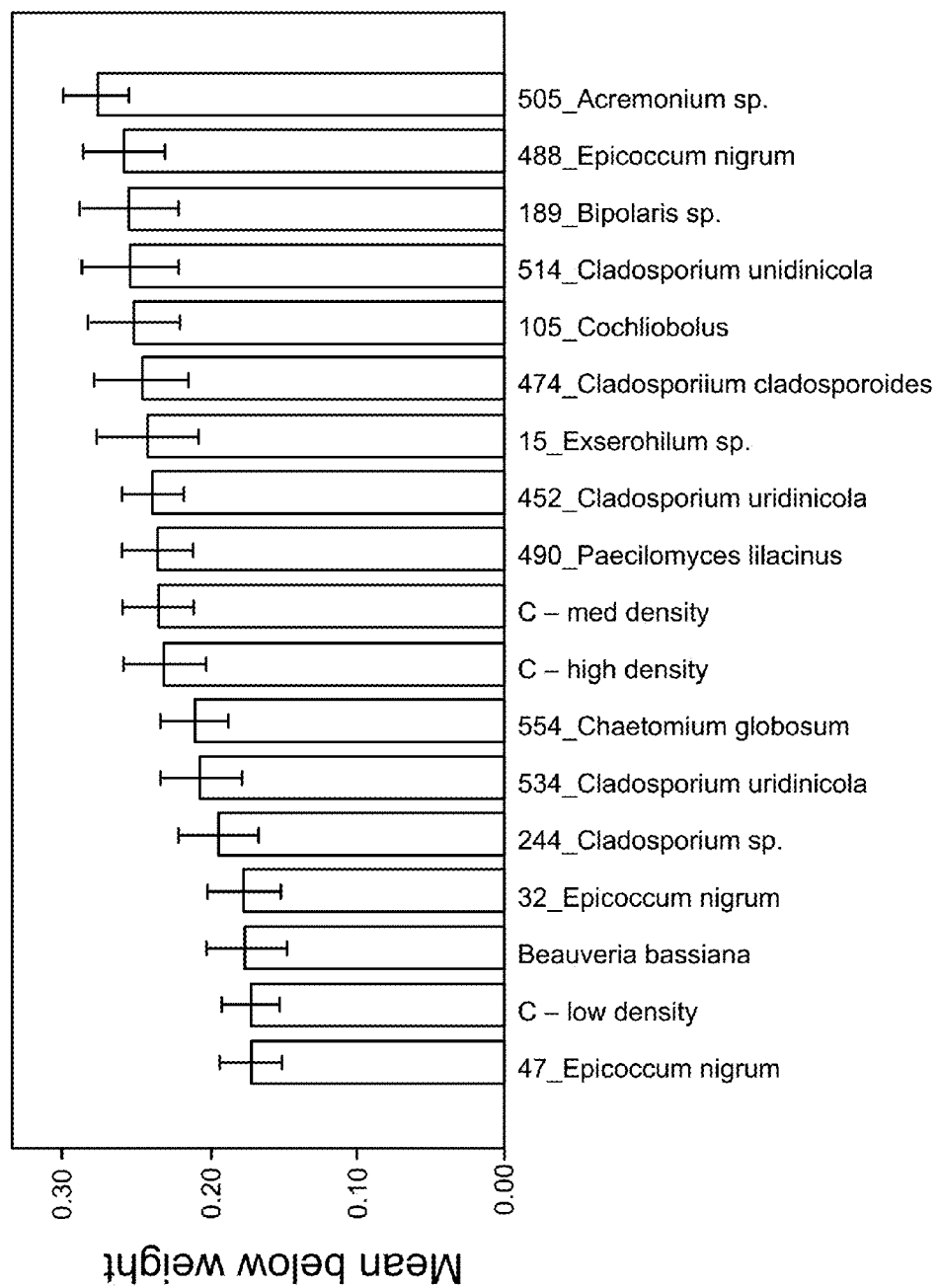
FIG. 17: Mid-season field-trait measured in June at the dryland trial of (A) root length and (B) belowground weight. Data presented is the average of n=10 independent replicates and error bars represent±one standard error.
Figure 18:
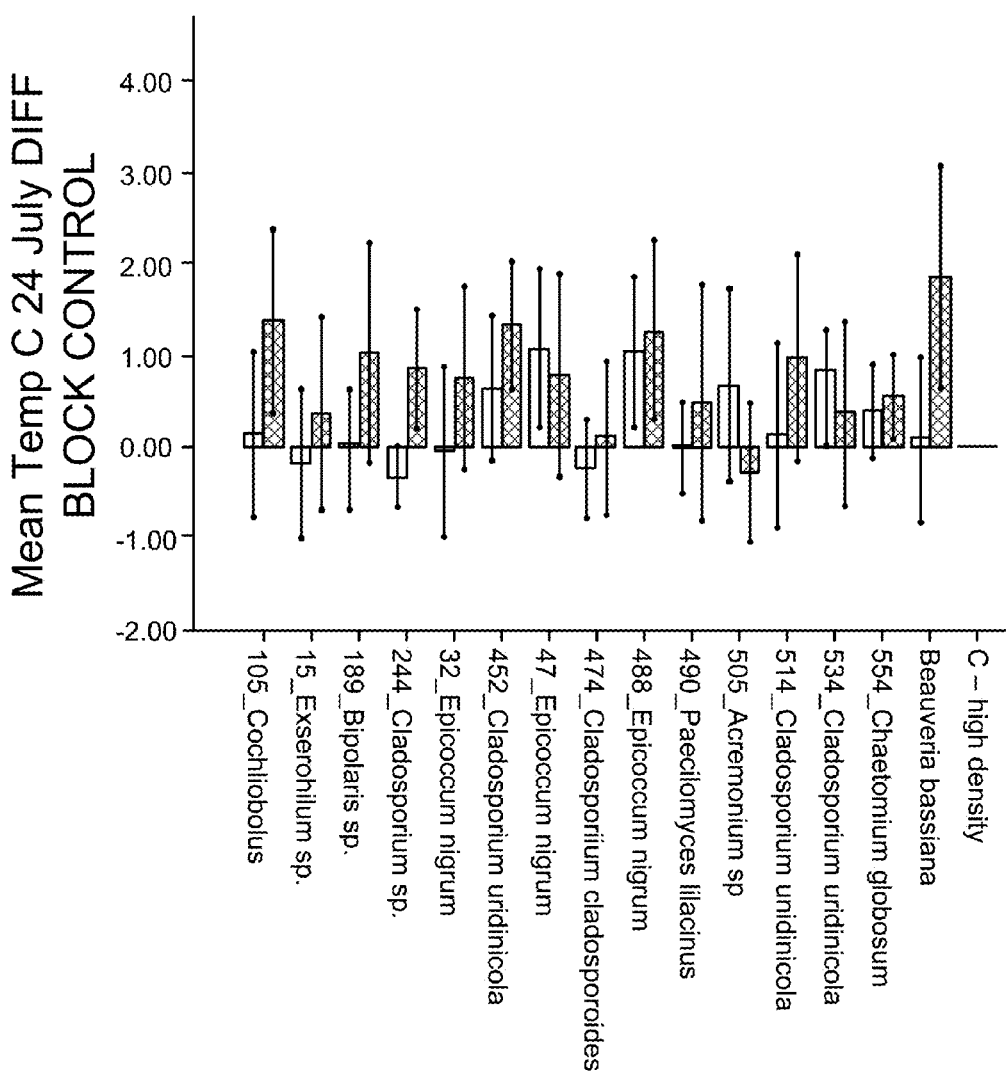
FIG. 18: Mid-season field-trait measured in July at the dryland trial of canopy temperature (Celsius) for the (blue bars) Delta Pine and (green bars) Phyton cultivars. Data presented is the block-controlled average of n=10 independent replicates, relative to the control plot and error bars represent±one standard error.
Figure 19:
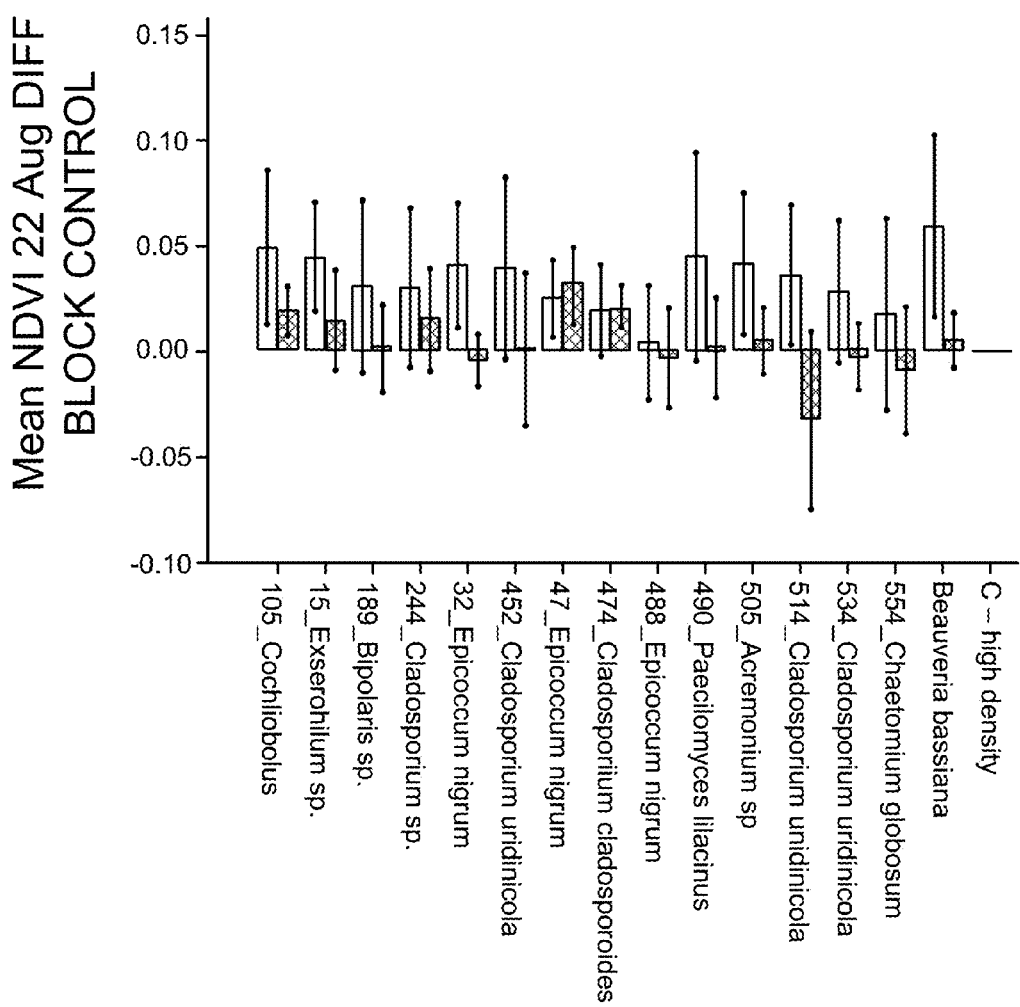
FIG. 19: Mid-season field-trait measured in August at the dryland trial of NDVI for the (blue bars) Delta Pine and (green bars) Phyton cultivars. Data presented is the block-controlled average of n=10 independent replicates, relative to the control plot and error bars represent±one standard error.
Figure 20:
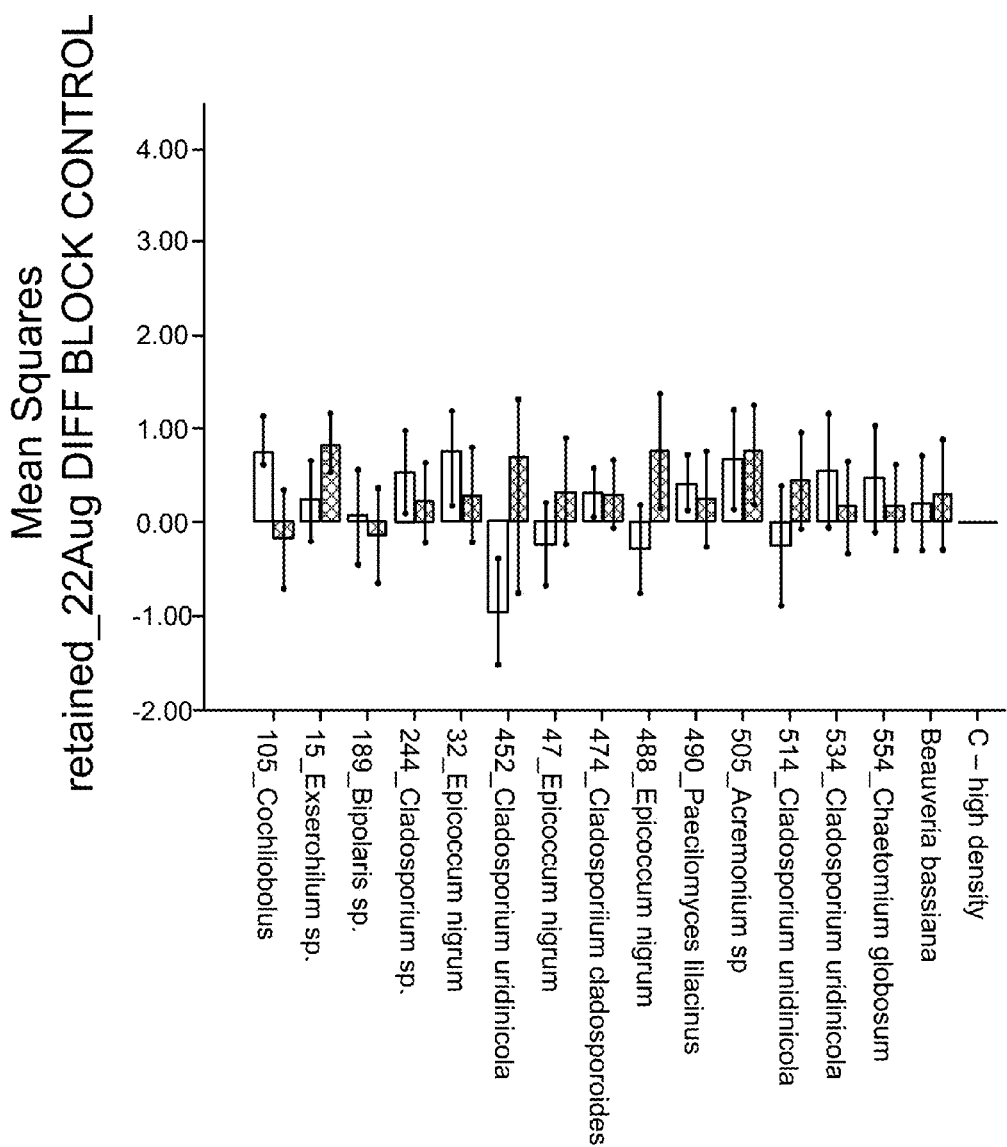
FIG. 20: Mid-season field-trait measured in August at the dryland trial of first position square retention for the (blue bars) Delta Pine and (green bars) Phyton cultivars. Data presented is the block-controlled average of n=10 independent replicates, relative to the control plot and error bars represent±one standard error.
Figure 21:
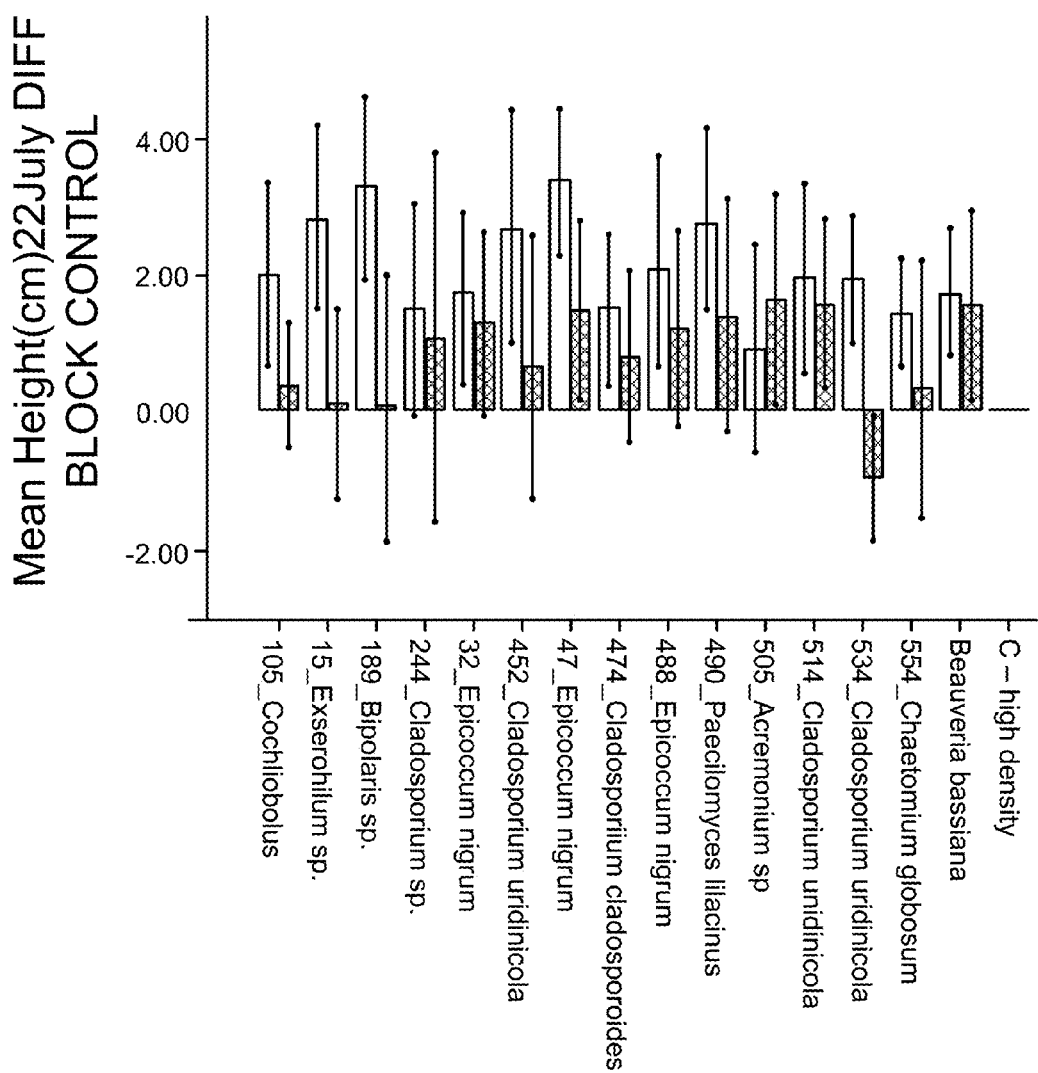
FIG. 21: Mid-season field-trait measured in August at the dryland trial of plant height (cm) for the (blue bars) Delta Pine and (green bars) Phyton cultivars. Data presented is the block-controlled average of n=10 independent replicates, relative to the control plot and error bars represent±one standard error.
Figure 22:
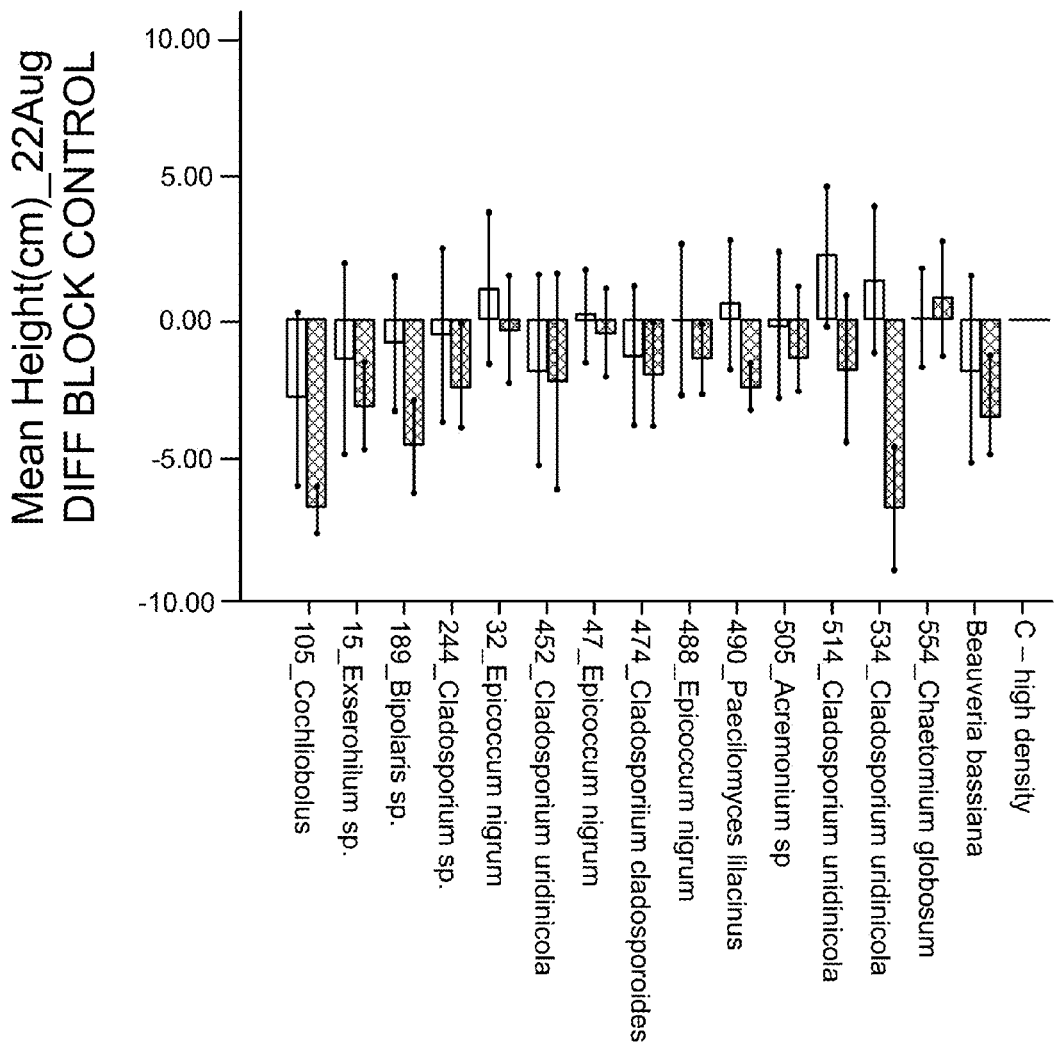
FIG. 22: Mid-season field-trait measured in July at the dryland trial of plant height (cm) for the (blue bars) Delta Pine and (green bars) Phyton cultivars. Data presented is the block-controlled average of n=10 independent replicates, relative to the control plot and error bars represent±one standard error.
Figure 23:
FIG. 23: Picture showing increased biomass in the plants treated with endophytes (right half of the image) compared to untreated control (left half of the image).

A number of other mid-season plant traits were also assessed in the field to determine the effect of the described fungal endophyte compositions. FIG. 17A shows the beneficial increase of the described microbial compositions on mid-season mean root length. FIG. 17B shows the beneficial increase of the described fungal endophyte compositions on mid-season belowground weight. FIG. 18 shows the beneficial increase of the described fungal endophyte compositions on mid-season canopy temperature for both Delta Pine and Phyton cultivars. FIG. 19 shows the beneficial increase of the described fungal endophyte compositions on mid-season NDVI (Normalized Difference Vegetation Index) for both Delta Pine and Phytogen cultivars. NDVI is a measure of chlorophyll content. FIG. 20 shows the beneficial increase of the described fungal endophyte compositions on mid-season first-position square retention for both Delta Pine and Phytogen cultivars. FIG. 21 and FIG. 22 show the modulation (up in July and down in August) of mid-season plant height when treated with the described fungal endophyte compositions for both Delta Pine and Phytogen cultivars. FIG. 23 shows increased biomass in the plants treated with endophytes (right half of the image) compared to untreated control (left half of the image).

In FIGS. 15 through 22, TAM505 is *Acremonium* sp., TAM32 is *Epicoccum nigrum*, TAM534 is *Cladosporium urdinicola*, TAM244 is *Cladosporium* sp., TAM514 is *Cladosporium urdinicola*, TAM474 is *Cladosporium cladosporoides*, TAM554 is *Chaetomium globusum*, TAM15 is *Exserohilum* sp., TAM488 is *Epicoccum nigrum*, TAM452 is *Cladosporium urdinicola*, TAM490 is *Paecilomyces lilacinus*, TAMBB is *Beauveria bassiana*, TAM105 is *Cochliobolus* sp., TAM189 is *Bipolaris* sp., and TAM47 is *Epicoccum nigrum*.

Example 16

Fungal Endophyte Seed Treatments Provide Drought Tolerance in Cotton Cultivars in Greenhouse Trials Cotton plants were germinated from endophyte-treated and untreated control seeds in the greenhouse. All seeds watered for 7 days or until cotyledon stage using pre-determined soil saturation volume of water per plant. At 7 DAP, water was withheld from water stressed plants while controls continued to be watered. Time to wilt and time to death were measured at a max of 21 DAP. The data in FIG. 24 shows the mean time to wilt, and the data in FIG. 25 shows the mean time to death. Endophyte treatment increased the survival of plants subjected to drought stress in both the Delta Pine (DTP) and the Phytogen (PHY) cultivars. In FIGS. 24 and 25, endophyte number 194 is *Epicoccum nigrum*, 249 is *Cladosporium cladosporioides*, 355 is *Chaetomium globusum*, 46 is *Epicoccum* sp., 463 is *Cladosporium* sp., 534 is *Cladosporium uredinicola*, 554 is *Chaetomium globosum*, 58 is *Epicoccum nigrum*, and control is no endophyte treatment.

Example 17

Identification of Fungal Endophytes with at Least 97% Identity to Those in Table 1

All known fungal endophytes with 97% identity to SEQ ID NO:7 through SEQ ID NO:77 were identified and are listed here by accession number: FJ425672,AY526296,JQ760047, UDB014465,KC662098,HQ649874,JQ764783, EU881906,K F251285,JQ862870,AB019364,AB594796, JF773666,JN034678,KC343142,EU707899,AB62 7855, GU138704,JN695549,DQ279491,HM776417,AB361643, DQ782839,AF222826,EU682 199,DQ782833,EU054429, FJ025275,AY354239,AF222828,GU721921,GU721920, DQ09371 5,AJ309335,FR774125,JQ747741,EF042603, KC968942,HE584924,AY740158,FJ645268,H Q692590, GQ203786,AY233867,HE579398,AB777497,KF435523, DQ420778,JQ649365,AJ2 71430,GQ996183,EF070423, FJ172277,AF483612,JX675127,EF070420,EF070421, AB74159 7,JN225408,DQ019364,KF251279,EF194151, EU977196,JX981477,EU686115,JX021531,FJ 527863, AJ302451,AJ302455,JN975370,EU754952,AF284388, KF296855,AF502785,JX3172 07,AF502781,DQ278915, EU686867,KC179120,HM991270,AF284384,DQ632670, JQ75980 6,JQ747685,EU885302,GU721781,EF434047, EF505854,JQ666587,JQ619887,GQ919270,K F531831, AB627854,DQ914679,DQ914681,HQ599592,DQ279490, DQ660336,JX069862,AB 607957,HE820869,FJ859345, JX966567,GU910230,AB627850,JX144030,DQ914723, HM59 5556,KC771473,DQ849310,EU179868,KF312152, JN890447,JX042854,EU554174,JN19851 8,HM992813, JQ845947,KF251310,JQ758707,AM930536,KF296912, JN865204,JN943512,G Q921743,EU245000,EU977304, EU144787,HE579322,HE579402,GU910171,HE792919, KC 960885,DQ485941,JN604449,HQ607913,AF502620, DQ468027,JX944132,JN207338,JQ922 240,JN207336, JX559559,JN207330,JN207333,HE820882,JX969625, HQ339994,JF744950,H E584937,JN120351,JX298885, DQ872671,AJ877102,JQ081564,DQ019391,AF071342, EF10 4180,JQ759755,GU827492,JN418769,GU324757, JX984750,JX256420,KF436271,JX205162,JN712450, KF435911,GU367905,JX416919,KC315933,JQ736648, AY904051,AF404126,FJ4 66722,HE584965,JN890282, HE584966,HQ166312,KC305124,HE977536,KC305128, AY907 040,JF710504,AF483609,AJ302460,AJ302461, AJ302462,AY969615,EU685981,U75615,AJ 302468,
FJ210503,GU237860,JX960591,JX143632,HM044649,
EU164404,HE584824,HQ116 406,DQ156342,JX416911,
U75617,GU721359,KC427041,EU254839,JX262800,
KC179307,HQ107993,KF361474,GU721420,HM053659,
EF619702,EU686156,HE820839,HQ634617,G U721810,
AB277211,AJ302417,KC315945,JQ002571,AM237457,
AF009805,JX489795,EU6 80554,KC507199,FJ236723,
HQ692618,JN846717,JX944160,JQ585672,KF435573,
EU52059 0,HM581946,DQ250382,JX243908,KC343184,
KC485454,GQ479695,GU237760,KF147147,EF619849,
GU237767,GU237766,AB818997,AF502847,EU683672,
KF225801,KC965743,AJ 488254,DQ825983,JN031007,
DQ825985,KF028765,AB818999,HQ238268,EU685984,
KC96 6180,HE998711,HQ533007,AM113729,KF251637,
FN394692,KF435172,JN207307,JQ8143 05,HM770988,
KC145175,AB511813,EU552102,AJ309344,EU645686,
JQ936328,JN038492,DQ875349,EU977228,JQ814357,
KF040480,JX317350,DQ401548,DQ318195,DQ318194,G
U721776,KF193449,AF178544,AM262354,AB540567,
AY627787,HE792907,HE579333,EU 445372,AF362069,
GU973687,HM053663,AB374284,DQ062977,GU237797,
JQ760783,EF0 29240,HM751829,FM200445,AY953383,
AY233922,JF742784,HM626650,FN610871,JX15 5902,
JX006065,AB566289,AF163078,AY344976,AB566287,
AF282089,AY251441,AF3956 93,JQ761899,AJ315835,
HQ187633,KC287233,AJ315831,HE820745,JN418779,
M13906,JQ7 61896,AJ315838,AY536373,HQ328035,
JX838793,JQ758986,HQ166357,JN163855,KC9655
95,JN545789,JN545788,GU944558,HE579247,KF296900,
EF377335,KC965954,GU269703,AB095511,EF419913,
DQ993641,AB325678,HQ223035,AY513945,FJ197013,
FR799277,H M071900,JN207293,FJ025268,JQ758966,
GU138733,GU138730,DQ267595,GQ919269,JF77 0450,
GU138734,DQ279488,DQ279486,DQ242472,EU164804,
EF104177,GU366726,KF212 243,DQ923534,GU079598,
JX987761,JX984765,AY585343,JQ769260,GU721919,
DQ92353 8,EU686756,EU040222,U75626,GU004264,
EU686753,JQ765651,JX270629,JN943408,EF0 42604,
AJ271588,HE579386,GQ479556,JQ759962,JX317413,
EU516867,DQ780361,JQ9056 44,HQ649792,JQ247355,
FN386296,AY004778,DQ102374,KF251383,GU237835,
DQ38364 2,FN868479,GU237814,KC343032,JN943394,
HQ450001,KC800573,AB217793,GQ851883,EU330630,
JF309198,AY489281,GU325687,JX399008,AB164703,
EF159407,AJ302429,UD B008141,UDB008140,
FM200496,AJ302426,AJ302422,AJ302423,JQ683725,
KF193481,JQ6 83727,HE792931,AB220252,FJ013057,
DQ286207,JQ759811,JF414842,JX088707,JN41575
4,AY787715,JX559577,KC776206,GU166440,KC460867,
FJ515595,KF056850,DQ118964,KC806227,KC631802,
EU823315,AY528970,HQ116401,JX317516,KF251313,
KC800565,A F502705,AF502810,JQ747697,AY527407,
EU680518,AJ621773,AB374285,HQ832827,GU1 74316,
DQ974750,JN198507,JF749806,JQ782739,HQ023202,
AY616234,KC965315,AB7437 81,EU554161,KC507201,
HM036624,EF464164,JX391942,AB743995,FJ415474,
AY647237,KC965503,AB540553,HQ377280,JX898571,
JN969419,DQ166962,HM123519,GU237881,A B683953,
AY681487,EU498738,EU687037,AB540550,EF394866,
AY853245,EU680532,HQ 450006,AM292674,KF435452,
AF502638,JN890354,JX256427,JF773646,KC916704,
FJ3470 31,JN572154,AF443850,AY273300,JQ247392,
JQ247393,HQ316569,GU324760,AB120858,JF440978,
HQ115719,JF440976,DQ124120,HQ022342,AF333138,
AB255293,GQ999456,DQ 286209,HE820785,AF451751,
JN038479,JQ044421,JQ044422,KC968911,KC492447,
FM172 902,AF437754,HM030631,HM595545,AY510424,
JX414184,HQ184179,AB588822,JQ8138 16,JQ813817,
FJ025255,AY745019,EU668292,HM216214,AF427105,
EU479799,JQ769257,HM484866,EU301059,EU564808,
AY265329,HQ701737,KC677889,AY907030,GU721349,
AY304513,GU062277,AY907037,HM484859,AB576865,
JX090109,UDB004179,JN692542,JQ327868,AY756490,
JN890185,JX042994,FJ613832,AF009815,HQ332534,
AF009816,EU6 86781,DQ520639,KC247154,HE820841,
HE820847,JN717228,JX944174,GU721348,AB444 657,
KF435560,JQ585546,JQ775577,UDB004443,JF744968,
KF192823,JN102440,AM50405 8,JX164074,GU907781,
HQ889707,FJ612980,KF251355,AF502854,AF350291,
HQ649989,G U966521,FJ481149,AY916491,AB444663,
FR799197,KC691458,HE820786,JN802324,AF14 9926,
AY372686,AY233908,HQ631033,UDB004677,KF251596,
EU479757,GU079602,KC6 91456,DQ420883,DQ914680,
DQ914683,KC305134,JN207313,AB512307,JN807326,
GQ395 365,JN207256,FJ425678,AB000932,JN207252,
KF293814,GU138728,AY160210,UDB01500 6,KC565735,
FJ524302,AF404127,EU272486,JF796251,JF439458,
AY304511,KC592278,JX 143583,JF440977,EU686925,
JX982370,EU687082,JX966607,GU222370,JN687988,
JN0067 71,JX436806,JQ936201,KF481950,AF178551,
KC181937,JX144778,DQ790541,JF796076,J X898576,
JX418352,AF097902,FJ411320,AF309617,FR863589,
HM469970,AF163069,KF58 2795,AB566293,HE820790,
GQ267191,JX130356,JN049828,HM060596,KF436001,
GQ9192 83,HQ832834,JN049822,EU041786,AB594789,
HE579259,HE584944,GU004268,GU237770,GQ921765,
HE579253,KC305158,AF043599,GQ267190,AY344968,
JN601031,JN969420,G U328624,AB540507,AM691002,
JN102384,EU480019,JN545815,DQ993651,JX130360,JX3
98990,AY969704,KF251559,AF395695,HQ449993,
U94714,KF435968,JX966550,AB85976 2,JF749808,
U94713,GU981750,AF177152,FJ430599,JQ647433,
GU981756,GU981757,EF10 4164,JN802311,GQ266146,
HQ445083,JX155909,KF436256,DQ318204,GU078649,
JN8901 15,DQ386141,GQ999487,EU686744,FJ426983,
UDB013022,FN435799,EF600976,HM59601 2,JF825143,
AM711381,EU816668,AJ972833,JQ905735,AF004686,
EU266103,EU266107,H Q166334,EF679384,UDB004580,
AM691001,JX399012,KC460880,JX982437,AB482221,A
M292048,KF251253,AF350308,JF502446,JQ905803,
KC179320,KF251393,GU053815,DQ3 23686,DQ323681,
KC343119,HE820747,KF251529,DQ676536,U17215,
DQ278919,EU4899 50,FR668016,GU903287,AJ302439,
AJ302438,AJ302435,AJ302434,JN807325,AB741584,K
C790941,DQ394387,FJ403513,GQ461566,KF193491,
KC305164,AF502895,GU237707,EU9 77520,AB247177,
AB482220,AY929321,GU004278,AB247171,GU461294,
GU461295,JX12 3570,AY684241,EU686968,JX944143,
JN871718,JQ796813,HQ829122,KF435590,KC80623
1,JX414183,GU944858,AF502733,JN662314,HQ022970,
AY510418,KC623569,KC216145,KF129059,DQ279515,
KF251526,JN192379,JN192376,HM140630,DQ006928,
AF011289,E U089663,FJ825373,DQ307292,JN890424,
KF155521,AB670714,GQ927271,AB670717,AB6 70711,
AB670713,KF435279,GU053814,KF435375,JX414188,
AF033422,GU225946,EU520 610,JF773645,KC595884,
KC965570,DQ812921,EU885299,DQ078757,FJ612618,
KF018920,JX077035,EU686911,JX270567,HE579352,
EU885297,FJ418185,DQ914724,HQ608112,HQ 450016,
GU174399,JN890327,HM999913,GU079580,HE584936,
JQ765675,GU726947,JQ76 5670,HM588120,AY969986,
JN120335,JQ247384,HQ891112,JQ769297,JN207242,
EU00288 8,EU479803,AY365468,AF163083,DQ534482, KC146356,KF436052,AF416460,JX537970,JX156018, AY907035,GQ241278,AF409972,JQ388941,FR668022, EU687151,DQ468026,AY251418,AB508842,AB508840, DQ233665,GU721949,AJ302444,JF927155,AJ302442, GU721976,AJ302440,KC790931,UDB004433,GU328539, EU479791,HQ649905,KC797566,JQ753968,GU721449, HQ701742,AY613410,GU062246,AY907045,HM991267, DQ979608,JQ781840,GU721442,EU426553,DQ980024, HQ634638,AF222836,GU222372,AY969338,EF104158,AY431101,JQ081415,FJ649318,AY152583,JN943058, EU885294,HQ231255,FJ179477,EU304350,KC005785, FR799224,EF070422,HQ533789,AJ289870,KF025952, HQ611347,DQ485934,KC989106,JQ081921,HE820871, AF404125,JN603182,KF436170,HQ832964,DQ185074,KC216108,JN102460,GU553324,DQ318207, HQ589260,AB819001,AY699669,EU812501,AB819004, HQ436065,KC013976,KF251204,KF435307,AF249905, EF029217,EF029216,FJ708614,EF029198,JQ517314, GU199416,HM180398,EU479748,GU721599,DQ185081, EF104175,JX021528,KF251430,AY611071,AY329221, JN207241,HM235963,JN890375,JF506092,KF193461, KF453551,HM123501,HM051074,AB255269,HQ904082, KF193500,FN562038,GU721911,EF417805,KF193504, KF028766,HE579312,EF433991,KF144910,KF144911,FM200450,AF163090,AB444665,AB444664,HQ649964, AB444666,AB444661,AY528998,DQ525492,KC870889, EF543844,GU073125,AY684240,JN163853,EU680538, AF395694,KC179102,KC778197,JN102425,DQ520638, EU244997,GU994552,DQ279527,KC179418,EF495164, AY999117,JX860441,JQ793663,DQ836775,EU479964, AY772736,AJ875343,KC013972,AJ875346,AY208785, HE614864,HF570009,KF435344,KC148376,EF641857, JX625368,AB512308,KC305146,AY266384,KC662096, HE579269,GU004277,GU004276,EF504668,EU687114, GU004272,GU004271,EU516731,KC213751,JN102394, HQ654776,JQ862729,EU687052,JX868653,FJ172294, JX130355,HE584891,FJ427063,GQ996174,FN252438, AJ633598,JX398987,EU245009,HM069466,FJ859344, JN942165,FJ785433,EF504592,HQ449989,HQ449988, JN120346,JX868648,EF600969,HQ529711,JN383815, KF003112,JN890192,GU981748,EU715654,EF535663, GU328634,UDB004320,GQ999475,FR731421,GU322457, EF550969,GU322450,FJ477838,KC305130,AJ247519, JQ026214,AJ972825,KC305135,EU520614,EU338415, JQ747670,EU040241,HE584979,KF477240,HM162095, AB746179,KC963934,AY906949,JN975339,EU520120, HM071902,JX399005,EU828350,JX399006,EF070418, FJ025231,EF070415,JN859327,JQ517292,JX399009, KF297004,JN618372,AY233888,EU784271,AM292673, EU514295,GQ921804,GU595027,HM008727,GU174426, JN673038,AF442801,EU686126,JF440982,EU754960, GQ154505,GU055711,FJ175159,KC354573,DQ993639, JQ621881,JN102454,AY177233,FJ013071,AY566992, GQ120971,EF408555,JX317505,AF524905,FJ887922, AF264905,AF264906,HM997113,EF619857,KC537805, KC537804,FJ887928,AB255303,HQ671302,FJ210537, FN386267,HQ649813,GU083033,KF251334,GU721297, KC181926,DQ832329,JQ781696,KF251233,KF251234, GQ505688,AJ437294,AJ437295,EF679363,HE820831, FN868450,GU174305,AY428866,AY956759,JQ759940, DQ489291,AJ271418,AY157952,EU784408,FJ427055, EF419900,FN813731,FJ427059,KF435462,JQ860113, KF209290,JF439437,KC565714,FJ228189,AF377282, JQ814364,HM991266,EF458676,AY762046,JN048884, HQ896484,HE579345,AB444659,EU076958,HQ402674, AF540504,AM922204,EU479758,JN943840,JN943841, FJ427025,KC584194,AF502754,FJ418192,KC343004, AB524806,AJ877224,DQ394377,FJ427028,AF282090, GQ927270,EU178738,DQ059579,EF535699,KF040479, AF163085,JX256429,AY999125,KF477238,KC513506, GQ999534,GU237837,EU002898,HM164732,AF443193, AJ315828,AJ315829,AY586560,JX868722,EU686847,DQ875350,DQ421277,AM176740,JX280875,AM691003, KF302463,GQ921786,KC965801,AM691004,EF452446, EU040235,KC662103,KC662102,AY251073,DQ993637, AY489282,FJ151434,JQ936199,EF505495,JN163856, JN659510,EF452449,EF504607.1,GQ516009.1,GQ508761.1,KC800847.1,JX187590.1,GQ508832.1, KC800841.1,KC800840.1,EF504876.1,HQ540685.1, EF505180.1,AY842353.1,GU014821.1,FJ761203.1, GQ510033.1,EF504642.1,GU014822.1,AY998786.1, AB581046.1,EF452470.1,FJ907534.1,EF504721.1, Y08744.2,FJ757587.1,GU014820.1,AF400896.1, KC800831.1,EF505804.1,EF505121.1,JX187587.1, KC800858.1,GQ866210.1,GQ522120.1,Y10748.1, EF504853.1,EF452471.1,KJ834329.1,AB581446.1,JX187588.1,AF163061.1,AB632670.1,Y08746.1,EF505082.1, JX187589.1,EF504723.1,AF400889.1,KC800835.1, and EF505282.1.

Example 18

Endophytes and Combination Thereof

The protocols as described in Examples 1-16 are used in connection with the endophytes of Table 1 to confirm beneficial properties on plant health, such as yield and/or past resistance, for example. In particular, endophytes from Table 1 are employed in a synthetic combination with a plant as described herein with crop plants, such as cotton. Any single or combination of endophytes listed in Table 1 can also be used in this manner, employing for example seed coatings or foliar, soil, or rhizosphere applications. A seed composition may comprise seeds and any combination of endophytes listed in Table 1. Endophytes listed in Table 1 or combinations thereof are thus employed in methods for preventing pest infestation, increased yield, treating a pest infestation, manufacturing pest-resistant seeds; or increasing a yield or reducing loss of a crop according to the methods of Examples 1-15.

What is claimed is:

1. A method for improving a trait in a cotton plant, the method comprising:
  contacting a seed of said cotton plant with a formulation comprising purified filamentous, spore-forming, facultative fungal endophytes of at least one species, wherein the facultative fungal endophytes are *Dothideomycetes* capable of producing substances that are beneficial to plants or detrimental to pests or both, and are present in the formulation in an amount effective to decrease colonization frequencies of endophytes of genus *Alternaria* native to the cotton plant and to provide a benefit to the cotton plant compared to a cotton plant grown from a seed untreated with the *Dothideomycetes* facultative fungal endophytes, wherein the benefit is selected from the group consisting of reduced nematode reproduction, reduced insect infestation, increased boll retention, increased yield, reduction of yield loss, increased growth, modulated phytohormone, enhanced resistance to drought stress, enhanced resistance to cold stress, enhanced resistance to heat stress, enhanced resistance to nutrient deficiency, enhanced resistance to salt toxicity, enhanced resistance to aluminum toxicity, enhanced resistance to grazing by herbivores, enhanced resistance to nematode infection, enhanced resistance to fungal infection, enhanced resistance to bacterial infection, enhanced resistance to viral infection and pest reduction.

2. The method of claim 1, wherein the facultative fungal endophyte is native to the cotton plant.

3. The method of claim 1, wherein the benefit is reduced nematode production.

4. The method of claim 1, wherein the benefit is reduced insect infestation.

5. The method of claim 1, wherein the benefit is increased boll retention.

6. The method of claim 1, wherein the benefit is increased yield by about 5%.

7. The method of claim 1, wherein the benefit is a reduction of yield loss by more than 5%.

8. The method of claim 1, wherein the benefit is enhanced resistance to drought stress.

9. The method of claim 1, wherein the formulation contains at least 100 ($10^2$) spores/ml or 100,000 ($10^5$) spores/g dry weight of the facultative fungal endophytes.

10. The method of claim 1, wherein the benefit is pest reduction.

11. The method of claim 10, wherein the pest is selected from the group consisting of a root knot nematode, an aphid, a lygus bug, a stink bug, or combinations thereof.

12. The method of claim 1, wherein the formulation comprises at least 2 species of facultative fungal endophytes.

13. The method of claim 1, wherein the formulation contains at least 1000 ($10^3$) spores/ml or 1,000,000 ($10^6$) spores/g dry weight of the facultative fungal endophytes.

14. The method of claim 1, wherein the formulation contains at least 1,000,000 ($10^6$) spores/ml of the facultative fungal endophytes.

15. The method of claim 6, wherein yield is increased by about 10%.

16. The method of claim 7, wherein yield loss is decreased by about 10%.

17. The method of claim 1, wherein the formulation contains at least 100 ($10^2$) spores/ml or 100,000 ($10^5$) spores/g dry weight of the facultative fungal endophytes and yield is increased by about 5%.

18. A synthetic combination of a cotton seed and purified filamentous, spore-forming facultative fungal endophytes of at least one species,
   wherein the facultative fungal endophytes are *Dothideomycetes* capable of producing substances that are beneficial to plants or detrimental to pests or both
   and are present in the synthetic combination in an amount effective to decrease the colonization frequencies of genus *Alternaria* native to the cotton plant grown from the seed and to provide a benefit to the cotton plant compared to a cotton plant grown from a seed untreated with the *Dothideomycetes* facultative fungal endophytes
   wherein the benefit is selected from the group consisting of reduced nematode reproduction, reduced insect infestation, increased boll retention, increased yield, reduction of yield loss, increased growth, modulated phytohormone, enhanced resistance to drought stress, enhanced resistance to cold stress, enhanced resistance to heat stress, enhanced resistance to nutrient deficiency, enhanced resistance to salt toxicity, enhanced resistance to aluminum toxicity, enhanced resistance to grazing by herbivores, enhanced resistance to nematode infection, enhanced resistance to fungal infection, enhanced resistance to bacterial infection, enhanced resistance to viral infection and pest reduction.

19. The synthetic combination of claim 18, wherein the facultative fungal endophytes are in spore form.

20. The synthetic combination of claim 18, wherein the benefit is reduced nematode production.

21. The synthetic combination of claim 18, wherein the benefit is enhanced resistance to drought stress.

22. The synthetic combination of claim 18, wherein the benefit is reduced insect infestation.

23. The synthetic combination of claim 18, comprising at least 2 species of facultative endophytes.

24. The synthetic combination of claim 18, wherein the benefit is increased yield by about 5%.

25. The synthetic combination of claim 18, wherein the benefit is a reduction of yield loss by more than 5%.

26. The synthetic combination of claim 18, wherein the facultative fungal endophyte is native to the cotton plant grown from the seed.

27. The synthetic combination of claim 18, wherein the facultative fungal endophytes are present at a concentration of at least 100 ($10^2$) spores/seed on the surface of the seed.

28. The synthetic combination of claim 18, wherein the facultative fungal endophytes are present at a concentration of at least 1,000 ($10^3$) spores/seed on the surface of the seed.

29. The synthetic combination of claim 18, wherein the facultative fungal endophytes are present at a concentration of at least 10,000 ($10^4$) spores/seed on the surface of the seed.

30. The synthetic combination of claim 24, wherein yield is increased by about 10%.

31. The synthetic combination of claim 25, wherein yield loss is reduced by about 10%.

32. The synthetic combination of claim 18, wherein the benefit is increased boll retention.

33. The synthetic combination of claim 18, wherein the benefit is pest reduction.

34. The synthetic combination of claim 33, wherein the pest is selected from the group consisting of a root knot nematode, an aphid, a lygus bug, and a stink bug.

35. The synthetic combination of claim 18, wherein the facultative fungal endophytes are present at a concentration of at least 100 ($10^2$) spores/seed on the surface of the seed and the yield is increased by about 5%.

* * * * *